(12) United States Patent
Gavai et al.

(10) Patent No.: US 9,133,139 B2
(45) Date of Patent: Sep. 15, 2015

(54) FLUOROALKYL-1,4-BENZODIAZEPINONE COMPOUNDS

(71) Applicant: BRISTOL-MYERS SQUIBB COMPANY, Princeton, NJ (US)

(72) Inventors: Ashvinikumar V. Gavai, Princeton Junction, NJ (US); Weifang Shan, Princeton, NJ (US); James Aaron Balog, Lambertsville, NJ (US); Claude A. Quesnelle, Skillman, NJ (US); Wen-Ching Han, Newtown, PA (US); George V. DeLucca, Pennington, NJ (US); Daniel O'Malley, New Hope, PA (US); Brian E. Fink, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/429,941

(22) PCT Filed: Sep. 20, 2013

(86) PCT No.: PCT/US2013/060833
§ 371 (c)(1),
(2) Date: Mar. 20, 2015

(87) PCT Pub. No.: WO2014/047392
PCT Pub. Date: Mar. 27, 2014

(65) Prior Publication Data
US 2015/0218111 A1    Aug. 6, 2015

Related U.S. Application Data

(60) Provisional application No. 61/703,928, filed on Sep. 21, 2012.

(51) Int. Cl.
| | | |
|---|---|---|
| *C07D 413/14* | (2006.01) | |
| *C07D 401/04* | (2006.01) | |
| *C07D 401/12* | (2006.01) | |
| *C07D 413/12* | (2006.01) | |
| *C07D 243/24* | (2006.01) | |
| *A61K 31/5513* | (2006.01) | |
| *C07D 491/056* | (2006.01) | |
| *A61K 45/06* | (2006.01) | |

(52) U.S. Cl.
CPC .......... *C07D 243/24* (2013.01); *A61K 31/5513* (2013.01); *A61K 45/06* (2013.01); *C07D 401/04* (2013.01); *C07D 401/12* (2013.01); *C07D 413/12* (2013.01); *C07D 413/14* (2013.01); *C07D 491/056* (2013.01)

(58) Field of Classification Search
CPC .. C07D 413/14; C07D 401/04; C07D 401/12; C07D 413/12
See application file for complete search history.

(56) References Cited

U.S. PATENT DOCUMENTS

| | | | |
|---|---|---|---|
| 4,981,847 | A | 1/1991 | Sato et al. |
| 5,322,842 | A | 6/1994 | Sato et al. |
| 5,324,726 | A | 6/1994 | Bock et al. |
| 5,852,010 | A | 12/1998 | Graham et al. |
| 5,998,407 | A | 12/1999 | Graham et al. |
| 6,331,408 | B1 | 12/2001 | Zaczek et al. |
| 6,495,540 | B2 | 12/2002 | Thompson |
| 6,503,901 | B1 | 1/2003 | Thompson et al. |
| 6,503,902 | B2 | 1/2003 | Olson et al. |
| 6,509,333 | B2 | 1/2003 | Olson |
| 6,525,044 | B2 | 2/2003 | Olson et al. |
| 6,544,978 | B2 | 4/2003 | Wu et al. |
| 6,632,812 | B2 | 10/2003 | Han et al. |
| 6,653,303 | B1 | 11/2003 | Wu et al. |
| 6,713,476 | B2 | 3/2004 | Yang et al. |
| 6,737,038 | B1 | 5/2004 | Zaczek et al. |
| 6,756,511 | B2 | 6/2004 | Castro Pineiro et al. |
| 6,759,404 | B2 | 7/2004 | Yang et al. |
| 6,794,381 | B1 | 9/2004 | Olson et al. |
| 6,878,363 | B2 | 4/2005 | Zaczek et al. |
| 6,900,199 | B2 | 5/2005 | Han et al. |
| 6,958,329 | B2 | 10/2005 | Olson |
| 6,960,576 | B2 | 11/2005 | Olson et al. |
| 6,962,913 | B2 | 11/2005 | Olson et al. |
| 6,984,626 | B2 | 1/2006 | Nadin et al. |
| 7,001,901 | B2 | 2/2006 | Yang |
| 7,053,081 | B2 | 5/2006 | Olson et al. |
| 7,053,084 | B1 | 5/2006 | Olson |
| 7,101,870 | B2 | 9/2006 | Olson et al. |
| 7,105,509 | B2 | 9/2006 | Castro Pineiro et al. |
| 7,112,583 | B2 | 9/2006 | Olson et al. |

(Continued)

FOREIGN PATENT DOCUMENTS

| | | |
|---|---|---|
| EP | 0669334 | 8/1995 |
| WO | WO 97/36879 | 10/1997 |

(Continued)

OTHER PUBLICATIONS

U.S. Appl. No. 14/627,537, filed Feb. 20, 2015, Gavai et al.

(Continued)

*Primary Examiner* — Bruck Kifle

(74) *Attorney, Agent, or Firm* — Gary D. Greenblatt

(57) ABSTRACT

Disclosed are compounds of Formula (I): wherein: $R_2$ is phenyl, fluorophenyl, chlorophenyl, trifluorophenyl, methylisoxazolyl, or pyridinyl; $R_3$ is H, $CH_3$, $CH_2$(cyclopropyl), pyridinyl, chloropyridinyl, or methoxypyridinyl: and $R_a$, $R_b$, y, and z are defined herein. Also disclosed are methods of using such compounds to inhibit the Notch receptor, and pharmaceutical compositions comprising such compounds. These compounds are useful in treating, preventing, or slowing the progression of diseases or disorders in a variety of therapeutic areas, such as cancer.

10 Claims, No Drawings

(56) References Cited

U.S. PATENT DOCUMENTS

| | | | |
|---|---|---|---|
| 7,125,866 | B1 | 10/2006 | Glick et al. |
| 7,153,491 | B2 | 12/2006 | Zaczek et al. |
| 7,160,875 | B2 | 1/2007 | Flohr et al. |
| 7,276,495 | B2 | 10/2007 | Han et al. |
| 7,276,496 | B2 | 10/2007 | Olson et al. |
| 7,304,049 | B2 | 12/2007 | Olson |
| 7,304,055 | B2 | 12/2007 | Olson et al. |
| 7,304,056 | B2 | 12/2007 | Olson et al. |
| 7,342,008 | B2 | 3/2008 | Olson et al. |
| 7,354,914 | B2 | 4/2008 | Olson |
| 7,375,099 | B2 | 5/2008 | Galley et al. |
| 7,390,802 | B2 | 6/2008 | Han et al. |
| 7,390,896 | B2 | 6/2008 | Olson et al. |
| 7,423,033 | B2 | 9/2008 | Olson et al. |
| 7,456,172 | B2 | 11/2008 | Olson |
| 7,456,278 | B2 | 11/2008 | Olson |
| 7,498,324 | B2 | 3/2009 | Han et al. |
| 7,528,249 | B2 | 5/2009 | Olson et al. |
| 7,544,679 | B2 | 6/2009 | Flohr et al. |
| 7,582,624 | B2 | 9/2009 | Carter et al. |
| 7,655,647 | B2 | 2/2010 | Han et al. |
| 7,718,795 | B2 | 5/2010 | Olson |
| 8,629,136 | B2 | 1/2014 | Gavai et al. |
| 8,822,454 | B2 | 9/2014 | Gavai et al. |
| 8,999,918 | B2 | 4/2015 | Gavai et al. |
| 2007/0185094 | A1 | 8/2007 | Lattmann et al. |
| 2009/0181944 | A1 | 7/2009 | Boylan et al. |
| 2014/0357805 | A1 | 12/2014 | Gavai et al. |

FOREIGN PATENT DOCUMENTS

| | | |
|---|---|---|
| WO | WO 01/74796 | 10/2001 |
| WO | WO 01/90084 | 11/2001 |
| WO | WO 2007/067048 | 6/2007 |
| WO | WO 2009/023453 | 2/2009 |
| WO | WO 2014/047369 | 3/2014 |
| WO | WO 2014/047370 | 3/2014 |
| WO | WO 2014/047374 | 3/2014 |
| WO | WO 2014/047390 | 3/2014 |
| WO | WO 2014/047391 | 3/2014 |
| WO | WO 2014/047393 | 3/2014 |
| WO | WO 2014/047397 | 3/2014 |

OTHER PUBLICATIONS

Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.

Seiffert, D., et al., "Presenilin-1 and -2 Are Molecular Targets for gamma-Secretase Inhibitors," The Journal of Biological Chemistry, vol. 275, No. 44, pp. 34086-34091 (2000).

Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).

Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).

Meredith, Jere, "Characterization of APP Activity and Notch Toxicity with gamma-Secretase Inhibitors," 8th International AD/PD Meeting, Salzberg, Austria, Mar. 17, 2007.

Prasad, C.V.C., et al., "Discovery of (S)-2-((S)-2(3,5-difluorophenyl)-2-hydroxyacetamido)-N-((S,Z)-3-methyl-4-oxo-4,5-dihydro-3H-benzo[d][1,2]diazepin-5-yl)propanamide (BMS-433796): A gamma-secretase inhibitor with with A beta lowering activity in a transgenic mouse model of Alzheimer's disease," Bioorganic & Medicinal Chemistry Letters 17 pp. 4006-4011 (2007).

Jun, H.T., et al., "Top NOTCH Targets: Notch Signaling in Cancer," Drug Development Research, 69, pp. 319-328 (2008).

Meredith, J.E., et al., gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18, 2007, Salzberg, Austria.

PCT/US2013/060833 International Search Report mailed Dec. 16, 2013.

PCT/US2013/060833 Preliminary Report on Patentability issued Mar. 24, 2015.

FLUOROALKYL-1,4-BENZODIAZEPINONE COMPOUNDS

CROSS REFERENCE TO RELATED APPLICATIONS

This application is a national phase application under 35 U.S.C. §371 of International Patent Application No. PCT/US2013/060833, filed Sep. 20, 2013, which claims priority to U.S. Provisional Application 61/703,928, filed Sep. 21, 2012, which are expressly incorporated fully herein by reference.

The present invention generally relates to benzodiazepinone compounds useful as Notch inhibitors. The invention further pertains to pharmaceutical compositions comprising at least one compound according to the invention that is useful for the treatment of conditions related to the Notch pathway, such as cancer and other proliferative diseases.

Notch signaling has been implicated in a variety of cellular processes, such as cell fate specification, differentiation, proliferation, apoptosis, and angiogenesis. (Bray, *Nature Reviews Molecular Cell Biology*, 7:678-689 (2006); Fortini, *Developmental Cell* 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Presenilin 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al., *Current Cancer Drug Targets*, 6:313-323 (2006); Bolos, V. et al., *Endocrine Reviews*, 28:339-363 (2007); Shih, I-M. et al., *Cancer Research*, 67:1879-1882 (2007); Yamaguchi, N. et al., *Cancer Research*, 68:1881-1888 (2008); Miele, L., *Expert Review Anticancer Therapy*, 8:1197-1201 (2008); Purow, B., *Current Pharmaceutical Biotechnology*, 10:154-160 (2009); Nefedova, Y. et al., *Drug Resistance Updates*, 11:210-218 (2008); Dufraine, J. et al., *Oncogene*, 27:5132-5137 (2008); and Jun, H. T. et al., *Drug Development Research*, 69:319-328 (2008).

There remains a need for compounds that are useful as Notch inhibitors and that have sufficient metabolic stability to provide efficacious levels of drug exposure. Further, there remains a need for compounds useful as Notch inhibitors that can be orally or intravenously administered to a patient.

U.S. Pat. No. 7,053,084 B1 discloses succinoylamino benzodiazepine compounds useful for treating neurological disorders such as Alzheimer's Disease. The reference discloses that these succinoylamino benzodiazepine compounds inhibit gamma secretase activity and the processing of amyloid precursor protein linked to the formation of neurological deposits of amyloid protein.

Applicants have found potent compounds that have activity as Notch inhibitors and have sufficient metabolic stability to provide efficacious levels of drug exposure upon intravenous or oral administration. These compounds are provided to be useful as pharmaceuticals with desirable stability, bioavailability, therapeutic index, and toxicity values that are important to their drugability.

SUMMARY OF THE INVENTION

The present invention fills the foregoing need by providing fluoroalkyl-1,4-benzodiazepinone compounds that are useful as selective inhibitors of Notch signaling pathway.

The present invention also provides pharmaceutical compositions comprising a pharmaceutically acceptable carrier; and at least one compound of Formula (I).

The present invention also provides a method of treating a disease or disorder associated with the activity of the Notch receptor, the method comprising administering to a mammalian patient at least one compound of Formula (I).

The present invention also provides processes and intermediates for making the compounds of Formula (I).

The present invention also provides the compounds of Formula (I) for use in therapy.

The present invention also provides the use of the compounds of Formula (I) for the manufacture of a medicament for the treatment of cancer.

The compounds of Formula (I) and compositions comprising the compounds are Notch inhibitors that may be used in treating, preventing or curing various Notch receptor-related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

DETAILED DESCRIPTION

The first aspect of the present invention provides at least one compound of Formula (I):

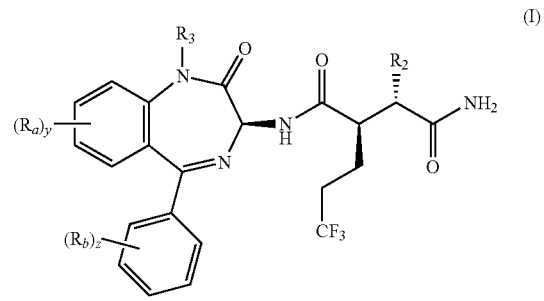

or at least one prodrug thereof, wherein:

$R_2$ is phenyl, fluorophenyl, chlorophenyl, trifluorophenyl, methylisoxazolyl, or pyridinyl;

$R_3$ is H, —$CH_3$, —$CH_2$(cyclopropyl), pyridinyl, chloropyridinyl, or methoxypyridinyl;

each $R_a$ is independently F, Cl, —$CH_3$, —$OCH_3$, —CN, and/or —O(cyclopropyl);

or two adjacent $R_a$ along with the carbon atoms to which they are attached form a dioxole ring;

each $R_b$ is independently F, Cl, —CHF$_2$, and/or —CF$_3$;

y is zero, 1, or 2; and z is zero, 1, or 2.

One embodiment provides at least one compound of Formula (I) wherein $R_2$ is phenyl, fluorophenyl, chlorophenyl, or trifluorophenyl; and $R_3$, $R_a$, $R_b$, y, and z are defined in the first aspect. Included in this embodiment are compounds in which $R_3$ is H or —CH$_3$. Also included in this embodiment are compounds in which $R_3$ is —CH$_2$(cyclopropyl). Further, included in this embodiment are compounds in which $R_3$ is pyridinyl, chloropyridinyl, or methoxypyridinyl.

One embodiment provides at least one compound of Formula (I) wherein $R_2$ is methylisoxazolyl; and $R_3$, $R_a$, $R_b$, y, and z are defined in the first aspect. Included in this embodiment are compounds in which $R_3$ is H or —CH$_3$. Also included in this embodiment are compounds in which $R_3$ is —CH$_2$(cyclopropyl). Further, included in this embodiment are compounds in which $R_3$ is pyridinyl, chloropyridinyl, or methoxypyridinyl.

One embodiment provides at least one compound of Formula (I) wherein $R_2$ is pyridinyl; and $R_3$, $R_a$, $R_b$, y, and z are defined in the first aspect. Included in this embodiment are compounds in which $R_3$ is H or —CH$_3$. Also included in this embodiment are compounds in which $R_3$ is —CH$_2$(cyclopropyl). Further, included in this embodiment are compounds in which $R_3$ is pyridinyl, chloropyridinyl, or methoxypyridinyl.

One embodiment provides at least one compound of Formula (I) wherein $R_2$ is phenyl and $R_3$, $R_a$, $R_b$, y, and z are defined in the first aspect. Included in this embodiment are compounds in which $R_3$ is H or —CH$_3$.

One embodiment provides at least one compound of Formula (I) having the structure:

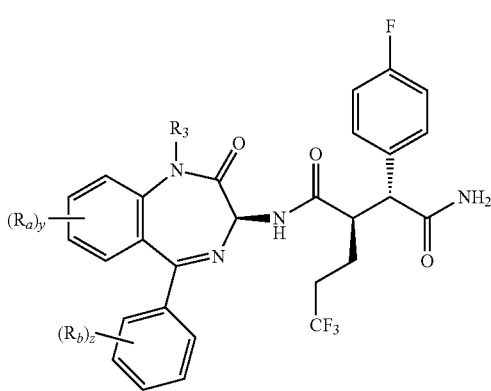

wherein $R_3$, $R_a$, $R_b$, y, and z are defined in the first aspect. Included in this embodiment are compounds in which $R_3$ is H or —CH$_3$.

One embodiment provides at least one compound of Formula (I) having the structure:

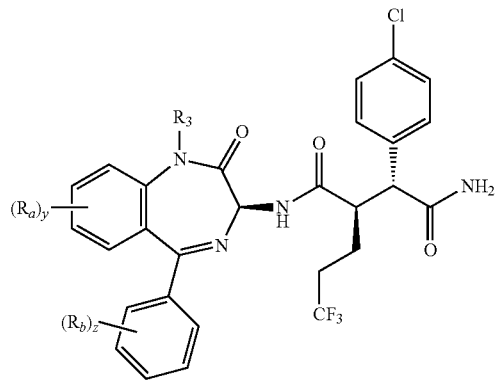

wherein $R_3$, $R_a$, $R_b$, y, and z are defined in the first aspect. Included in this embodiment are compounds in which $R_3$ is H or —CH$_3$.

One embodiment provides at least one compound of Formula (I) having the structure:

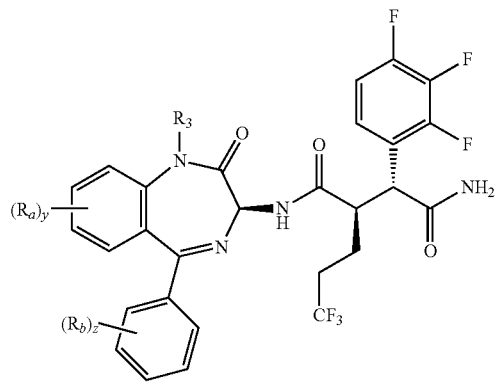

wherein $R_3$, $R_a$, $R_b$, y, and z are defined in the first aspect. Included in this embodiment are compounds in which $R_3$ is H or —CH$_3$.

One embodiment provides at least one compound of Formula (I) having the structure:

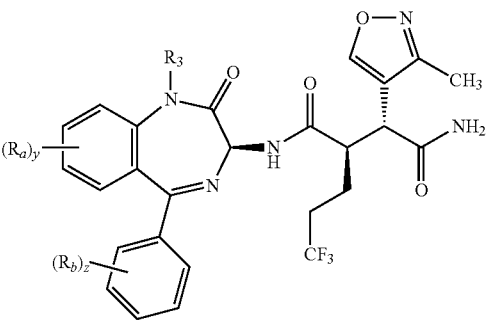

wherein $R_3$, $R_a$, $R_b$, y, and z are defined in the first aspect. Included in this embodiment are compounds in which $R_3$ is H or —CH$_3$.

One embodiment provides at least one compound of Formula (I) having the structure:

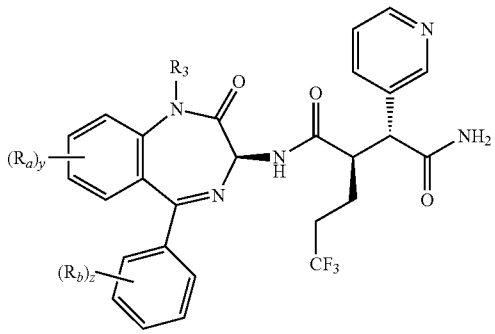

wherein $R_3$, $R_a$, $R_b$, y, and z are defined in the first aspect. Included in this embodiment are compounds in which $R_3$ is H or —$CH_3$.

One embodiment provides at least one compound of Formula (I) having the structure:

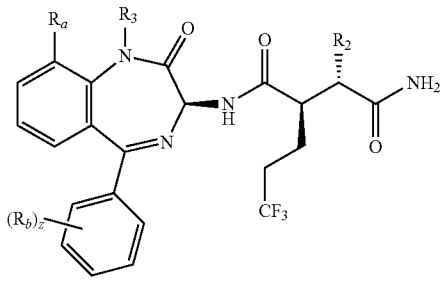

wherein $R_2$, $R_3$, $R_a$, $R_b$, and z are defined in the first aspect. Included in this embodiment are compounds in which $R_3$ is H or —$CH_3$.

One embodiment provides at least one compound of Formula (I) having the structure:

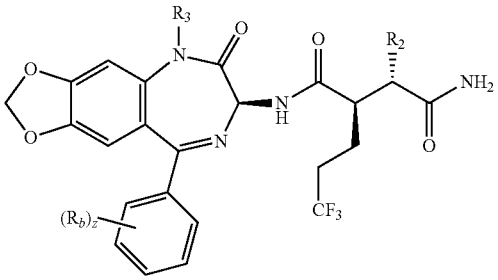

wherein $R_2$, $R_3$, $R_b$, and z are defined in the first aspect. Included in this embodiment are compounds in which $R_3$ is H or —$CH_3$.

One embodiment provides a compound of Formula (I) wherein $R_3$ is H; and $R_2$, $R_a$, $R_b$, y, and z are defined in the first aspect. Included in this embodiment are compounds in which $R_3$ is deuterium (D) or tritium (T).

One embodiment provides a compound of Formula (I) wherein $R_3$ is —$CH_3$; and $R_2$, $R_a$, $R_b$, y, and z are defined in the first aspect. $R_3$ includes methyl groups in which one or more hydrogen atoms are isotopically substituted with deuterium (D) and/or tritium (T). In one example of this embodiment, $R_3$ is —$CD_3$.

One embodiment provides a compound of Formula (I) selected from: (2R,3R)—N-((3S)-1-methyl-2-oxo-5-phenyl-2,3-dihydro-1H-1,4-benzodiazepin-3-yl)-3-phenyl-2-(3,3,3-trifluoropropyl)succinamide (1); (2R,3R)-3-(4-fluorophenyl)-N-((3S)-1-methyl-2-oxo-5-phenyl-2,3-dihydro-1H-1,4-benzodiazepin-3-yl)-2-(3,3,3-trifluoropropyl)succinamide (2); (2R,3R)—N-((3S)-1-methyl-2-oxo-5-phenyl-2,3-dihydro-1H-1,4-benzodiazepin-3-yl)-3-(2,3,4-trifluorophenyl)-2-(3,3,3-trifluoropropyl)succinamide (3); (2R,3R)—N-((3S)-2-oxo-5-phenyl-2,3-dihydro-1H-1,4-benzodiazepin-3-yl)-3-phenyl-2-(3,3,3-trifluoropropyl)succinamide (4); (2R,3R)—N1-((S)-5-(3-fluorophenyl)-9-methyl-2-oxo-2,3-dihydro-1H-benzo[e][1,4]diazepin-3-yl)-3-phenyl-2-(3,3,3-trifluoropropyl)succinamide (5); (2R,3R)—N1-((S)-1-methyl-2-oxo-5-phenyl-2,3-dihydro-1H-benzo[e][1,4]diazepin-3-yl)-3-(3-methylisoxazol-4-yl)-2-(3,3,3-trifluoropropyl)succinamide (6); (2R,3R)—N1-((S)-1-(cyclopropylmethyl)-2-oxo-5-phenyl-2,3-dihydro-1H-benzo[e][1,4]diazepin-3-yl)-3-phenyl-2-(3,3,3-trifluoropropyl)succinamide (7); (2R,3R)—N1-((S)-1-(cyclopropylmethyl)-2-oxo-5-phenyl-2,3-dihydro-1H-benzo[e][1,4]diazepin-3-yl)-3-(4-fluorophenyl)-2-(3,3,3-trifluoropropyl)succinamide (8); (2R,3R)-3-(3-methylisoxazol-4-yl)-N1-((S)-2-oxo-5-phenyl-2,3-dihydro-1H-benzo[e][1,4]diazepin-3-yl)-2-(3,3,3-trifluoropropyl)succinamide (9); (2R,3R)—N1-((S)-2-oxo-5-phenyl-2,3-dihydro-1H-benzo[e][1,4]diazepin-3-yl)-3-(pyridin-3-yl)-2-(3,3,3-trifluoropropyl)succinamide (10); (2R,3R)-3-(3-methyl-4-isoxazolyl)-N-((3S)-2-oxo-5-phenyl-1-(2-pyridinyl)-2,3-dihydro-1H-1,4-benzodiazepin-3-yl)-2-(3,3,3-trifluoropropyl)succinamide (11); (2R,3R)—N-((3S)-2-oxo-5-phenyl-1-(2-pyridinyl)-2,3-dihydro-1H-1,4-benzodiazepin-3-yl)-3-phenyl-2-(3,3,3-trifluoropropyl)succinamide (12); (2R,3R)-3-(3-methyl-4-isoxazolyl)-N-((7S)-6-oxo-9-phenyl-6,7-dihydro-5H-[1,3]dioxolo[4,5-h][1,4]benzodiazepin-7-yl)-2-(3,3,3-trifluoropropyl)succinamide (13); (2R,3R)—N-((3S)-1-(5-methoxy-2-pyridinyl)-2-oxo-5-phenyl-2,3-dihydro-1H-1,4-benzodiazepin-3-yl)-3-(3-methyl-4-isoxazolyl)-2-(3,3,3-trifluoropropyl)succinamide (14); (2R,3R)—N-((3S)-1-(5-methoxy-2-pyridinyl)-2-oxo-5-phenyl-2,3-dihydro-1H-1,4-benzodiazepin-3-yl)-3-phenyl-2-(3,3,3-trifluoropropyl)succinamide (15); (2R,3R)—N-((3S)-1-(6-methoxy-2-pyridinyl)-2-oxo-5-phenyl-2,3-dihydro-1H-1,4-benzodiazepin-3-yl)-3-phenyl-2-(3,3,3-trifluoropropyl)succinamide (16); (2R,3R)—N1-((S)-9-chloro-2-oxo-5-phenyl-2,3-dihydro-1H-benzo[e][1,4]diazepin-3-yl)-3-(3-methylisoxazol-4-yl)-2-(3,3,3-trifluoropropyl)succinamide (17); (2R,3R)—N1-((S)-9-fluoro-2-oxo-5-phenyl-2,3-dihydro-1H-benzo[e][1,4]diazepin-3-yl)-3-(3-methylisoxazol-4-yl)-2-(3,3,3-trifluoropropyl)succinamide (18); (2R,3R)—N1-((S)-9-fluoro-2-oxo-5-phenyl-2,3-dihydro-1H-benzo[e][1,4]diazepin-3-yl)-3-phenyl-2-(3,3,3-trifluoropropyl)succinamide (19); (2R,3R)—N1-((S)-9-methoxy-2-oxo-5-phenyl-2,3-dihydro-1H-benzo[e][1,4]diazepin-3-yl)-3-(3-methylisoxazol-4-yl)-2-(3,3,3-trifluoropropyl)succinamide (20); (2R,3R)—N1-((S)-9-methoxy-2-oxo-5-phenyl-2,3-dihydro-1H-benzo[e][1,4]diazepin-3-yl)-3phenyl-2-(3,3,3-trifluoropropyl)succinamide (21); (2R,3R)—N-((3S)-1-(5-chloro-2-pyridinyl)-2-oxo-5-phenyl-2,3-dihydro-1H-1,4-benzodiazepin-3-yl)-3-phenyl-2-(3,3,3-trifluoropropyl)succinamide (22); (2R,3R)—N-((3S)-1-(5-chloro-2-pyridinyl)-2-oxo-5-phenyl-2,3-dihydro-1H-1,4-benzodiazepin-3-yl)-3-(3-methyl-4-isoxazolyl)-2-(3,3,3- trifluoropropyl)succinamide (23); (2R,3R)—N1-((S)-9-chloro-2-oxo-5-phenyl-2,3-dihydro-1H-benzo[e][1,4]diazepin-3-yl)-3-phenyl-2-(3,3,3-trifluoropropyl)succinamide (24); (2R,3R)—N1-((S)-7-cyano-9-methoxy-2-oxo-5-phenyl-2,3-dihydro-1H-benzo[e][1,4]diazepin-3-yl)-3-phenyl-2-(3,3,3-trifluoropropyl)succinamide (25); (2R,3R)—N1-((S)-9-cyclopropoxy-2-oxo-5-phenyl-2,3-dihydro-1H-benzo[e][1,4]diazepin-3-yl)-3-phenyl-2-(3,3,3-trifluoropropyl)succinamide (26); (2R,3R)—N1-((S)-5-(4-fluorophenyl)-9-methyl-2-oxo-2,3-dihydro-1H-benzo[e][1,4]diazepin-3-yl)-3-phenyl-2-(3,3,3-trifluoropropyl) succinamide (27); (2R,3R)—N1-((S)-9-methyl-2-oxo-5-(3-(trifluoromethyl)phenyl)-2,3-dihydro-1H-benzo[e][1,4]diazepin-3-yl)-3-(3-methylisoxazol-4-yl)-2-(3,3,3-trifluoropropyl)succinamide (28); (2R,3R)—N1-((S)-9-methyl-2-oxo-5-(3-(trifluoromethyl)phenyl)-2,3-dihydro-1H-benzo[e][1,4]diazepin-3-yl)-3-phenyl-2-(3,3,3-trifluoropropyl)succinamide (29); (2R,3R)—N1-((S)-9-methyl-2-oxo-5-phenyl-2,3-dihydro-1H-benzo[e][1,4]diazepin-3-yl)-3-phenyl-2-(3,3,3-trifluoropropyl) succinamide (30); (2R,3R)—N1-((S)-5-(3-chlorophenyl)-9-methyl-2-oxo-2,3-dihydro-1H-benzo[e][1,4]diazepin-3-yl)-3-phenyl-2-(3,3,3-trifluoropropyl)succinamide (31); (2R,3R)—N1-((S)-5-(3-chlorophenyl)-9-methyl-2-oxo-2,3-dihydro-1H-benzo[e][1,4]diazepin-3-yl)-3-(3-methylisoxazol-4-yl)-2-(3,3,3-trifluoropropyl)succinamide (32); (2R,3R)—N1-((S)-5-(4-fluorophenyl)-9-methyl-2-oxo-2,3-dihydro-1H-benzo[e][1,4]diazepin-3-yl)-3-(3-methylisoxazol-4-yl)-2-(3,3,3-trifluoropropyl)succinamide (33); (2R,3R)—N1-((S)-5-(3-(difluoromethyl)phenyl)-9-methyl-2-oxo-2,3-dihydro-1H-benzo[e][1,4]diazepin-3-yl)-3-phenyl-2-(3,3,3-trifluoropropyl)succinamide (34); (2R,3R)—N1-((S)-9-cyclopropoxy-5-(3-fluorophenyl)-2-oxo-2,3-dihydro-1H-benzo[e][1,4]diazepin-3-yl)-3-phenyl-2-(3,3,3-trifluoropropyl)succinamide (35); and (2R,3R)-3-(4-chlorophenyl)-N1-((S)-9-methoxy-2-oxo-5-phenyl-2,3-dihydro-1H-benzo[e][1,4]diazepin-3-yl)-2-(3,3,3-trifluoropropyl)succinamide (36).

One embodiment provides at least one compound of Formula (I) having a metabolic half life value of at least 45 minutes as measured in the human metabolic stability half-life assay described herein.

One embodiment provides at least one compound of Formula (I) having a metabolic half life value of at least 60 minutes as measured in the human metabolic stability half-life assay described herein.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

The term "alkyl" as used herein, refers to both branched and straight chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Any compound that can be converted in vivo to provide the bioactive agent (i.e., the compound of Formula (I)) is a prodrug within the scope and spirit of the invention.

Various forms of prodrugs are well known in the art and are described in:
a) Wermuth, C. G. et al., *The Practice of Medicinal Chemistry*, Chapter 31, Academic Press (1996);
b) Bundgaard, H. ed., *Design of Prodrugs*, Elsevier (1985);
c) Bundgaard, H., Chapter 5, "Design and Application of Prodrugs", Krogsgaard-Larsen, P. et al., eds., *A Textbook of Drug Design and Development*, pp. 113-191, Harwood Academic Publishers (1991); and
d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to a NOTCH receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) thereof can be administered by any means suitable for the condition to be treated, which can depend on the need for site-specific treatment or quantity of Formula (I) compound to be delivered.

Also embraced within this invention is a class of pharmaceutical compositions comprising at least one compound of Formula (I); and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise the compound of Formula (I), and optionally an additional agent selected from any pharmaceutically acceptable carrier, adjuvant, and vehicle. Alternate compositions of this invention comprise a compound of the Formula (I) described herein, and a pharmaceutically acceptable carrier, adjuvant, or vehicle.

Utility

The compounds of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

In one embodiment, a method is provided for treating cancer comprising administering to a mammal in need thereof a compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this embodiment is used to treat breast cancer, colon cancer, or pancreatic cancer. Preferably, the mammal is a human. For example, a therapeutically effective amount for treating cancer may be administered in the method of the present embodiment.

In one embodiment, a method is provided for treating cancer comprising administering to a mammal in need thereof one or more compounds of Formula (I) wherein said cancer is colorectal cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof one or more compounds of Formula (I) wherein said cancer is triple negative breast cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof one or more compounds of Formula (I) wherein said cancer is non-small cell lung cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof one or more compounds of Formula (I) wherein said cancer is pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof one or more compounds of Formula (I) wherein said cancer is ovarian cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof one or more compounds of Formula (I) wherein said cancer is melanoma. Preferably, the mammal is a human. For example, a therapeutically effective amount for treating cancer may be administered in the method of the present embodiment. Routes of administration in the present embodiment include parenteral administration and oral administration.

In one embodiment, the use of one or more compounds of Formula (I) in the manufacture of a medicament for the treatment of cancer is provided. Preferably, in the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Suitable medicaments of the present embodiment include medicaments for parenteral administration, such as, for example, solutions and suspensions and medicaments for oral administration, such as, for example, tablets, capsules, solutions, and suspensions.

One embodiment one or more compounds of Formula (I) for use in therapy in treating cancer. In the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In one embodiment, a method is provided for treating cancer in a mammal wherein the cancer is dependent upon Notch activation, comprising administering to the patient one or more compounds of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Preferably, the method of this embodiment is used to treat breast cancer, colon cancer, or pancreatic cancer. Preferably, the mammal is a human. For example, a therapeutically effective amount for treating cancer may be administered in the method of the present embodiment. Suitable routes of administration include parenteral administration and oral administration.

In treating cancer, a combination of chemotherapeutic agents and/or other treatments (e.g., radiation therapy) is often advantageous. The second (or third) agent may have the same or different mechanism of action than the primary therapeutic agent. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof one or more compounds of Formula (I); and administering one or more additional anticancer agents.

The phrase "additional anticancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of one or more compounds of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of one or more compounds of Formula (I); and one or more additional agents in kit form, e.g., where they are packaged together or placed in separate packages to be sold together as a kit, or where they are packaged to be formulated together.

In one embodiment, a method is provided for treating cancer comprising administering to a mammal in need thereof one or more compounds of Formula (I); administering dasatinib; and optionally, one or more additional anticancer agents.

In one embodiment, a method is provided for treating cancer comprising administering to a mammal in need thereof one or more compounds of Formula (I); administering paclitaxel; and optionally, one or more additional anticancer agents.

In one embodiment, a method is provided for treating cancer comprising administering to a mammal in need thereof one or more compounds of Formula (I); administering tamoxifen; and optionally, one or more additional anticancer agents.

In one embodiment, a method is provided for treating cancer comprising administering to a mammal in need thereof one or more compounds of Formula (I); administering a glucocorticoid; and optionally, one or more additional anticancer agents. An example of a suitable glucocorticoid is dexamethasone.

In one embodiment, a method is provided for treating cancer comprising administering to a mammal in need thereof one or more compounds of Formula (I); administering carboplatin; and optionally, one or more additional anticancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising one or more compounds of Formula (I); one or more additional agents selected from a kinase inhibitory agent (small molecule, polypeptide, and antibody), an immunosuppressant, an anticancer agent, an anti-viral agent, anti-inflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

The administration can be continuous, i.e., every day, or intermittently. The terms "intermittent" or "intermittently" as used herein mean stopping and starting at either regular or irregular intervals. For example, intermittent administration includes administration one to six days per week; administration in cycles (e.g., daily administration for two to eight consecutive weeks followed by a rest period with no administration for up to one week); or administration on alternate days.

In one embodiment, the one or more compounds of Formula (I) are administered continuously to a patient in need thereof, one or more times daily. For example, a therapeutically effective amount of the compound of Formula (I) is administered to a patient in need thereof, one or more times daily for continuous days.

In one embodiment, the one or more compounds of Formula (I) are administered intermittently to a patient in need thereof, one or more times daily. For example, a therapeutically effective amount of the compound of Formula (I) is administered to a patient in need thereof, one or more times daily according to an intermittent schedule.

In one embodiment, the one or more compounds of Formula (I) are administered to a patient in need thereof, one or more times daily for continuous days followed by one or more days without administration. Preferably, a therapeutically effective amount of the compound of Formula (I) is administered. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, the one or more compounds of Formula (I) are administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, at least one compound of Formula (I) is administered on one day, followed by 6 days of rest, and repeated on a weekly schedule.

In one embodiment, at least one compound of Formula (I) is administered on one day, followed by 6 days of rest, and repeated on a weekly schedule for 1 to 4 weeks, and then followed by one week or rest. For example, the compound of Formula (I) is administered on one day, followed by 6 days of rest for three weeks, and then followed by one week of rest. This four week cycle can be repeated one or more times.

In one embodiment, at least one compound of Formula (I) is administered on two consecutive days, followed by 5 days of rest, and repeated on a weekly schedule.

In one embodiment, at least one compound of Formula (I) is administered on three consecutive days followed by four days of rest, and repeated on a weekly schedule.

In one embodiment, at least one compound of Formula (I) is administered on one day, followed by 10 to 13 days of rest.

In one embodiment, at least one compound of Formula (I) is administered once each day (QD). This embodiment includes once daily oral administration.

In one embodiment, at least one compound of Formula (I) is administered twice each day (BID). This embodiment includes twice daily oral administration.

In one embodiment, at least one compound of Formula (I) is administered on alternate days: one day on followed by one day of rest. This two day cycle can be repeated one or more times.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 4.

-continued

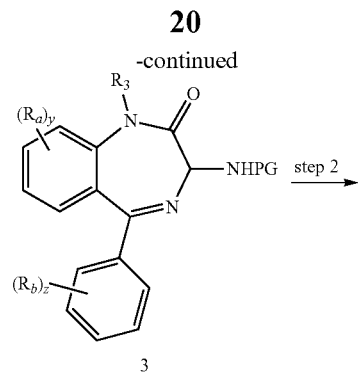

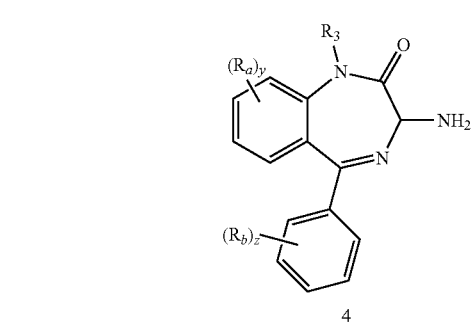

Step 1: The preparation of benzodiazepinone (4) may be accomplished in multitude of methods known to one skilled in the art. For example, an appropriate 2-aminobenzophenone (1) (for example, from Walsh, D. A., *Synthesis*, 677 (1980); and references cited therein) may be coupled to the protected glycine derivative (2) (PG=protecting group, for example PG=CBz, see Katritzky, A. R., *J. Org. Chem.*, 55:2206-2214 (1990)), treated with a reagent such as ammonia and cyclized to afford (3), according to the procedure outlined in the literature (for example Sherrill, R. G. et al., *J. Org. Chem.*, 60:730 (1995); or other routes known to one skilled in the art). The resulting racemic mixture may be separated by standard methods, such as preparative chiral chromatography. Also, if $R_3$=H, (3) may be treated with a reagent such as MeI and a base such as $K_2CO_3$ in a solvent such as DMF to prepare (3) with $R_3$=Me.

Step 2: The deprotection of either compound (3) may be accomplished in several ways known to one skilled in the art. For example, with PG=CBz, (3) may be treated with a reagent such as HBr in a solvent such as AcOH. If (3) is racemic, then (3) could be used as is, or the enantiomers separated, and each used subsequently.

Scheme 1

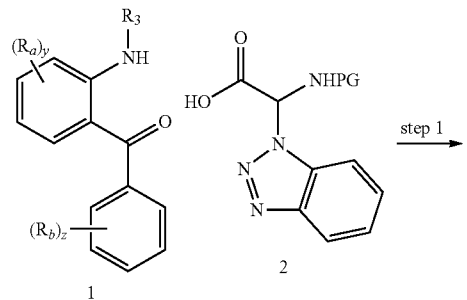

Scheme 2

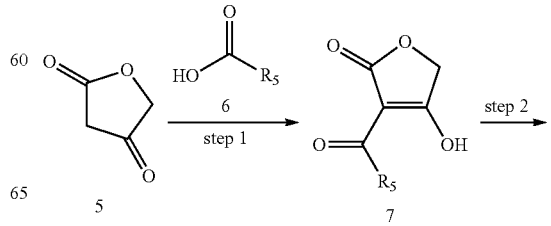

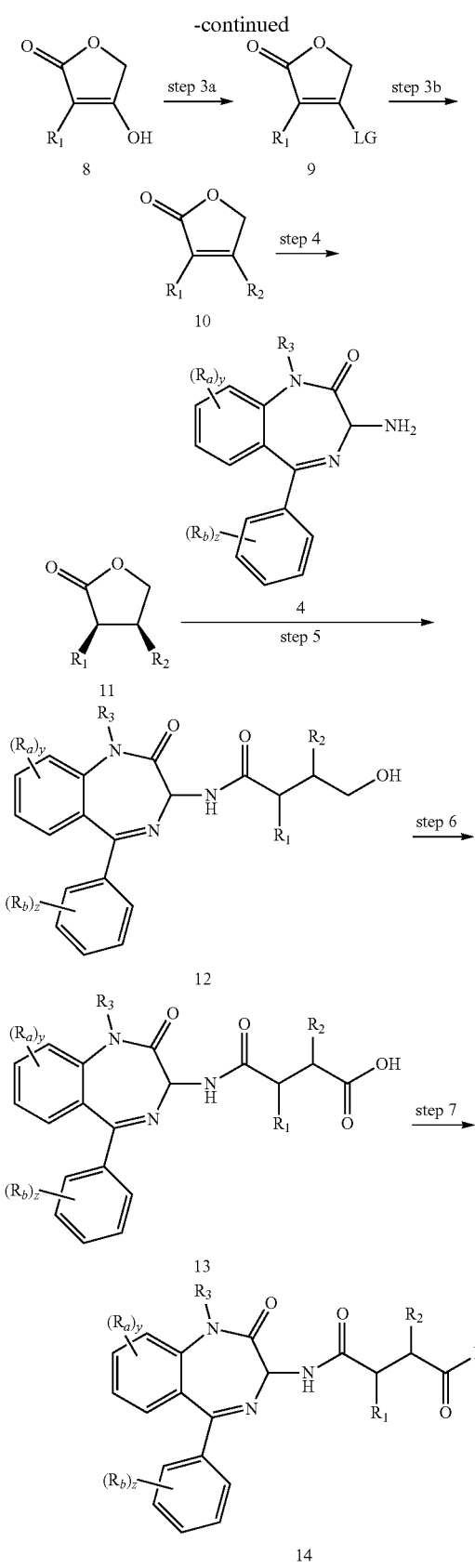

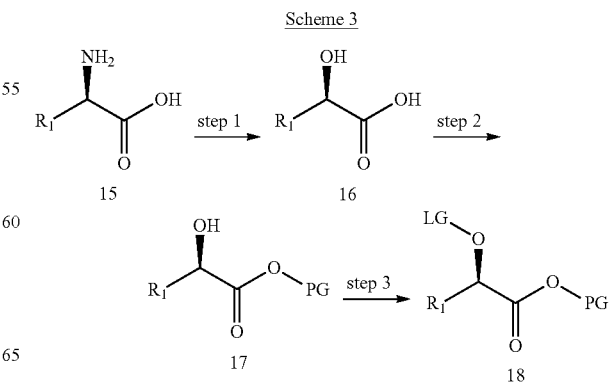

carbodiimide such as DCC, a base such as TEA, and a catalyst such as DMAP in a solvent such as DCM to provide Compound (7).

Step 2: Conversion of Compound (7) to Compound (8) may be accomplished by treatment with a reagent such as sodium cyanoborohydride in the presence of an acid such as HCl under atmospheric conditions that may be inert, for example under $N_2$.

Step 3: Conversion of Compound (8) to Compound (9) may proceed via Compound (9) bearing an appropriate leaving group (LG). For example, treatment of Compound (8) with a base such as 2,6-lutidine and a reagent such as trifluoromethanesulfonic anhydride in a solvent such as DCM at an appropriate temperature such as −78° C., provides the triflate of Compound (9). Compound (9) may now be subjected to cross coupling reaction conditions to provide Compound (10). For example, treatment of Compound (9) with an appropriately substituted coupling partner, for example a boronic acid, in the presence of a catalyst such as tetrakis(triphenylphosphine)palladium(0), a base such as potassium phosphate in a solvent such as dioxane under atmospheric conditions that may be inert, for example under $N_2$, provides Compound (10).

Step 4: Conversion of Compound (10) to Compound (11) may be accomplished via standard procedures known to one skilled in the art. For example, treatment of Compound (10) under hydrogen atmosphere in the presence of a catalyst such as Pd/C in a solvent such as methanol gives Compound (11).

Step 5: Compound (12) may be obtained by the coupling of Compound (11) with Compound (4). For example, the transformation may be accomplished with the use of a reagent such as $AlMe_3$ in a solvent such as DCM under an inert atmosphere such as $N_2$. At this instance, the mixture of diastereomers obtained may be used as a mixture or may be separated by an appropriate method such as chiral chromatography.

Step 6: Compound (12) is oxidized using an oxidizing agent such as Jones reagent, in a solvent such as acetone to give Compound (13). If the compound is a diastereomeric mixture then it may be used as a mixture or may be separated using an appropriate method such as chiral chromatography.

Step 7: Conversion of Compound (13) to Compound (14) may be accomplished via standard procedures known to one skilled in the art. For example, coupling of Compound (13) with an appropriate amine source such as ammonium chloride, a carbodiimide such as EDC, HOBT and a base such as TEA in a solvent such as DMF provides Compound (14). If necessary, the diastereomeric mixture can be separated using an appropriate separation technique, such as chiral chromatography.

Step 1: The first step of Scheme 2 involves the treatment of Compound (5) with carboxylic acid (6) in the presence of a

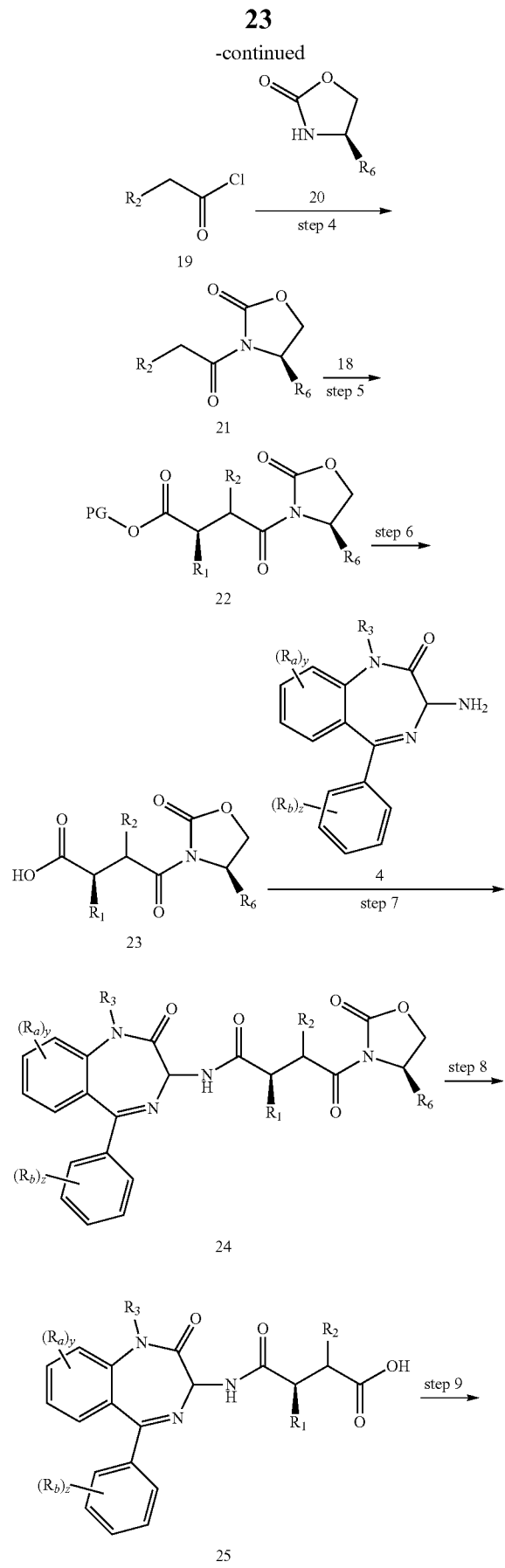

Step 1: The first step of Scheme 3 is accomplished by treating Compound (15) with a reagent such as sodium nitrite in an acid such as $H_2SO_4$ and a solvent such as water to provide Compound (16).

Step 2: The acid group of Compound (16) is protected with a protecting group to give Compound (17), a strategy known to one skilled in the art. For example, the reaction may be performed using an alcohol such as benzyl alcohol in a solvent such as toluene and an acid such as $H_2SO_4$ to provide Compound (17).

Step 3: Compound (18) bearing a suitable leaving group may be prepared by treatment of Compound (17) with a base such as 2,6-lutidine and a reagent such as trifluoromethanesulfonic anhydride in a solvent such as DCM at an appropriate temperature.

Step 4: Compound (19) can be converted to Compound (21) in multiple ways known to one skilled in the art. For example, treatment of acid chloride (19), either prepared from the corresponding carboxylic acid with a reagent such as oxalyl chloride in a solvent such as DCM, or obtained commercially, can be treated with an oxazolidinone (20) under standard conditions to give Compound (21) (Evans, D. A. et al., J. Am. Chem. Soc., 112:4011 (1990)).

Step 5: The preparation of Compound (22) may be effected by treating Compound (21) with a base such as LiHMDS in a solvent such as THF at an appropriate temperature such as −78° C., followed by the addition of a solution of Compound (18) in a solvent such as THF.

Step 6: The protecting group of Compound (22) may be removed via many methods known to one skilled in the art. For example, a benzyl group may be removed by subjecting it to hydrogenation conditions using a palladium catalyst such as Pearlman's Catalyst in a solvent such as methanol to provide Compound (23).

Step 7: Compound (4) may be coupled with Compound (23) in the presence of a coupling reagent such as TBTU and a base such as TEA in a solvent such as DMF to provide Compound (24). The diastereomers may be separated using an appropriate method such as chiral chromatography.

Step 8: Hydrolysis of Compound (24) may be accomplished by treating it with hydrogen peroxide and lithium hydroxide at an appropriate temperature using a mixture of solvents such as THF/water to give Compound (25).

Step 9: Conversion of Compound (25) to Compound (26) may be accomplished via standard procedures known to one skilled in the art. For example, coupling of Compound (25) with an appropriate amine source such as ammonium chloride, a carbodiimide such as EDC, HOBT and a base such as TEA in a solvent such as DMF provides Compound (26). If necessary, the diastereomeric mixture can be separated using an appropriate separation technique, such as chiral chromatography.

Scheme 4

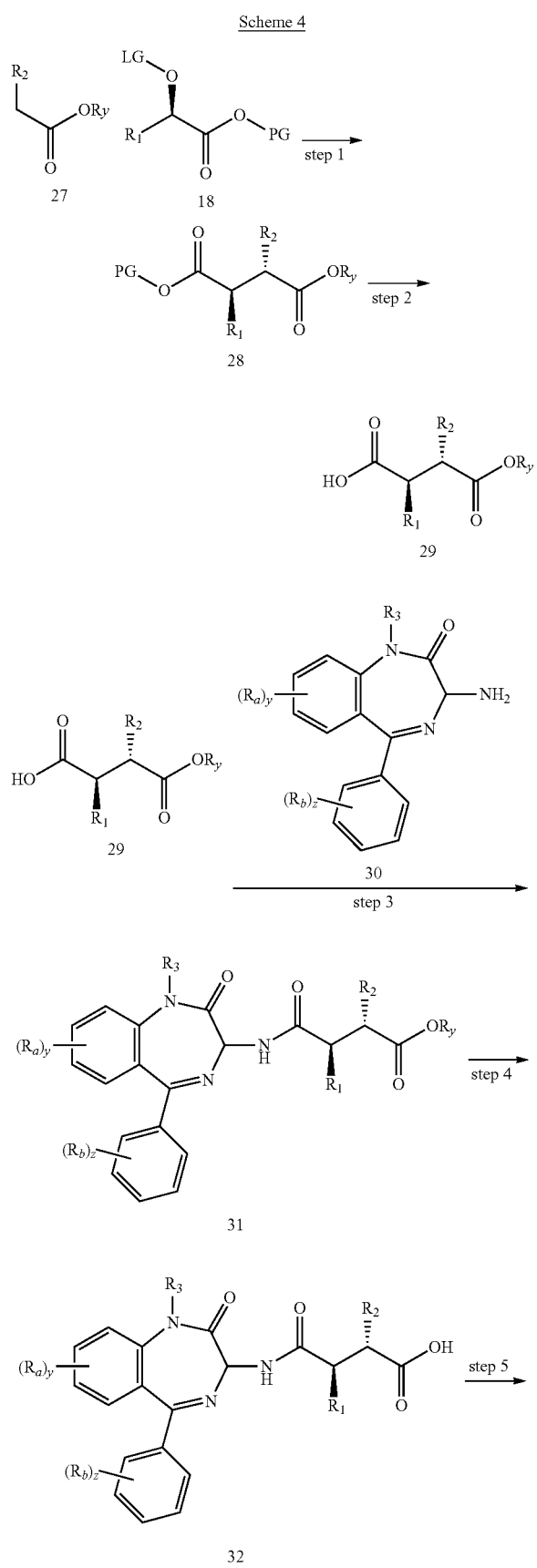

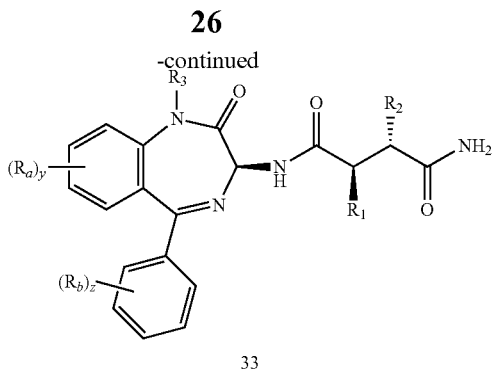

Step 1: A suitably protected acid (27) may be alkylated with compound (18) having a suitable leaving group, such as a triflate, in the presence of a base such as KHMDS to give compound (28) as the predominant diastereomer. Compound (28) could be used as a diastereomeric mixture or can be separated using an appropriate separation technique, such as chiral preparative chromatography, to give the pure diastereomer compound.

Step 2: The protecting group of Compound (28) may be removed via many methods known to one skilled in the art. For example, a benzyl group may be removed by subjecting it to hydrogenation conditions using a palladium catalyst in a solvent such as methanol to provide Compound (29).

Step 3: Benzodiazepinone (30) may be coupled to compound (29) either as a pure diastereomer or as a diastereomeric mixture in the presence of a coupling reagent such as TBTU and a base such as TEA, in a solvent such as DMF to provide compound (31) as either a diastereomerically pure compound or as a mixture of diastereoisomers, as appropriate. This mixture may be used as such in the subsequent step, or if desired, may be purified using an appropriate separation technique, such as chiral preparative chromatography to provide the diastereomerically pure compounds.

Step 4: Treatment of compound (31) with an acid such as TFA at an appropriate temperature such as 25° C., in a solvent such as DCM provides compound (32) as either a diastereomerically pure compound or as a mixture of diastereoisomers. This mixture may be used as such in the subsequent step, or if desired, may be purified using an appropriate separation technique, such as chiral preparative chromatography to provide the diastereomerically pure compounds.

Step 5: Conversion of compound (32) to compound (33) may be accomplished via coupling of compound (32) with an appropriate amine source such as ammonia, a carbodiimide such as EDC with HOBT in a solvent such as THF. If necessary the diastereomeric mixture can be separated using an appropriate separation technique, such as chiral preparative chromatography.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

ABBREVIATIONS

ACN acetonitrile
AcOH acetic acid
AlMe$_3$ trimethyl aluminum
Boc tert-butyloxycarbonyl
CBz benzyloxycarbonyl
DBU 1,8-diazabicyclo[5.4.0]undec-7-ene
DCC 1,3-dicyclohexylcarbodiimide
DCM dichloromethane
DEA diethylamine
DMAP dimethylaminopyridine
DME dimethyl ether
DMF dimethylformamide
DMSO dimethyl sulfoxide
EDC 1-(3-dimethylaminopropyl)-3-ethylcarbodiimide hydrochloride
Et$_2$O diethyl ether
EtOAc ethyl acetate
Et$_2$AlCl diethyl aluminum chloride
Et$_3$N triethyl amine
H$_2$SO$_4$ sulfuric acid
HCl hydrochloric acid
HOBT hydroxybenzotriazole
HPLC High Performance Liquid Chromatography
hr hour(s)
IPA isopropyl alcohol
iPrOH isopropyl alcohol
KHMDS potassium bis(trimethylsilyl)amide
LCMS Liquid Chromatography-Mass Spectroscopy
LDA lithium diisopropylamide
LiHMDS lithium bis(trimethylsilyl)amide
Me methyl
MeOH methanol
min minute(s)
MTBE methyl tert-butyl ether
N$_2$ nitrogen
NaHMDS sodium bis(trimethylsilyl)amide
n-BuLi n-butyl lithium
Pd/C palladium on carbon
Pd(Ph$_3$P)$_4$ tetrakis(triphenylphosphine) palladium(0)
Ph phenyl
RT retention time
sat saturated
TBTU O-(1H-benzotriazol-1-yl)-N,N,N',N'-tetramethyluronium tetrafluoroborate
TEA triethylamine
TFA trifluoroacetic acid
THF tetrahydrofuran
TMSCl chlorotrimethylsilane

Example 1

(2R,3R)—N-((3S)-1-Methyl-2-oxo-5-phenyl-2,3-dihydro-1H-1,4-benzodiazepin-3-yl)-3-phenyl-2-(3,3,3-trifluoropropyl)succinamide

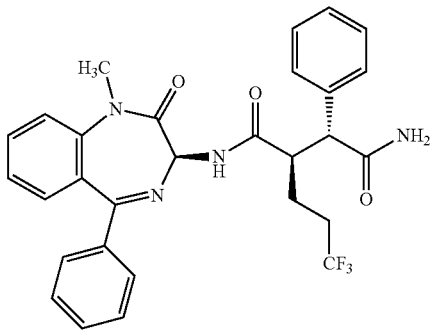

(1)

Preparation 1A: 4-Hydroxy-3-(3,3,3-trifluoropropanoyl)furan-2(5H)-one

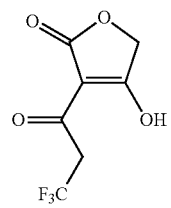

(1A)

To a cool (0° C.), stirred suspension of furan-2,4(3H,5H)-dione (16.46 g, 164 mmol) in DCM (650 mL) was added TEA (23.0 mL, 165 mmol), DMAP (6.04 g, 49.4 mmol), 3,3,3-trifluoropropanoic acid (16.0 mL, 181 mmol) and DCC (40.70 g, 197 mmol) resulting in a yellow homogenous solution. The solution was stirred at 0° C., and then was allowed to warm to room temperature as the bath warmed while stirring overnight. The suspension was filtered and the solid was washed with DCM. The deep red filtrate was concentrated under reduced pressure. The residue was partitioned between EtOAc and 1M HCl (400 mL). The organic phase was washed with brine, dried (Na$_2$SO$_4$), filtered and concentrated under reduced pressure to afford an amber solid. This was dissolved in a minimum amount of CH$_3$CN, to which DCM was added to form a precipitate. The suspension was allowed to stand in the freezer overnight. It was sonicated then cooled and filtered, the solid was washed with cold DCM and then dried to provide Preparation 1A (31.62 g, 91%) as a cream solid: $^1$H NMR (400 MHz, DMSO-d$_6$) δ ppm 13.07 (1H, br. s.), 4.29 (2H, s), 3.80 (2H, q, J=11.67 Hz).

Preparation 1B: 4-Hydroxy-3-(3,3,3-trifluoropropyl)furan-2(5H)-one

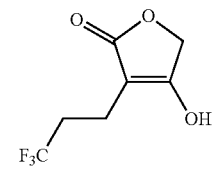

(1B)

A 3-neck flask was equipped with a nitrogen inlet, septum and outlet with the flow through a trap of aqueous $K_2CO_3$. To this flask was added Preparation 1A (13 g, 61.9 mmol) in THF (40 mL) and 2M HCl (40 mL, 80 mmol). To the suspension was added sodium cyanoborohydride (3.89 g, 61.9 mmol) (portion wise every 30 min, 5×). The reaction mixture was stirred at room temperature overnight. 1N HCl (50 mL) was added and more sodium cyanoborohydride (2.4 g, portion wise for every 20 min.). The reaction mixture was stirred for another 30 min. The reaction mixture was diluted with EtOAc and the organic phase was separated and concentrated under reduced pressure to give a yellow solid. The solid was suspended into water, and was stirred for 10 min then collected by filtration and rinsed with water. The solid was dried to give Preparation 1B (11 g, 90%) as light yellow solid: HPLC: RT=1.418 min (YMC S-5 ODS-A 4.6×50 mm eluting with 10-90% aqueous MeOH over 4 minutes containing 0.2% $H_3PO_4$, 4 mL/min, monitoring at 220 nm); $^1$H NMR (400 MHz, DMSO-$d_6$) δ ppm 2.29-2.40 (m, 4H), 4.60 (s, 2H), 12.16 (s, 1H).

Preparation 1C: 5-Oxo-4-(3,3,3-trifluoropropyl)-2,5-dihydrofuran-3-yl trifluoromethane sulfonate

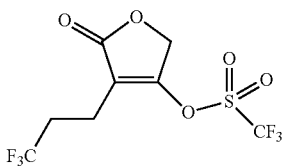

(1C)

To a cold (−78° C.), stirred suspension of Preparation 1B (8.1 g, 41.3 mmol) in DCM (300 mL) was added 2,6-lutidine (7.22 mL, 62.0 mmol) resulting in a homogeneous solution. Trifluoromethanesulfonic anhydride (8.02 mL, 47.5 mmol) was added over 10 min and the reaction mixture was stirred at −78° C. for 30 min. The reaction mixture was poured into a mixture to 1:1 1N HCl and brine. The organic phase was separated and the aqueous phase was extracted with DCM. The combined organics were washed with brine, dried ($Na_2SO_4$), filtered and concentrated under reduced pressure. The crude material was purified by flash chromatography (Teledyne ISCO, 80 g column, 60 mL/min, A: hexane, B: EtOAc. 0-50% in 25 min). Concentration of appropriate fractions provided Preparation 1C (12.5 g, 91%) as a slight yellow liquid which solidified after being stored at −20° C.: HPLC: RT=2.806 min (YMC S-5 ODS-A 4.6×50 mm eluting with 10-90% aqueous MeOH over 4 minutes containing 0.2% $H_3PO_4$, 4 mL/min, monitoring at 220 nm); MS(ES): m/z=329 [M+H]$^+$; $^1$H NMR (400 MHz, CDCl$_3$) δ ppm 4.96 (2H, s.), 2.6 (2H, m), 2.46 (2H, m).

Preparation 1D:
4-Phenyl-3-(3,3,3-trifluoropropyl)furan-2(5H)-one

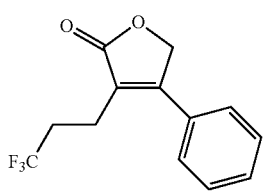

(1D)

Nitrogen was bubbled through a solution of Preparation 1C (4 g, 12.19 mmol) in dioxane (130 mL) for 20 min. To the degassed solution was added phenylboronic acid (2.67 g, 21.94 mmol), potassium phosphate, tribasic (5.17 g, 24.38 mmol) and tetrakis(triphenylphosphine)palladium(0) (0.704 g, 0.609 mmol). The reaction mixture was stirred at 80° C. under nitrogen atmosphere for 12 h. The reaction was judged complete by LCMS. The reaction mixture was filtered. The filtrate was concentrated to give a crude material which was purified by flash chromatography (Teledyne ISCO, 220 g column, 150 mL/min 0-0% B for 5 min, then 0-50% EtOAc/hexane in 25 min). Preparation 1D (3.2 g, 95%) was obtained as a light yellow solid: HPLC: RT=2.713 min (YMC S-5 ODS-A 4.6×50 mm eluting with 10-90% aqueous MeOH over 4 minutes containing 0.2% $H_3PO_4$, 4 mL/min, monitoring at 220 nm); MS(ES): m/z=257 [M+H]$^{30}$; $^1$H NMR (400 MHz, CDCl$_3$) δ 2.40-2.52 (m, 2H) 2.75-2.84 (m, 2H) 5.05 (s, 2H) 7.37 (dd, J=4.89, 1.63 Hz, 2H) 7.39 (s, 1H) 7.50 (d, J=2.01 Hz, 3H) 7.51 (d, J=2.01 Hz, 2H).

Preparation 1E: (3R,4R)-4-Phenyl-3-(3,3,3-trifluoropropyl)dihydrofuran-2(3H)-one

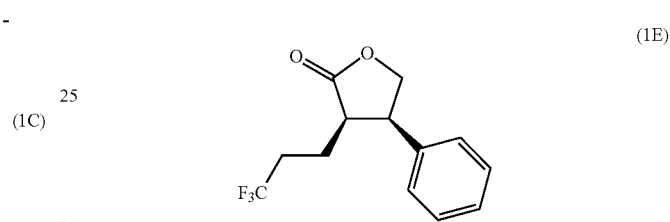

Nitrogen was bubbled through a solution of Preparation 1D (3.1 g, 12.10 mmol) in anhydrous MeOH (100 mL) for 20 min. To the degassed solution was added 10% Pd/C (2 g, 12.10 mmol)). The reaction vessel was evacuated with vacuum and filled with hydrogen. This was repeated twice and the reaction mixture was stirred under hydrogen balloon at room temperature for 15 h. The reaction mixture was evacuated with vacuum, filled with nitrogen then filtered. The filtrate was concentrated to give racemic Preparation 1E (2.8 g, 85%) as a white solid: HPLC: RT=2.650 min (YMC S-5 ODS-A 4.6×50 mm eluting with 10-90% aqueous MeOH over 4 minutes containing 0.2% $H_3PO_4$, 4 mL/min, monitoring at 220 nm); $^1$H NMR (400 MHz, CDCl$_3$) δ 1.30-1.41 (m, 1H) 1.64-1.74 (m, J=14.18, 9.85, 7.72, 6.15 Hz, 1H) 2.06-2.17 (m, J=15.47, 10.20, 9.85, 5.65 Hz, 1H) 2.23-2.35 (m, 1H) 2.89 (q, J=7.78 Hz, 1H) 3.71 (ddd, J=8.16, 6.15, 1.76 Hz, 1H) 4.51 (dd, J=9.41, 1.88 Hz, 1H) 4.57-4.67 (m, 1H) 7.12-7.21 (m, 2H) 7.28-7.39 (m, 3H).

Preparation 1F: (3S)-3-Amino-1-methyl-5-phenyl-1,3-dihydro-2H-1,4-benzodiazepin-2-one

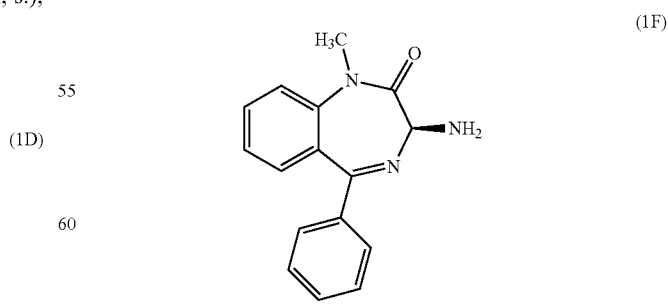

Racemic 3-amino-1-methyl-5-phenyl-1,3-dihydro-2H-1,4-benzodiazepin-2-one (Rittle, K. E. et al., *Tetrahedron Letters*, 28(5):521-522 (1987)) was prepared according to the literature procedure. The enantiomers were separated under chiral-SFC conditions using the following method: CHIRALPAK® AS-H 5×25; Mobile Phase: 30% MeOH+ 0.1% DEA in $CO_2$; Flow rate: 280 mL/min; Pressure: 100 bar; Temperature: 35° C.

Obtained the S-enantiomer (Preparation 1F): HPLC: RT=1.75 min (30% MeOH+ 0.1% DEA in $CO_2$ on CHIRALPAK® AS-H 4.6×250 mm, 3 mL/min, 35° C., 100 bar, 230 nm, 10 μl injection); $^1$H NMR (400 MHz, $CDCl_3$) δ 7.58-7.63 (2H, m), 7.55 (1H, ddd, J=8.50, 7.11, 1.76 Hz), 7.40-7.47 (1H, m), 7.34-7.40 (3H, m), 7.31 (1H, dd, J=7.81, 1.51 Hz), 7.14-7.22 (1H, m), 4.46 (1H, s), 3.44 (3H, s), 3.42 (2H, s); $[α]_D$=−155° (c=1.9, MeOH) (Lit. Rittle, K. E. et al., *Tetrahedron Letters*, 28(5):521-522 (1987)) $[α]_D$=−236°).

Also obtained the R-enantiomer: HPLC: RT=1.71 min; $[α]_D$=+165° (c=2.1, MeOH) (Lit $[α]_D$=+227°).

Preparation 1G: (2R)-5,5,5-Trifluoro-2-((1R)-2-hydroxy-1-phenylethyl)-N-((3S)-1-methyl-2-oxo-5-phenyl-2,3-dihydro-1H-1,4-benzodiazepin-3-yl)pentanamide and (2S)-5,5,5-Trifluoro-2-((1S)-2-hydroxy-1-phenylethyl)-N-((3S)-1-methyl-2-oxo-5-phenyl-2,3-dihydro-1H-1,4-benzodiazepin-3-yl)pentanamide

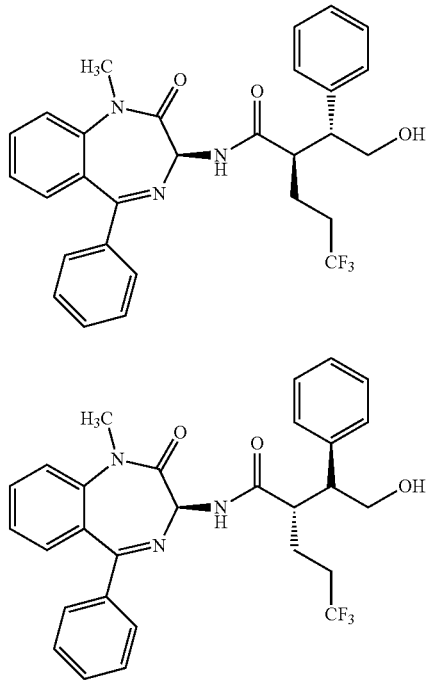

(1G-1)

(1G-2)

To a solution of Preparation 1E (2 g, 7.36 mmol) and Preparation 1F (2.93 g, 11.04 mmol) in DCM (80 mL) at room temperature was added MeOH (0.209 mL, 5.15 mmol) followed by 2M $AlMe_3$ in toluene (14.72 mL, 29.4 mmol). The color of the solution changed to blue, then grey and bubbles evolved. The reaction mixture was then heated at 40° C. under nitrogen for 1 h 15 min. The reaction mixture was cooled to room temperature and diluted with DCM, and then the reaction mixture was slowly added to 20% Na/K tartrate aqueous solution. The organic phase was separated after 30 min, washed with brine, dried ($Na_2SO_4$), filtered and concentrated under reduced pressure. The crude material was purified by flash chromatography (Teledyne ISCO, 120 g column, 85 mL/min 0-60% EtOAc-DCM in 30 min). Preparation 1G (2 g, 51%) was obtained as a mixture of diastereomers Preparation 1G-1 and Preparation 1G-2 (1.7:1): HPLC: RT=3.096 and 3.051 min (YMC S-5 ODS-A 4.6×50 mm eluting with 10-90% aqueous MeOH over 4 minutes containing 0.2% $H_3PO_4$, 4 mL/min, monitoring at 220 nm); MS(ES): m/z=524 $[M+H]^+$; $^1$H NMR (400 MHz, $CDCl_3$) δ 1.82 (m, 1H) 1.95 (m, 1H) 2.2 (m, 2H) 2.96 (m, 1H) 3.22 (m, 1H) 3.45 (d, 3H) 3.97 (m, 1H) 4.13 (m, 1H) 5.43 (m, 1H) 7.21-7.62 (m, 15H).

Preparation 1H: (2R,3R)-6,6,6-Trifluoro-3-(((3S)-1-methyl-2-oxo-5-phenyl-2,3-dihydro-1H-1,4-benzodiazepin-3-yl)carbamoyl)-2-phenylhexanoic acid and (2S,3S)-6,6,6-Trifluoro-3-(((3S)-1-methyl-2-oxo-5-phenyl-2,3-dihydro-1H-1,4-benzodiazepin-3-yl)carbamoyl)-2-phenylhexanoic acid

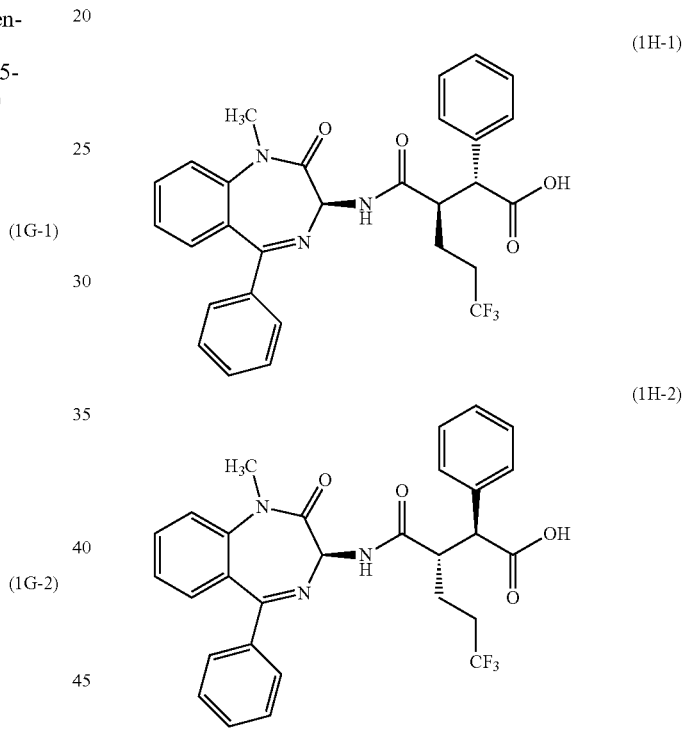

(1H-1)

(1H-2)

To a cool (0° C.), stirred solution of Preparation 1G (2 g, 3.8 mmol) in acetone (20 mL) was added 1.35M Jones reagent ($CrO_3+H_2SO_4+H_2O$) (5.66 mL, 7.64 mmol). The reaction mixture was stirred at 0° C. for 10 min then was stirred at room temperature for 1 h 45 min. The reaction was judged complete by LCMS. The reaction mixture was diluted with EtOAc and 1% $NaHSO_3$. The organic phase was washed with brine, dried ($MgSO_4$), filtered and concentrated under reduced pressure. The crude material was purified by flash chromatography (Teledyne ISCO, 120 g column, 85 mL/min, 0-100% $EtOAc/CH_2Cl_2$ 30 min) to provide Preparation 1H (1.7 g, 81%) as a colorless solid that was a mixture of diastereomers Preparation 1H-1 and Preparation 1H-2 (1.65:1): HPLC: RT=3.078 (YMC S-5 ODS-A 4.6×50 mm eluting with 10-90% aqueous MeOH over 4 minutes containing 0.2% $H_3PO_4$, 4 mL/min, monitoring at 220 nm); MS(ES): m/z=538 $[M+H]^+$; $^1$H NMR (400 MHz, $CDCl_3$) δ 2.0 (m, 2H) 2.3 (m, 2H) 3.3 (m, 1H) 3.4 (s, 3H) 3.9 (m, 1H) 5.24 (d, 1H) 7.16-7.55 (m, 15H).

Example 1

To a solution of Intermediate 1H (1.17 g, 2.0 mmol) in DMF (30 mL) was added EDCI (1.819 g, 9.49 mmol), HOBt (1.453 g, 9.49 mmol), NH$_4$Cl (1.690 g, 31.6 mmol) and Hunig's base (8.29 mL, 47.4 mmol). The reaction mixture was stirred at room temperature for 16 h. Water was added and stirred for 10 min. Precipitate was formed and filtered to collect solid. This solid was then dissolved with CH$_2$Cl$_2$ and washed with brine. The organic phase was dried with MgSO$_4$, filtered, and concentrated and the crude material was purified by flash chromatography (Teledyne ISCO, 120 g column, 85 mL/min, 0-100% EtOAc/hexane) to provide Example 1 (1.1 g) as a colorless solid that was a mixture of diastereomers (1.8:1).

The diastereomeric mixture was separated on Thar preparative SFC: Column: CHIRALCEL® OD-H (5×25 cm, 5 µm); BPR pressure: 100 bars; Temperature: 35° C.; Flow rate: 280 mL/min; Mobile Phase: CO$_2$/MeOH (87/13); Detector wavelength: 225 nm. Example 1: HPLC: RT=8.21 min (30% MeOH+0.1% DEA in CO$_2$ on CHIRALPAK® AS-H 4.6×250 mm, 3 mL/min, 35° C., 100 bar, 230 nm, 10 µl inj); MS(ES): m/z=537 [M+H]+; $^1$H NMR (400 MHz, CDCl$_3$) δ 1.9 (m, 2H) 2.16 (m, 2H) 3.2 (m, 1H) 3.6 (m 3H) 5.21 (d, 1H) 5.35 (bs, 1H) 5.52 (bs 1H) 7.12-7.52 (m, 15H).

Example 2

(2R,3R)-3-(4-Fluorophenyl)-N-((3S)-1-methyl-2-oxo-5-phenyl-2,3-dihydro-1H-1,4-benzodiazepin-3-yl)-2-(3,3,3-trifluoropropyl)succinamide (2)

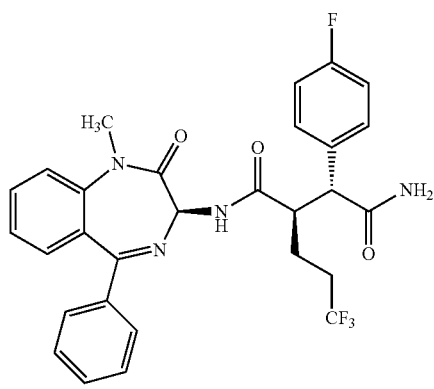

Example 2 was prepared according to the general procedure shown for Example 1. HPLC: RT=24.5 min (H$_2$O/CH$_3$CN with TFA, SunFire C18 3.5 µm, 4.6×150 mm, gradient=30 min, wavelength=220 and 254 nm); MS(ES):m/z=555.3 [M+H$^+$]; $^1$H NMR (400 MHz, chloroform-d) δ 7.57 (td, J=7.8, 1.5 Hz, 1H), 7.53-7.29 (m, 11H), 7.25-7.17 (m, 1H), 7.13-7.03 (m, 2H), 5.59 (br. s., 1H), 5.49 (br. s., 1H), 5.27 (d, J=8.0 Hz, 1H), 3.66 (d, J=9.8 Hz, 1H), 3.42 (s, 3H), 3.32-3.19 (m, 1H), 2.24 (dd, J=16.6, 10.5 Hz, 2H), 2.04-1.91 (m, 2H).

Example 3

(2R,3R)—N-((3S)-1-Methyl-2-oxo-5-phenyl-2,3-dihydro-1H-1,4-benzodiazepin-3-yl)-3-(2,3,4-trifluorophenyl)-2-(3,3,3-trifluoropropyl)succinamide

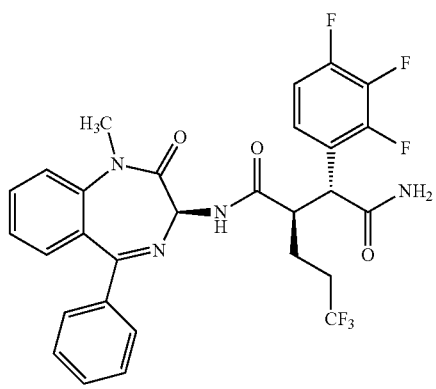 [SMILES: CN1C(=O)[C@@H](NC(=O)[C@H](CCC(F)(F)F)[C@@H](C(N)=O)c2ccc(F)c(F)c2F)N=C(c2ccccc2)c2ccccc21]

Example 3 was prepared according to the general procedure shown for Example 1. HPLC: RT=25.49 min (H$_2$O/CH$_3$CN with TFA, SunFire C18 3.5 µm, 4.6×150 mm, gradient=30 min, wavelength=220 and 254 nm); MS(ES):m/z=591.4 [M+H$^+$]; $^1$H NMR (400 MHz, chloroform-d) δ 7.65-7.54 (m, 2H), 7.52-7.43 (m, 2H), 7.43-7.29 (m, 6H), 7.25-7.18 (m, 1H), 7.06 (d, J=9.3 Hz, 1H), 5.72 (br. s., 1H), 5.57 (br. s., 1H), 5.29 (d, J=8.0 Hz, 1H), 4.08 (d, J=10.3 Hz, 1H), 3.43 (s, 3H), 3.41-3.29 (m, 1H), 2.36-2.17 (m, 2H), 2.07-1.91 (m, 2H).

Example 4

(2R,3R)—N-((3S)-2-Oxo-5-phenyl-2,3-dihydro-1H-1,4-benzodiazepin-3-yl)-3-phenyl-2-(3,3,3-trifluoropropyl)succinamide

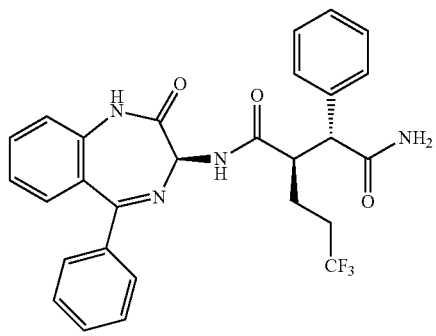 [SMILES: NC(=O)[C@@H](c1ccccc1)[C@@H](CCC(F)(F)F)C(=O)N[C@H]1N=C(c2ccccc2)c2ccccc2NC1=O]

Preparation 4A: (3S)-3-Amino-5-phenyl-1,3-dihydro-2H-1,4-benzodiazepin-2-one

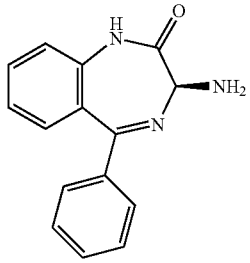

(4A)

Racemic (3S)-3-amino-5-phenyl-1,3-dihydro-2H-1,4-benzodiazepin-2-one (*J. Med. Chem.*, 49:2311-2319 (2006), compound #5) was prepared according to the literature procedure. The enantiomers were separated on Berger SFC MGIII Column: Lux 25×3 cm, 5 cm; Mobile Phase: 30% MeOH+0.1% DEA in $CO_2$; Flow rate: 150 mL/min; Temperature: 40° C.; Detector wavelength: 250 nM. Obtained the S-enantiomer as a white solid: $^1$H NMR (400 MHz, DMSO-$d_6$) δ 10.67 (1H, br. s.), 7.58 (1H, td, J=7.65, 1.76 Hz), 7.37-7.53 (5H, m), 7.23-7.30 (2H, m), 7.14-7.22 (1H, m), 4.23 (1H, s), 2.60 (2H, br. s.); HPLC: RT=3.0625 min (30% MeOH+0.1% DEA in $CO_2$ on OD-H Column, 3 mL/min, 35° C., 96 bar, 230 nm, 10 µl inj); $[\alpha]_D$=−208.3° (5.05 mg/mL, MeOH). Also obtained the R-enantiomer as off-white solids: R-enantiomer: HPLC: RT=3.970 min; $[\alpha]_D$=182.1° (2.01 mg/mL, MeOH).

Preparation 4B:
(2R)-5,5,5-Trifluoro-2-hydroxypentanoic acid

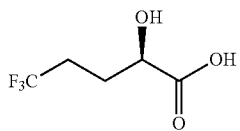

(4B)

To a cool (0° C.), stirred solution of (2R)-2-amino-5,5,5-trifluoropentanoic acid (4.09 g, 23.90 mmol) (U.S. Publication No. 2009/0111858 A1) and $H_2SO_4$ (2.8 mL, 52.5 mmol) in water (95 mL) was added a solution of sodium nitrite (9.89 g, 143 mmol) in water (30 mL) dropwise via addition funnel over 60 min. The reaction mixture was allowed to slowly warm to room temperature and stirred overnight. The reaction mixture was diluted with $Et_2O$, the aqueous phase was separated and extracted with $Et_2O$ (3×). The combined organics were dried ($Na_2SO_4$), filtered and concentrated under reduced pressure to provide Preparation 4B (4.1551 g, >99%) as an amber oil. $^1$H NMR (400 MHz, $CDCl_3$) δ 4.33 (1H, dd, J=8.03, 4.27 Hz), 2.09-2.42 (3H, m), 1.88-2.02 (1H, m).

Preparation 4C: Benzyl
(2R)-5,5,5-trifluoro-2-hydroxypentanoate

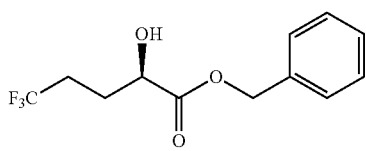

(4C)

To a stirred solution of Preparation 4B (4.1551 g, 24.14 mmol), benzyl alcohol (3.2 mL, 30.8 mmol) in benzene (40 mL) was added $H_2SO_4$ (0.28 mL, 5.25 mmol). The reaction mixture was heated to 50° C. for 10 h. The reaction mixture was cooled to room temperature, cooled in ice/water bath and then 0.5M NaOH (32 mL, 16.00 mmol) was added. The mixture was stirred for a few minutes, and was extracted with $Et_2O$, washed with brine, dried ($Na_2SO_4$), filtered and concentrated under reduced pressure. The residue was purified by flash chromatography (Teledyne ISCO CombiFlash Rf, 0% to 100% solvent $CH_2Cl_2$/EtOAc, REDISEP® $SiO_2$ 120 g). Concentration of appropriate fractions provided Preparation 4C (3.88 g, 61%) as a colorless oil: $^1$H NMR (400 MHz, $CDCl_3$) δ 7.33-7.44 (5H, m), 5.25 (2H, s), 4.28 (1H, dt, J=8.09, 4.11 Hz), 2.85 (1H, d, J=4.77 Hz), 2.07-2.34 (3H, m), 1.84-1.96 (1H, m).

Preparation 4D: Benzyl (2R)-5,5,5-trifluoro-2-{[(trifluoromethyl)sulfonyl]oxy}pentanoate

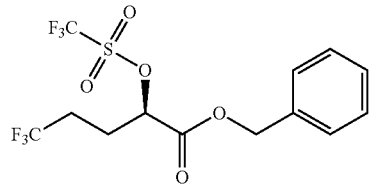

(4D)

To a cold (−25° C.), stirred solution of 2,6-lutidine (2.352 mL, 20.19 mmol) in $CH_2Cl_2$ (30 mL) was added triflic anhydride (3.18 mL, 18.85 mmol) slowly over 2 minutes. The reaction mixture was stirred at −25° C. and became light yellow/orange in color. After 10 min, Preparation 4C (3.53 g, 13.46 mmol) was added dropwise over 5 min and stirred at −25° C. for 30 minutes. The reaction mixture was warmed to room temperature and concentrated to a small volume. The residue was diluted with heptane and loaded directly onto a silica gel column (220 g), eluted with a gradient from 20% $CH_2Cl_2$/heptane to 50% $CH_2Cl_2$/heptane. Concentration of appropriate fractions provided Preparation 4D (3.476 g, 66%): $^1$H NMR (400 MHz, $CDCl_3$) δ 7.33-7.45 (5H, m), 5.29 (2H, d, J=5.50 Hz), 5.21 (1H, t, J=5.50 Hz), 2.04-2.37 (4H, m).

Preparation 4E: (4R)-4-Benzyl-3-(phenylacetyl)-1,3-oxazolidin-2-one

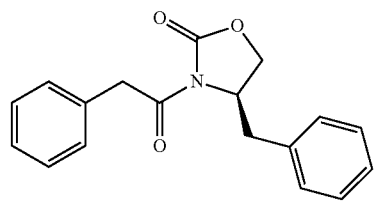

(4E)

To a cold (−78° C.), stirred solution of (4R)-4-benzyl-1,3-oxazolidin-2-one (4.17 g, 23.53 mmol) in THF (100 mL) under nitrogen atmosphere was added n-BuLi (9.5 mL, 23.75 mmol) dropwise via syringe over 10 min. After stirring for 10 min, a solution of 2-phenylacetyl chloride (3.2 mL, 24.20 mmol) in THF (20 mL) was added via cannula over 10 min. After the addition was complete, the reaction mixture was placed in an ice-water bath and was stirred at 0° C. for 1 hr, then removed from the ice bath. To the reaction mixture was added aqueous saturated $NH_4Cl$ and was extracted with EtOAc (2×). The combined organics were washed with brine, dried ($Na_2SO_4$), filtered and concentrated under reduced pressure. The residue was purified by flash chromatography (Teledyne ISCO CombiFlash Rf, 0% to 100% solvent hexanes/EtOAc, REDISEP® $SiO_2$ 120 g). Concentration of appropriate fractions provided Preparation 4E (6.19 g, 89%) as a colorless viscous oil: $^1$H NMR (400 MHz, $CDCl_3$) δ 7.32-7.39 (4H, m), 7.21-7.32 (4H, m), 7.10-7.17 (2H, m), 4.67 (1H, dddd, J=10.29, 6.34, 3.45, 3.26 Hz), 4.30 (2H, q, J=15.56 Hz), 4.15-4.22 (2H, m), 3.26 (1H, dd, J=13.30, 3.26 Hz), 2.76 (1H, dd).

Preparation 4F: Benzyl (2R)-2-((1R)-2-((4R)-4-benzyl-2-oxo-1,3-oxazolidin-3-yl)-2-oxo-1-phenylethyl)-5,5,5-trifluoropentanoate (4F)

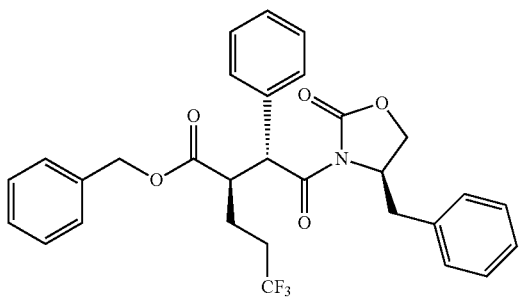

To a cold (−78° C.), stirred solution of Preparation 4E (1 g, 3.39 mmol) in THF (10 mL) was added LiHMDS (1M in THF) (4.06 mL, 4.06 mmol) dropwise over 5 min. The reaction mixture was stirred at −78° C. for 1.5 hr, and then placed into a −45° C. bath. To the reaction mixture was added Preparation 4D (1.602 g, 4.06 mmol) in THF (5 mL) over 1 min and stirred at −45° C. for 2 hr. Next the reaction mixture was removed from −45° C. bath and warmed to room temperature. The reaction was judged complete by HPLC. To the reaction mixture was added aqueous saturated $NH_4Cl$ and extracted with EtOAc, washed with brine, dried ($Na_2SO_4$), filtered and concentrated under reduced pressure. The residue was purified by flash chromatography (Teledyne ISCO, 5% to 40% solvent A/B=hexanes/EtOAc, REDISEP® $SiO_2$ 120 g). Concentration of appropriate fractions provided Preparation 4F (1.429 g, 78%): HPLC: RT=3.790 min (CHROMOLITH® SpeedROD 4.6×50 mm (4 min grad) eluting with 10-90% aqueous MeOH over 4 minutes containing 0.1% TFA, 4 mL/min, monitoring at 220 nm); MS(ES): m/z=540 [M+H]$^+$; $^1$H NMR (500 MHz, $CDCl_3$) δ 7.31-7.39 (4H, m), 7.24-7.31 (7H, m), 7.22 (2H, d, J=7.15 Hz), 6.99-7.05 (2H, m), 5.38 (1H, d, J=11.00 Hz), 4.76-4.88 (2H, m), 4.58 (1H, dddd, J=10.10, 7.35, 2.89, 2.75 Hz), 4.08-4.12 (1H, m), 4.02 (1H, t, J=8.25 Hz), 3.45 (1H, td, J=10.45, 3.30 Hz), 3.34 (1H, dd, J=13.20, 3.30 Hz), 2.76 (1H, dd, J=13.20, 9.90 Hz), 1.97-2.20 (3H, m), 1.83-1.94 (1H, m).

Preparation 4G: (2R)-2-((1R)-2-((4R)-4-Benzyl-2-oxo-1,3-oxazolidin-3-yl)-2-oxo-1-phenylethyl)-5,5,5-trifluoropentanoic acid (4G)

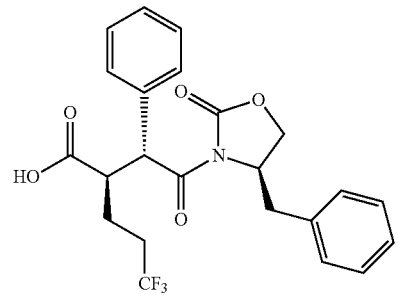

A stirred suspension of Preparation 4F (1.42 g, 2.63 mmol) and Pearlman's Catalyst (0.111 g, 0.790 mmol) in MeOH (20 mL) was stirred under hydrogen atmosphere for 45 min. The reaction was judged complete by HPLC. The reaction mixture was filtered through a 0.45 μm membrane filter and rinsed with MeOH. The filtrate was concentrated and dried under high vacuum to provide Preparation 4G (1.182 g, 100%) as an off-white solid: HPLC: RT=3.138 min (CHROMOLITH® SpeedROD 4.6×50 mm (4 min grad) eluting with 10-90% aqueous MeOH over 4 minutes containing 0.1% TFA, 4 mL/min, monitoring at 220 nm); MS(ES): m/z=450 [M+H]$^+$; $^1$H NMR (500 MHz, $CDCl_3$) δ 7.32-7.41 (4H, m), 7.27-7.31 (4H, m), 7.23 (2H, d, J=7.70 Hz), 5.37 (1H, d, J=10.45 Hz), 4.59 (1H, t, J=8.25 Hz), 4.12 (1H, d, J=8.25 Hz), 4.04 (1H, t, J=8.25 Hz), 3.32-3.43 (2H, m), 2.79 (1H, dd, J=13.20, 9.90 Hz), 2.18 (2H, dq, J=18.35, 9.10 Hz), 1.97-2.08 (1H, m), 1.85-1.96 (1H, m).

Preparation 4H: (2R)-2-((1R)-2-((4R)-4-Benzyl-2-oxo-1,3-oxazolidin-3-yl)-2-oxo-1-phenylethyl)-5,5,5-trifluoro-N-((3S)-2-oxo-5-phenyl-2,3-dihydro-1H-1,4-benzodiazepin-3-yl)pentanamide (4H)

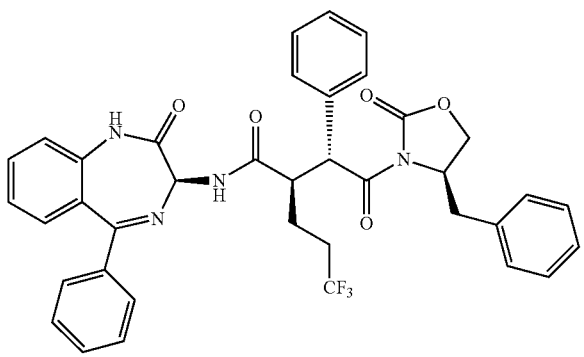

To a stirred solution of Preparation 4A (408 mg, 1.624 mmol) and Preparation 4G (730 mg, 1.624 mmol) in DMF (10 mL) was added O-benzotriazol-1-yl-N,N,N',N'-tetra-methyluronium tetrafluoroborate (573 mg, 1.786 mmol) and diisopropylethylamine (0.60 mL, 3.41 mmol). The reaction mixture was stirred overnight. The reaction was judged complete by LCMS. The reaction mixture was diluted with water (56 mL) and sat. NaHCO₃ (7 mL), stirred at room temperature for 30 min, then the precipitate was collected by filtration and rinsed with water (3×10 mL), dried under vacuum. Obtained Preparation 4H (1.080 g, 97%): HPLC: RT=3.171 min (CHROMOLITH® ODS 4.6×50 mm (4 min grad) eluting with 10-90% aqueous MeOH over 4 minutes containing 0.0% TFA, 4 mL/min, monitoring at 220 nm); MS(ES): m/z=600 [M+H]⁺; ¹H NMR (400 MHz, CDCl₃) δ 8.03 (1H, s), 7.95 (1H, s), 7.42-7.58 (4H, m), 7.23-7.43 (13H, m), 7.15-7.22 (1H, m), 7.10 (1H, d, J=8.03 Hz), 6.87 (1H, d, J=8.03 Hz), 5.44 (1H, d, J=10.79 Hz), 5.27 (1H, d, J=8.03 Hz), 4.58-4.70 (1H, m), 4.00-4.17 (2H, m), 3.30-3.48 (2H, m), 2.27-2.44 (2H, m), 2.06-2.23 (1H, m), 1.85-2.00 (1H, m).

Preparation 4I: (2R,3R)-6,6,6-Trifluoro-3-(((3S)-2-oxo-5-phenyl-2,3-dihydro-1H-1,4-benzodiazepin-3-yl)carbamoyl)-2-phenylhexanoic acid

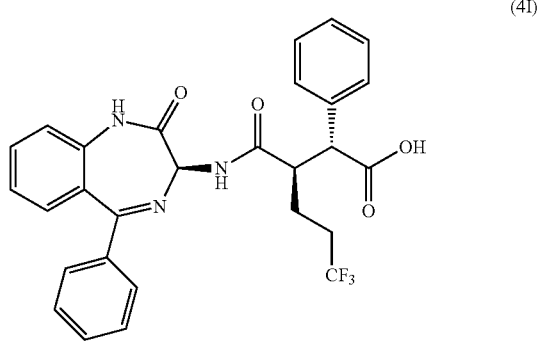 [SMILES: O=C1Nc2ccccc2C(c2ccccc2)=N[C@@H]1NC(=O)[C@H](CCC(F)(F)F)[C@@H](C(=O)O)c1ccccc1]

(4I)

Hydrogen peroxide (0.404 mL, 3.95 mmol) and lithium hydroxide (31.6 mg, 1.318 mmol) were taken in water (1.50 mL) and were stirred at room temperature until the solution was homogeneous and clear. This mixture was added to a solution of Preparation 4H (300 mg, 0.439 mmol) in THF (5 mL) and stirred for 30 min. The reaction mixture was diluted with pH 4 phosphate buffer (20 mL) and 1% NaHSO₃ solution (10 mL) (pH~4) and extracted with EtOAc (2×80 mL). The combined organics were washed with brine, dried (Na₂SO₄), filtered and concentrated under reduced pressure. The residue was purified by flash chromatography (Teledyne ISCO, 25% to 100% solvent A/B=hexanes/EtOAc, REDISEP® SiO₂ 40 g, DCM liquid loading). Concentration of appropriate fractions provided Preparation 4I (129.6 mg, 56%).

Example 4

Example 4 was prepared from Preparation 4I (92.6 mg, 0.177 mmol) by the general method shown for Example 1. Example 4 (54.7 mg, 58%) was obtained as a white solid: HPLC: RT=2.447 min (CHROMOLITH® ODS 4.6×50 mm (4 min grad) eluting with 10-90% aqueous MeOH over 4 minutes containing 0.0% TFA, 4 mL/min, monitoring at 220 nm); MS(ES): m/z=523 [M+H]⁺; ¹H NMR (500 MHz, DMSO-d₆) δ 10.78 (1H, s), 9.27 (1H, d, J=7.70 Hz), 7.70 (1H, br. s.), 7.55-7.65 (1H, m), 7.51 (1H, t, J=7.15 Hz), 7.44 (2H, t, J=7.42 Hz), 7.36 (4H, dd, J=19.25, 7.15 Hz), 7.13-7.30 (6H, m), 6.93 (1H, br. s.), 4.89 (1H, d, J=7.15 Hz), 3.70 (1H, d, J=11.00 Hz), 3.43 (1H, td, J=10.86, 3.02 Hz), 2.58-2.77 (1H, m), 2.25-2.41 (1H, m), 1.74-1.87 (1H, m), 1.55-1.74 (1H, m).

Example 4

Example 4 was also prepared from Intermediate 4A (36.3 mg, 0.144 mmol) and Intermediate S-1 (50.0 mg, 0.144 mmol) according to the general procedure shown for Example 5. Example 4 (24.0 mg, 29.3%) was obtained. HPLC: RT=8.62 min (H₂O/CH₃CN with TFA, SunFire C18 3.5 µm, 4.6×150 mm, gradient=15 min, wavelength=220 and 254 nm); MS(ES):m/z=523.3 [M+H]⁺; ¹H NMR (400 MHz, DMSO-d₆) δ 10.77 (s, 1H), 9.25 (d, J=7.5 Hz, 1H), 7.69 (br. s., 1H), 7.60 (ddd, J=8.3, 6.2, 2.5 Hz, 1H), 7.54-7.49 (m, 1H), 7.44 (t, J=7.4 Hz, 2H), 7.40-7.32 (m, 4H), 7.29-7.17 (m, 6H), 6.92 (br. s., 1H), 4.89 (d, J=7.7 Hz, 1H), 3.70 (d, J=11.2 Hz, 1H), 3.50-3.39 (m, 1H), 2.75-2.62 (m, 1H), 2.34 (d, J=11.9 Hz, 1H), 1.86-1.74 (m, 1H), 1.73-1.61 (m, 1H).

Synthesis of Benzodiazepine Intermediates

Intermediate B-1: Racemic 3-amino-5-(3-fluorophenyl)-9-methyl-1H-benzo[e][1,4]diazepin-2(3H)-one

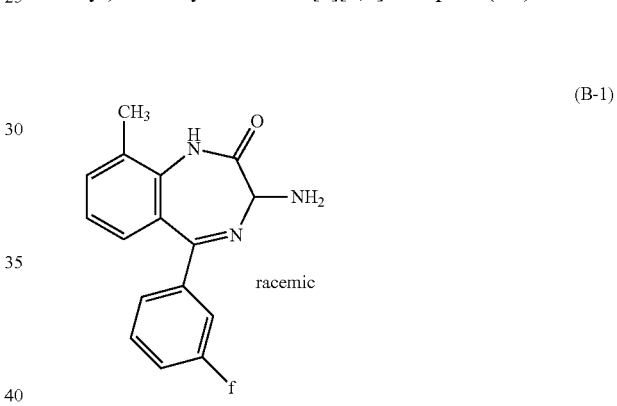

(B-1)

racemic

Intermediate B-1A: 2-Amino-N-methoxy-N,3-dimethylbenzamide

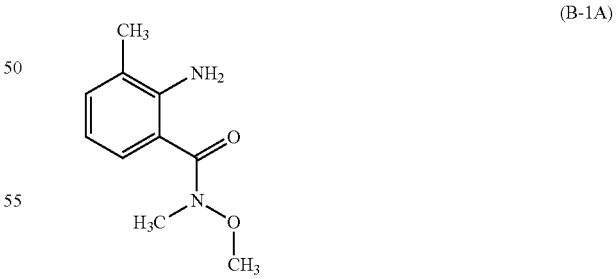

(B-1A)

In a 1 L round-bottomed flask was added 2-amino-3-methylbenzoic acid (11.2 g, 74.1 mmol), N,O-dimethylhydroxylamine hydrochloride (14.45 g, 148 mmol) in CH₂Cl₂ (500 mL) to give a pale brown suspension. The reaction mixture was treated with Et₃N (35 mL) to give a light brown/red solution. The solution was treated with HOBT (11.35 g, 74.1 mmol) and EDC (14.20 g, 74.1 mmol) and stirred at room temperature for 24 hours. The mixture was then washed with 10% LiCl aq acidified with 1N HCl. The organic layer was washed successively with 10% aqueous LiCl and aqueous NaHCO$_3$. The organic layer was decolorized with charcoal, filtered and the filtrate dried over MgSO$_4$. The mixture was filtered and concentrated to give 13.22 g (92% yield) of 2-amino-N-methoxy-N,3-dimethylbenzamide as an oil. MS(ES):m/z=195.1 [M+H$^+$]; HPLC: RT=1.118 min. (H$_2$O/MeOH with TFA, CHROMOLITH® ODS S5 4.6×50 mm, gradient=4 min, wavelength=220 nm); $^1$H NMR (500 MHz, chloroform-d) δ 7.22 (dd, J=7.8, 0.8 Hz, 1H), 7.12-7.06 (m, 1H), 6.63 (t, J=7.5 Hz, 1H), 4.63 (br. s., 2H), 3.61 (s, 3H), 3.34 (s, 3H), 2.17 (s, 3H). This was used without further purification in next reaction.

Intermediate B-1B:
(2-Amino-3-methylphenyl)(3-fluorophenyl)methanone

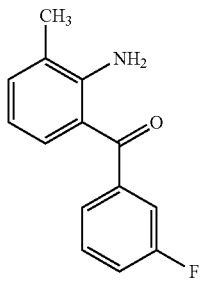

(B-1B)

In a 500 mL round-bottomed flask a solution of 1-fluoro-3-iodobenzene (13.61 mL, 116 mmol) in THF (120 mL) was cooled in −78° C. bath. A solution BuLi, 2.5M in hexane (46.3 mL, 116 mmol) was added dropwise over 10 minutes to give a slightly cloudy yellow solution. The solution was stirred at −78° C. for 30 minutes and then treated with a solution of 2-amino-N-methoxy-N,3-dimethylbenzamide (6.43 g, 33.1 mmol) in THF (30 mL). After 1.5 hours the reaction mixture was added to a mixture of ice and 1N HCl (149 mL, 149 mmol) and reaction flask rinsed with THF (5 ml) and combined with the aqueous mixture. The resulting mixture was diluted with 10% aq LiCl and the pH was adjusted to 4.00 with 1N NaOH. The mixture was extracted with Et$_2$O, washed with brine, dried over MgSO$_4$, filtered and concentrated. The resulting residue was purified on silica gel column (220 g ISCO) eluting with a gradient from 10% EtOAc/hexane to 30% EtOAc/hexane. The product was collected and concentrated to give (2-amino-3-methylphenyl)(3-fluorophenyl)methanone (7.11 g, 94% yield) as an oil. MS(ES): m/z=230.1 [M+H$^+$]; HPLC: RT=2.820 min Purity=99%. (H$_2$O/MeOH with TFA, CHROMOLITH® ODS S5 4.6×50 mm, gradient=4 min, wavelength=220 nm);

Intermediate B-1C: Benzyl (5-(3-fluorophenyl)-9-methyl-2-oxo-2,3-dihydro-1H-benzo[e][1,4]diazepin-3-yl)carbamate

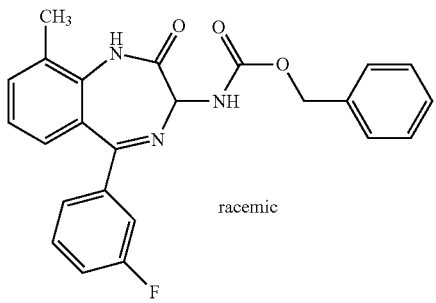

(B-1C)

racemic

In a 1 L round-bottomed flask, a solution of 2-(1H-benzo[d][1,2,3]triazol-1-yl)-2-((phenoxycarbonyl)amino)acetic acid (19.37 g, 62.0 mmol) in THF (135 mL) was cooled in ice/water bath and treated with oxalyl chloride (5.43 mL, 62.0 mmol) and 4 drops DMF (bubbling). The reaction mixture was stirred for 4 hours (until HPLC analysis showed complete conversion to acid chloride). Then a solution of (2-amino-3-methylphenyl)(3-fluorophenyl)methanone (7.11 g, 31.0 mmol) in THF (35 mL) was added with 5 mL THF rinse and the resulting solution was removed from ice/water bath and stirred at room temperature for 1.5 hours. The mixture was then treated with a solution of ammonia, 7M in MeOH (19.94 mL, 140 mmol) (slight exotherm, immediately a white precipitate formed and mixture was cooled in ice/water bath). After 15 mins another portion of ammonia, 7M in MeOH (19.94 mL, 140 mmol) was added and the resulting mixture was removed from ice/water bath and sealed under N$_2$ and stirred overnight at room temperature. The reaction mixture was concentrated to ~½ volume and the resulting mixture was diluted with AcOH (63 mL) and stir at room temperature for 4 hours (until HPLC analysis showed complete conversion). The reaction mixture was concentrated and the residue dilute with 500 mL water and to give an orange sticky precipitate. Hexane and Et$_2$O was added and stir at room temperature for 1 hour to form an orange solid. Et$_2$O was removed under a stream of nitrogen and the aqueous layer was decanted. The orange sticky residue was triturate with 40 mL iPrOH and stir at room temperature to give a white precipitate. The solid was filtered and washed with iPrOH, dried on filter frit under a stream of nitrogen to give benzyl (5-(3-fluorophenyl)-9-methyl-2-oxo-2,3-dihydro-1H-benzo[e][1,4]diazepin-3-yl)carbamate (5.4 g, 41.7% yield). MS(ES):m/z=418.3 [M+H$^+$]; HPLC: RT=3.075 min Purity=99%. (H$_2$O/MeOH with TFA, CHROMOLITH® ODS S5 4.6×50 mm, gradient=4 min, wavelength=220 nm).

Intermediate B-1

A suspension of benzyl (5-(3-fluorophenyl)-9-methyl-2-oxo-2,3-dihydro-1H-benzo[e][1,4]diazepin-3-yl)carbamate (470 mg, 1.126 mmol) in acetic acid (5 mL) was treated with HBr, 33% in acetic acid (1.853 mL, 11.26 mmol) and stirred at room temperature for 1.5 hours. The reaction mixture was diluted with ether and the resulting precipitate was stirred at room temperature for 1 hour and then filtered to give Intermediate B-1 (370 mg, 90% yield) as a tan/orange solid. MS(ES):m/z=284.0 [M+H$^+$]. HPLC: RT=1.75 min (H$_2$O/MeOH with 0.1% TFA, Luna C18 3 μm, 4.6×30 mm, gradient=3.5 min, wavelength=220).

Intermediate B-2: (S)-3-Amino-5-(3-fluorophenyl)-9-methyl-1H-benzo[e][1,4]diazepin-2(3H)-one

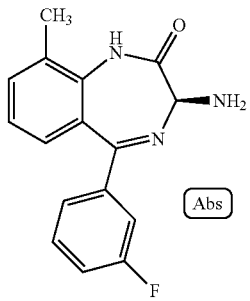

(B-2)

Intermediate B-2A: (S)-Benzyl (5-(3-fluorophenyl)-9-methyl-2-oxo-2,3-dihydro-1H-benzo[e][1,4]diazepin-3-yl)carbamate

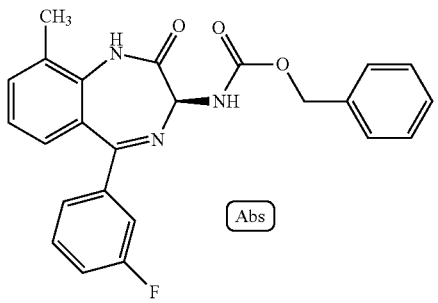

(B-2A)

Racemic benzyl (5-(3-fluorophenyl)-9-methyl-2-oxo-2,3-dihydro-1H-benzo[e][1,4]diazepin-3-yl)carbamate (5.9 g, 14.3 mmol) was resolved under the Chiral SFC conditions. Berger SFC MGIII, Column: CHIRALPAK® IC 25×3 cm ID, 5 µm, Mobile Phase: 45/55 $CO_2$/MeOH; Flow rate: 160 mL/min; Detector wavelength: 220 nM. The desired stereoisomer was collected as the second peak in the elution order. After evaporation of solvent, (S)-benzyl (5-(3-fluorophenyl)-9-methyl-2-oxo-2,3-dihydro-1H-benzo[e][1,4]diazepin-3-yl)carbamate (2.73 g, 46% yield) was obtained as a white solid. HPLC: RT=3.075 min Purity=99%. ($H_2O$/MeOH with TFA, CHROMOLITH® ODS S5 4.6×50 mm, gradient=4 min, wavelength=220 nm). Chiral HPLC RT: 8.661 min(AD, 60% (EtOH/MeOH)/heptane)>99% ee. (on AD chiral column desired is the first peak, which is the second peak on the IC SFC).

Intermediate B-2

In a 100 mL round-bottomed flask a solution of (S)-benzyl (5-(3-fluorophenyl)-9-methyl-2-oxo-2,3-dihydro-1H-benzo[e][1,4]diazepin-3-yl)carbamate (2.729 g, 6.54 mmol) in acetic acid (12 mL) was treated with HBr, 33% in HOAc (10.76 mL, 65.4 mmol) and stirred at room temperature for 1 hour.

The solution was diluted with $Et_2O$ to give a yellow precipitate. The yellow solid was filtered and rinsed with $Et_2O$ under nitrogen. The solid was transferred to 100 mL round bottom and added water (white precipitate formed) and slowly basified with saturated $NaHCO_3$. The resulting tacky precipitate was extracted with EtOAc (not very soluble in EtOAc, needed large volume). The organic layer was washed with water and then dried over $MgSO_4$. The resulting material was filtered, concentrated, and dried under vacuum to give Intermediate B-2 (1.68 g, 91% yield) as a white foam solid. MS(ES):m/z=284.2 [M+H$^+$]; HPLC: RT=1.72 min Purity=99%. ($H_2O$/MeOH with TFA, CHROMOLITH® ODS S5 4.6×50 mm, gradient=4 min, wavelength=220 nm).

Intermediate B-3: 3-Amino-5-(4-fluorophenyl)-9-methyl-1H-benzo[e][1,4]diazepin-2(3H)-one

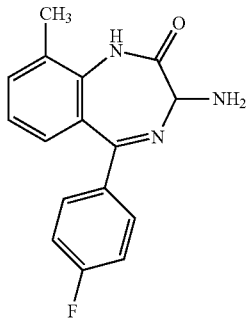

(B-3)

Intermediate B-3 was synthesized following the procedure used for the synthesis of Intermediate B-1 to give 3-amino-5-(4-fluorophenyl)-9-methyl-1H-benzo[e][1,4]diazepin-2(3H)-one, hydrobromide as a tan solid: MS(ES):m/z=284.0 [M+H$^+$]. HPLC: RT=0.65 min ($H_2O$/$CH_3CN$ with 0.05% TFA, BEH C18 1.7 µm, 2.1×50 mm, gradient (2%-98%)=1 min, wavelength=220.

Intermediate B-4: 3-Amino-9-methyl-5-(3-(trifluoromethyl)phenyl)-1H-benzo[e][1,4]diazepin-2(3H)-one

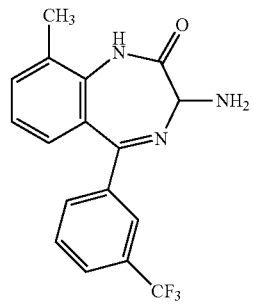

(B-4)

Intermediate B-4 was synthesized following the procedure used for the synthesis of Intermediate B-1 to give 3-amino-9-methyl-5-(3-(trifluoromethyl)phenyl)-1H-benzo[e][1,4]diazepin-2(3H)-one, hydrobromide as a light-yellow solid: MS(ES):m/z=334.0 [M+H$^+$]. HPLC: RT=0.73 min ($H_2O$/$CH_3CN$ with 0.05% TFA, BEH C18 1.7 µm, 2.1×50 mm, gradient (2%-98%)=1 min, wavelength=220.

Intermediate B-5: 3-Amino-5-(3-chlorophenyl)-9-methyl-1H-benzo[e][1,4]diazepin-2(3H)-one

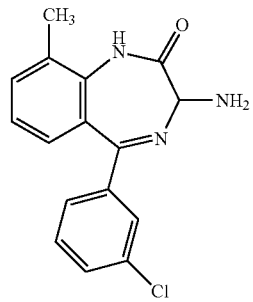

(B-5)

Intermediate B-5 was synthesized following the procedure used for the synthesis of Intermediate B-1 to give 3-amino-5-(3-chlorophenyl)-9-methyl-1H-benzo[e][1,4]diazepin-2(3H)-one, hydrobromide as a light-yellow solid: MS(ES):m/z=300.3 [M+H$^+$]. HPLC: RT=1.91 min ($H_2O$/MeOH with 0.1% TFA, Luna C18 3 µm, 4.6×30 mm, gradient=3.5 min, wavelength=220).

Intermediate B-6: Amino-5-(3-(difluoromethyl)phenyl)-9-methyl-1H-benzo[e][1,4]diazepin-2(3H)-one

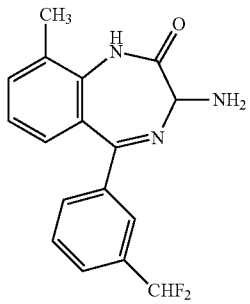

(B-6)

Intermediate B-6 was synthesized following the procedure used for the synthesis of Intermediate B-1 to give 3-amino-5-(3-(difluoromethyl)phenyl)-9-methyl-1H-benzo[e][1,4]diazepin-2(3H)-one, hydrobromide as a light-yellow solid: MS(ES): m/z=316.1 [M+H$^+$]. HPLC: RT=0.70 min (H$_2$O/CH$_3$CN with 0.05% TFA, BEH C18 1.7 μm, 2.1×50 mm, gradient (2%-98%)=1 min, wavelength=220.

Intermediate B-7: 3-Amino-9-cyclopropoxy-5-(3-fluorophenyl)-1H-benzo[e][1,4]diazepin-2(3H)-one

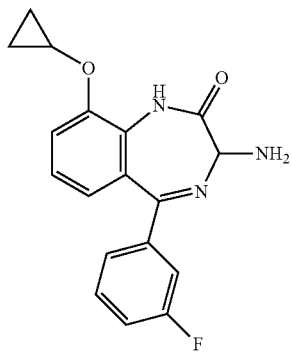

(B-7)

Intermediate B-7A: Methyl 2-nitro-3-(vinyloxy)benzoate

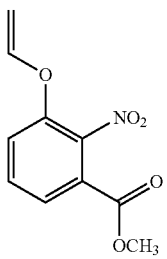

(B-7A)

A mixture of copper (II) acetate (11.98 g, 65.9 mmol) and dichloromethane (80 mL) were stirred at room temperature for 10 minutes, before the addition of 2,4,6-trivinyl-1,3,5,2,4,6-trioxatriborinane compound with pyridine (1:1) (10.63 g, 44.2 mmol, 0.67 eq), methyl 3-hydroxy-2-nitrobenzoate (U.S. Publication No. 2012/0035194 A1 [0202]) (13 g, 65.9 mmol), pyridine (26.7 mL, 330 mmol), and molecular sieves (1 g). The resulting deep blue mixture was stirred at room temperature for 5 days, with the reaction mixture opened to the air. The reaction mixture was filtered through a pad of CELITE®, washing with some dichloromethane. The filtrate was washed with 3M aqueous ammonium acetate (2×), water, brine, and then dried, filtered and concentrated in vacuo. The crude product mixture was purified via ISCO (0% to 20% of EtOAc/DCM in 15 minutes, 120 g column) to give methyl 2-nitro-3-(vinyloxy)benzoate (7.42 g, 33.2 mmol, 50.4% yield). HPLC: RT=2.487 min (H$_2$O/MeOH with TFA, SunFire C18 3.5 μm, 2.1×30 mm, gradient=4 min, wavelength=220 nm); MS(ES):m/z=246 [M+Na]$^+$; $^1$H NMR (400 MHz, chloroform-d) δ 7.77 (dd, J=7.8, 1.2 Hz, 1H), 7.55 (t, J=8.1 Hz, 1H), 7.38 (dd, J=8.4, 1.3 Hz, 1H), 6.61 (dd, J=13.6, 5.9 Hz, 1H), 4.95 (dd, J=13.6, 2.4 Hz, 1H), 4.69 (dd, J=5.9, 2.4 Hz, 1H), 3.93 (s, 3H), 1.56 (s, 1H), 0.03 (s, 1H).

Intermediate B-7B: Methyl 3-cyclopropoxy-2-nitrobenzoate

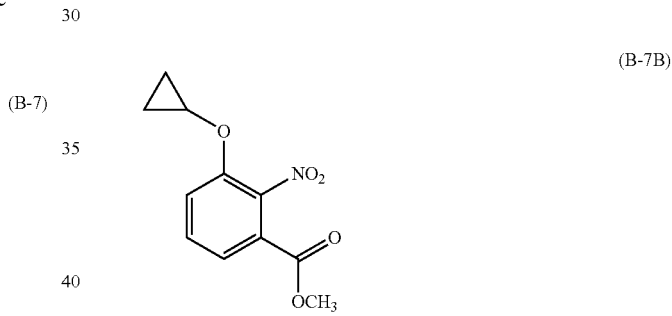

(B-7B)

In a 3 necked, 500 mL flask, a solution of 2,2,2-trichloroacetic acid (16.30 g, 100 mmol) in dichloromethane (100 mL) was slowly added via an addition funnel to a −10° C. solution of diethylzinc (1M hexanes, 100 mL, 100 mmol) under a nitrogen atmosphere. The reaction mixture was stirred for 10 min. Next, diiodomethane (8 mL, 100 mmol) was dropwise added by syringe, and the reaction solution was stirred for 10 min. A solution of methyl 2-nitro-3-(vinyloxy)benzoate (7.42 g, 33.2 mmol) in dichloromethane (20 mL) was added slowly via an addition funnel. The solution was allowed to warm to room temperature overnight. The reaction mixture was cooled to 0° C. and quenched with 1M HCl. The reaction solution was transferred to a separatory funnel, and the aqueous layer extracted with dichloromethane (3×). The combined extracts were washed with saturated sodium bicarbonate, water and brine, dried over anhydrous sodium sulfate, filtered and concentrated. The crude product mixture was purified by ISCO (0% of EtOAc/heptane in 15 minutes, 220 g column) to provide methyl 3-cyclopropoxy-2-nitrobenzoate (4.7 g, 19.81 mmol, 60.0% yield). HPLC: RT=2.66 min (H$_2$O/MeOH with TFA, SunFire C18 3.5 μm, 2.1×30 mm, gradient=4 min, wavelength=220 nm); MS(ES):m/z=260

[M+Na]⁺; ¹H NMR (400 MHz, chloroform-d) δ 7.68-7.57 (m, 2H), 7.57-7.41 (m, 1H), 4.03-3.82 (m, 4H), 0.94-0.78 (m, 4H).

Intermediate B-7C: 3-Cyclopropoxy-2-nitrobenzoic acid

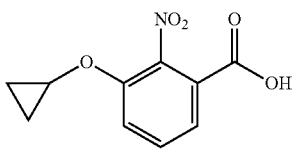

(B-7C)

A solution of methyl 3-cyclopropoxy-2-nitrobenzoate (4.7 g, 19.81 mmol) in THF (30 mL) and MeOH (30 mL) was treated with a solution of lithium hydroxide (2.88 g, 120 mmol) in water (15 mL, 833 mmol). The mixture was stirred at room temperature for 2 hours. The organic solvents were removed under reduced pressure. The resulting aqueous slurry was diluted with water, acidified with 1M HCl and extracted with ethyl acetate (3×). The extracts were combined and washed with brine, dried over anhydrous sodium sulfate, filtered and concentrated to provide 3-cyclopropoxy-2-nitrobenzoic acid (4.35 g, 19.8 mmol, 98% yield) as a yellowish solid. HPLC: RT=2.186 min (H₂O/MeOH with TFA, SunFire C18 3.5 μm, 2.1×30 mm, gradient=4 min, wavelength=220 nm); MS(ES):m/z=246 [M+Na]⁺; ¹H NMR (400 MHz, chloroform-d) δ 7.76 (dd, J=7.7, 1.8 Hz, 1H), 7.68-7.46 (m, 2H), 4.02 (tt, J=6.0, 2.9 Hz, 1H), 1.00-0.52 (m, 4H).

Intermediate B-7D: 2-Amino-3-cyclopropoxybenzoic acid

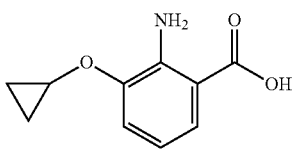

(B-7D)

A 50 mL round bottom flask was charged with 3-cyclopropoxy-2-nitrobenzoic acid (205 mg, 0.919 mmol), 10% Pd/C (25 mg, 0.919 mmol) and methanol (6 mL). The flask was vacuum flushed with nitrogen (3×) followed by a vacuum flush with a hydrogen balloon (3×). The resulting suspension was stirred under a balloon of hydrogen at room temperature over night. The solution was filtered through CELITE®, washing with methanol, and the filtrate was concentrated to provide reddish oil. The crude material was azeotroped with toluene (2×), and dried under vacuum to provide crude 2-amino-3-cyclopropoxybenzoic acid (175 mg, 0.906 mmol, 99% yield) as a reddish solid. The product was used without further purification in the next reaction. HPLC: RT=2.31 min (H₂O/MeOH with TFA, SunFire C18 3.5 μm, 2.1×30 mm, gradient=4 min, wavelength=220 nm); MS(ES): m/z=194.12 [M+H]⁺.

Intermediate B-7E: 2-Amino-3-cyclopropoxy-N-methoxy-N-methylbenzamide

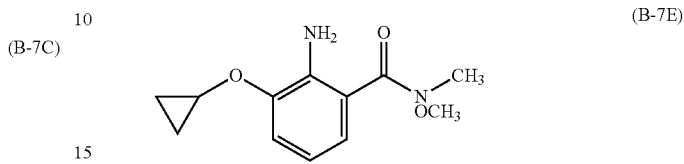

(B-7E)

In a flask at room temperature, was added 2-amino-3-cyclopropoxybenzoic acid (6.61 g, 34.2 mmol) N,O-dimethylhydroxylamine hydrochloride (10.01 g, 103 mmol), N-ethyl-N"-(3-dimethylaminopropyl)carbodiimide hydrochloride (7.87 g, 41.1 mmol) and 1-hydroxybenzotriazole hydrate (6.29 g, 41.1 mmol) in 50 ml of DMF. To the solution was added triethylamine (19.07 mL, 137 mmol). The reaction solution was stirred at 60° C. overnight and then cooled to room temperature. The reaction mixture was partitioned between water and ethyl acetate and transferred to a separatory funnel and washed with 10% LiCl, water, and brine. The organic phase was dried over anhydrous sodium sulfate, filtered and concentrated to provide dark oil. The crude product mixture was purified via ISCO (0%-50% of EtOAC/DCM in 15 minutes, 120 g column) to give 2-amino-3-cyclopropoxy-N-methoxy-N-methylbenzamide (5.2 g, 22.01 mmol, 64.3% yield). HPLC: RT=1.975 min (H₂O/MeOH with TFA, SunFire C18 3.5 μm, 2.1×30 mm, gradient=4 min, wavelength=220 nm); MS(ES):m/z=237.12 [M+H]⁺; ¹H NMR (400 MHz, chloroform-d) δ 7.17 (dd, J=8.0, 1.2 Hz, 1H), 7.02 (dd, J=7.9, 1.3 Hz, 1H), 6.67 (t, J=7.9 Hz, 1H), 4.78 (br. s., 2H), 3.88-3.73 (m, 1H), 3.69-3.56 (m, 3H), 3.36 (s, 3H), 0.92-0.72 (m, 4H)).

Intermediate B-7F: (2-Amino-3-cyclopropoxyphenyl)(3-fluorophenyl)methanone

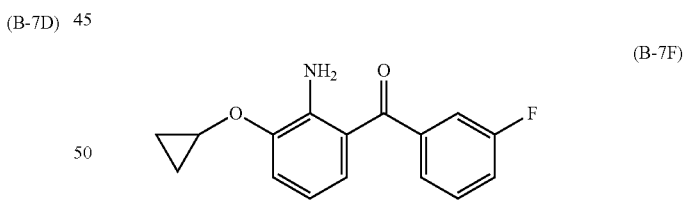

(B-7F)

A solution of 1-fluoro-3-iodobenzene (1.009 mL, 8.59 mmol) in tetrahydrofuran (100 mL) was cooled to −78° C. in a dry ice/acetone bath under nitrogen. Then a solution of n-BuLi (1.8 M in hexanes, 5.37 mL, 8.59 mmol) was added via syringe over 15 minutes and stirred for 60 minutes to give gave a dark-yellow suspension. Then a solution of 2-amino-3-cyclopropoxy-N-methoxy-N-methylbenzamide (0.58 g, 2.455 mmol) in 10 mL of THF was added via syringe and the reaction mixture was stirred for 40 minutes at −78° C. After 40 minutes the mixture was poured into a mixture of ice and 1N HCl and extracted into ethyl acetate to give a light-yellow solution. The organic layer was washed with water and brine and concentrated to give a dark-yellow oil residue. The crude product mixture was purified via ISCO (0%-100% of EtOAC/ heptane in 15 minutes, 40 g column) to give (2-amino-3-cyclopropoxyphenyl)(3-fluorophenyl)methanone (0.46 g, 1.696 mmol, 69.1% yield). HPLC: RT=3.481 min (H$_2$O/MeOH with TFA, SunFire C18 3.5 μm, 2.1×30 mm, gradient=4 min, wavelength=220 nm); MS(ES):m/z=272.16 [M+H]$^+$; $^1$H NMR (400 MHz, chloroform-d) δ 7.48-7.40 (m, 2H), 7.36 (ddd, J=9.3, 1.9, 1.1 Hz, 1H), 7.27-7.18 (m, 2H), 7.08 (dd, J=8.3, 1.2 Hz, 1H), 6.58 (t, J=8.0 Hz, 1H), 6.39 (br. s., 2H), 3.83 (t, J=4.5 Hz, 1H), 0.86 (d, J=4.4 Hz, 4H).

Intermediate B-7

Intermediate B-7 was synthesized from (2-amino-3-cyclopropoxyphenyl)(3-fluorophenyl)methanone following the procedure used for the synthesis of Intermediate B-1 to give 3-amino-9-cyclopropoxy-5-(3-fluorophenyl)-1H-benzo[e][1,4]diazepin-2(3H)-one. HPLC: RT=2.25 min (H$_2$O/MeOH with TFA, SunFire C18 3.5 μm, 2.1×30 mm, gradient=4 min, wavelength=254 nm); MS(ES):m/z=326.15 [M+H]$^+$; $^1$H NMR (400 MHz, methanol-d$_4$) δ 7.66-7.57 (m, 1H), 7.55-7.30 (m, 3H), 7.30-7.17 (m, 2H), 7.05-6.81 (m, 1H), 4.10-3.88 (m, 1H), 0.90 (dt, J=9.9, 2.8 Hz, 4H).

Intermediate B-8: 3-Amino-9-cyclopropoxy-5-phenyl-1H-benzo[e][1,4]diazepin-2(3H)-one

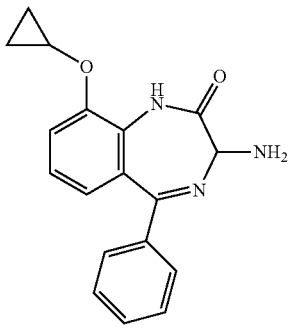

(B-8)

Intermediate B-8 was synthesized from 2-amino-3-cyclopropoxy-N-methoxy-N-methylbenzamide following the procedure described for the synthesis of Intermediate B-7 to give 3-amino-9-cyclopropoxy-5-phenyl-1H-benzo[e][1,4]diazepin-2(3H)-one. HPLC: RT=2.18 min (H$_2$O/MeOH with TFA, SunFire C18 3.5 μm, 2.1×30 mm, gradient=4 min, wavelength=254 nm); MS(ES):m/z=308.14 [M+H]$^+$; $^1$H NMR (400 MHz, methanol-d$_4$) δ 7.68-7.37 (m, 11H), 7.23 (t, J=8.0 Hz, 2H), 6.90 (dd, J=7.9, 1.3 Hz, 2H), 4.44 (s, 2H), 4.06-3.88 (m, 2H), 1.02-0.72 (m, 4H).

Intermediate B-9: (S)-3-Amino-9-methyl-5-phenyl-1H-benzo[e][1,4]diazepin-2(3H)-one

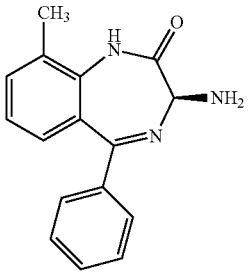

(B-9)

Intermediate B-9A: (S)-Benzyl (9-methyl-2-oxo-5-phenyl-2,3-dihydro-1H-benzo[e][1,4]diazepin-3-yl) carbamate

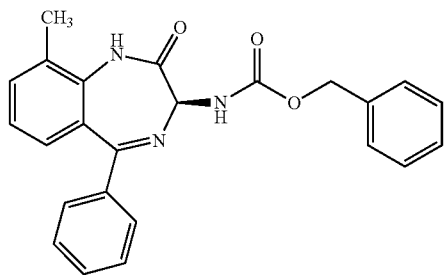

(B-9A)

A suspension of 2-(1H-benzo[d][1,2,3]triazol-1-yl)-2-(((benzyloxy)carbonyl)amino)acetic acid (17.30 g, 53.0 mmol) in THF (128 ml) and cooled to 0° C. Oxalyl chloride (4.64 ml, 53.0 mmol) was added, followed by 50 μL DMF. The reaction mixture was stirred for 2 h at 0° C. A solution of (2-amino-3-methylphenyl)(phenyl) methanone (5.09 g, 24.09 mmol) and N-methyl morpholine (7.95 ml, 72.3 mmol) was added, and the reaction mixture was allowed to warm gradually to room temperature. After 2.5 h ammonia (7 M in MeOH) (21.29 ml, 149 mmol) was added and the reaction mixture was stirred overnight. The resulting mixture was diluted with EtOAc (250 mL), and then washed with H$_2$O (250 mL), 1 M NaOH (250 mL), and brine (250 mL). The organic layer was concentrated and then suspended in acetic acid (48.2 ml). Ammonium acetate (9.29 g, 120 mmol) was added. After 2.5 hours, H$_2$O was added to precipitate the product resulting in a sticky solid. The solid was collected by filtration and suspended in a minimal amount of MeOH and cooled to 0° C. The resulting white solid was collected by filtration, washed with cold MeOH and then diethyl ether. The resulting material was dried under vacuum. The mixture of enantiomers was separated using SFC to afford the desired compound: (S)-benzyl (9-methyl-2-oxo-5-phenyl-2,3-dihydro-1H-benzo[e][1,4]diazepin-3-yl)carbamate (1.6 g, 16.63%). HPLC RT=2.773 min (CHROMOLITH® SpeedROD, 5.0 μm, 4.6 mm×50 mm, 10-90% aqueous methanol containing 0.1% TFA, 4 min gradient, monitored at 220 nm). [M+H$^+$]=400.4. $^1$H NMR (400 MHz, DMSO-d$_6$) δ 8.35 (d, J=8.6 Hz, 1H), 7.56-7.37 (m, 11H), 7.23-7.17 (m, 1H), 7.16-7.12 (m, 1H), 5.12-4.99 (m, 3H), 2.42 (s, 3H).

Intermediate B-9

A solution of (S)-benzyl (9-methyl-2-oxo-5-phenyl-2,3-dihydro-1H-benzo[e][1,4]diazepin-3-yl)carbamate (1.6 g, 4.01 mmol) in 33% HBr in HOAc (6.59 ml, 40.1 mmol) was stirred at room temperature for 2 h. Ether (100 mL) was added and the resulting yellow suspension was cooled to 0° C. for 1 h. The resulting solid was collected by filtration and rinsed with ether. The hygroscopic solid was then dissolved in MeOH, concentrated to dryness and dried under vacuum. The solid (HBr salt) was triturated and sonicated with hexane (with a little of EtOAc, to remove residual HOAc), the solid was collected by filtration, and dried under vacuum to afford the desired product. HPLC RT=1.378 min (CHROMOLITH® SpeedROD, 5.0 μm, 4.6 mm×50 mm, 10-90% aqueous methanol containing 0.1% TFA, 4 min gradient, monitored at 220 nm). [M+H+]=266.4. $^1$H NMR (400 MHz, DMSO-d$_6$) δ 10.63 (s, 1H), 8.99 (br. s., 3H), 7.64-7.45 (m, 6H), 7.28-7.22 (m, 1H), 7.20-7.15 (m, 1H), 5.05 (d, J=4.6 Hz, 1H), 2.43 (s, 3H).

Intermediate B-10: (S)-3-Amino-9-methoxy-5-phenyl-1H-benzo[e][1,4]diazepin-2(3H)-one

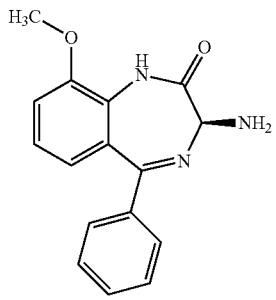
(B-10)

Intermediate B-10A:
8-Methoxy-2-methyl-4H-benzo[d][1,3]oxazin-4-one

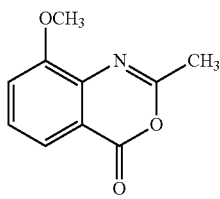
(B-10A)

In a 100 mL round-bottomed flask was 2-amino-3-methoxybenzoic acid (10.1 g, 60.4 mmol) and acetic anhydride (50 ml, 530 mmol) to give a suspension. The mixture was heated to 140° C. with stirring for 180 min. The reaction mixture was cooled to room temperature and concentrated to provide 8-methoxy-2-methyl-4H-benzo[d][1,3]oxazin-4-one (11.51 g, 100%). $^1$H NMR (400 MHz, DMSO-d$_6$) δ 7.59 (dd, J=6.9, 2.3 Hz, 1H), 7.52-7.42 (m, 2H), 3.89 (s, 3H), 2.39 (s, 3H); HPLC: RT=0.795 min (H$_2$O/MeOH with TFA, SunFire C18 2.5 μm, 2.1×30 mm, gradient=2 min, wavelength=220); MS(ES): m/z=292 [M+H]$^+$.

Intermediate B-10B:
(2-Amino-3-methoxyphenyl)(phenyl)methanone

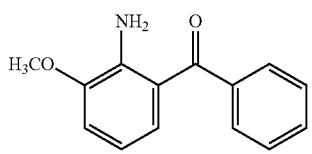
(B-10B)

A 100 mL round-bottomed flask containing 8-methoxy-2-methyl-4H-benzo[d][1,3]oxazin-4-one (1 g, 5.23 mmol) in diethyl ether (20 mL), toluene (10 mL) and THF (10 mL) was cooled to 0° C. Phenyl magnesium bromide (1.9 mL, 5.75 mmol, 3M in Et$_2$O) was added in one portion. The reaction mixture was allowed to warm to room temperature and stirred overnight. The reaction mixture was cooled to 0° C. and 30 g crushed ice and 25 ml 6N HCl were added. The reaction mixture was allowed to slowly warm to room temperature. The reaction mixture was partitioned with ethyl acetate (100 mL) and brine (50 mL). The aqueous phase was separated and extracted with ethyl acetate (1×100 mL). The combined organic layers were dried (MgSO$_4$), filtered and concentrated. The residue was purified by silica gel chromatography to provide 882 mg colorless solid. This material was dissolved in AcOH (10 mL) and treated with concentrated HCl (6 mL, 72.0 mmol), then heated to 100° C. with stirring overnight. The reaction mixture was cooled to room temperature, concentrated and dried under vacuum. The residue was diluted with ethyl acetate (100 mL), the pH was adjusted to pH 10 with saturated NaHCO$_3$, and then the phases separated. The aqueous phase was extracted with ethyl acetate (2×50 mL), the combined organic phases were dried (MgSO$_4$), filtered and concentrated. The residue was purified by silica gel chromatography (EtOAc/hexane) to provide (2-amino-3-methoxyphenyl)(phenyl) methanone (370 mg, 31%): $^1$H NMR (400 MHz, DMSO-d$_6$) δ 9.43 (br. s., 2H), 7.70-7.63 (m, 1H), 7.33-7.22 (m, 5H), 7.10-7.03 (m, 1H), 6.91 (dd, J=6.7, 2.1 Hz, 1H), 3.87 (s, 3H): HPLC: RT=1.888 min (H$_2$O/MeOH with TFA, SunFire C18 2.5 μm, 2.1×30 mm, gradient=2 min, wavelength=220); MS(ES): m/z=228[M+H]$^+$.

Intermediate B-10

Intermediate B-10 was synthesized from (2-amino-3-methoxyphenyl)(phenyl)methanone following the procedure described for Intermediate B-1 to give racemic 3-amino-9-methoxy-5-phenyl-1H-benzo[e][1,4]diazepin-2(3H)-one, which was resolved by chiral SFC (Instrument: Berger SFC MGII, Column: CHIRALPAK® AS 25×3 cm, 5 μm; column temp: 45° C.; Mobile Phase: CO$_2$/MeOH-0.1DEA (67/33); Flow rate: 85 mL/min; Detection at 220 nm.) to give Intermediate B-10: (S)-3-amino-9-methoxy-5-phenyl-1H-benzo[e][1,4]diazepin-2(3H)-one. MS(ES): m/z=282.1 [M+H]$^+$. HPLC: RT=3.21 min (Luna C18 4.6×30 mm 3 μm H$_2$O/MeOH/TFA, gradient=5 min, wavelength=220 nm).

Intermediate B-11: (S)-3-Amino-9-fluoro-5-phenyl-1H-benzo[e][1,4]diazepin-2(3H)-one

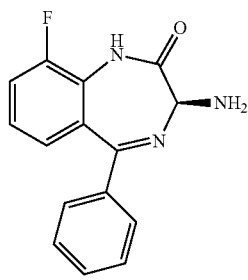
(B-11)

Intermediate B-11 was synthesized from (2-amino-3-fluorophenyl)(phenyl)methanone following the procedure described for Intermediate B-10 to give after chiral SFC (Instrument: Berger SFC MGII, Column: CHIRALPAK® AS 25×3 cm, 5 µm; column temp: 45° C.; Mobile Phase: CO$_2$/MeOH-0.1DEA (67/33); Flow rate: 85 mL/min; Detection at 220 nm.) to give Intermediate B-11: (S)-3-amino-9-fluoro-5-phenyl-1H-benzo[e][1,4]diazepin-2(3H)-one. MS(ES): m/z=270 [M+H]$^+$. HPLC: RT=1.29 min (H$_2$O/MeOH with TFA, CHROMOLITH® ODS S5, 4.6×50 mm, gradient=4 min, wavelength=220 nm).

Intermediate B-12: 3-Amino-9-chloro-5-phenyl-1H-benzo[e][1,4]diazepin-2(3H)-one

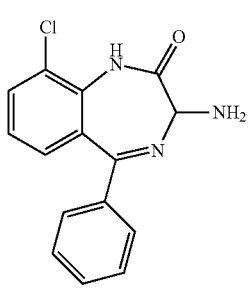

(B-12)

Intermediate B-12 was synthesized from (2-amino-3-chlorophenyl)(phenyl)methanone following the procedure used for the synthesis of Intermediate B-1 to give 3-amino-9-chloro-5-phenyl-1H-benzo[e][1,4]diazepin-2(3H)-one: MS(ES):m/z=286 [M+H$^+$]. HPLC: RT=0.63 min (H$_2$O/CH$_3$CN with 0.05% TFA, BEH C18 1.7 µm, 2.1×50 mm, gradient (2%-98%)=1 min, wavelength=220.

Intermediate B-13: 3-Amino-9-fluoro-5-(m-tolyl)-1H-benzo[e][1,4]diazepin-2(3H)-one

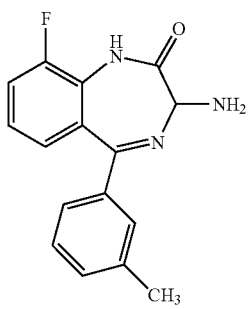

(B-13)

Intermediate B-13 was synthesized from (2-amino-3-chlorophenyl)(m-tolyl) methanone following the procedure used for the synthesis of Intermediate B-1 to give 3-amino-9-fluoro-5-(m-tolyl)-1H-benzo[e][1,4]diazepin-2(3H)-one: MS(ES):m/z=284 [M+H$^+$]. HPLC: RT=0.61 min H$_2$O/MeOH with TFA, BEH C18 1.7 µm, 2.1×50 mm, gradient=2 min, wavelength=220 nm. $^1$H NMR (400 MHz, methanol-d$_4$) δ 7.48-7.38 (m, 2H), 7.36-7.27 (m, 3H), 7.26-7.19 (m, 1H), 7.12 (d, J=7.9 Hz, 1H), 4.45 (s, 1H), 2.37 (s, 3H).

Intermediate B-14: (S)-7-Amino-9-phenyl-5H-[1,3]dioxolo[4',5':4,5]benzo[1,2-e][1,4]diazepin-6(7H)-one

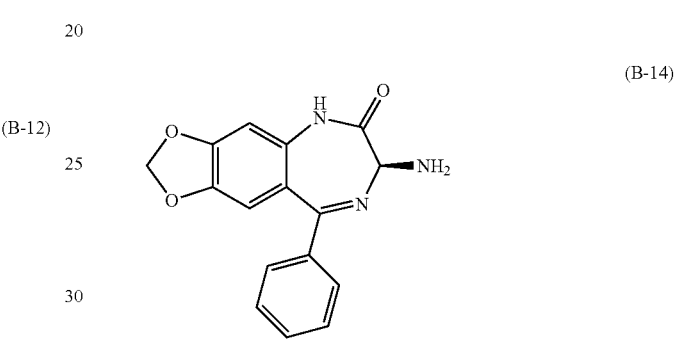

(B-14)

Intermediate B-14 was synthesized from (6-aminobenzo[d][1,3]dioxol-5-yl)(phenyl)-methanone following the procedure used for the synthesis of Intermediate B-2 to give (S)-7-amino-9-phenyl-5H-[1,3]dioxolo[4',5':4,5]benzo[1,2-e][1,4]diazepin-6(7H)-one: MS(ES):m/z=296 [M+H$^+$]. HPLC: RT=1.24 min (H$_2$O/CH$_3$CN with TFA, SunFire C18 3.5 µm, 2.1×30 mm, gradient=2 min, wavelength=220 nm).

Intermediate B-15: (S)-3-Amino-5-phenyl-1-(pyridin-2-yl)-1H-benzo[e][1,4]diazepin-2(3H)-one

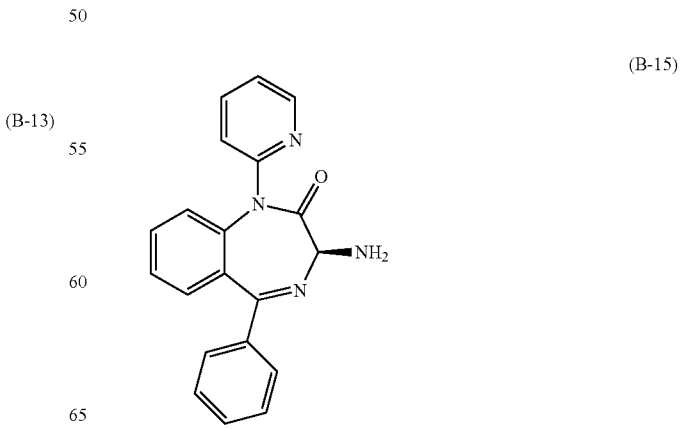

(B-15)

Intermediate B-15A: Benzyl 2-oxo-5-phenyl-1-(pyridin-2-yl)-2,3-dihydro-1H-benzo[e][1,4]diazepin-3-ylcarbamate

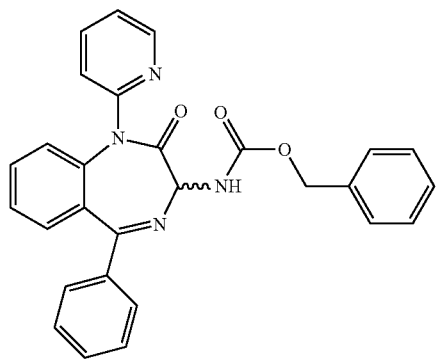

(B-15A)

To a stirred mixture of benzyl 2-oxo-5-phenyl-2,3-dihydro-1H-benzo[e][1,4]diazepin-3-ylcarbamate (1.20 g, 3.11 mmol, prepared according to *J. Med. Chem.*, 49:2311-2319 (2006), compound #4a), 2-iodopyridine (1.00 g, 4.88 mmol), cuprous iodide (0.15 g, 0.788 mmol) and $Cs_2CO_3$ (3.05 g, 9.36 mmol) were combined in dioxane (25 mL). To this mixture was added (+/−)-trans-1,2-diaminocyclohexane (0.19 mL, 1.58 mmol) under nitrogen. The reaction mixture was then heated to 120° C. and gently refluxed for 10 min. It was then cooled to room temperature under nitrogen. This mixture was diluted with 100 mL of EtOAc, 40 mL of pH 4 phosphate buffer and 40 mL of saturated $NaHCO_3$ solution. The insoluble material was removed by filtration through a 2' pad of CELITE®, and rinsed with EtOAc (2×30 mL). The aqueous phase was separated and extracted with 160 mL of EtOAc. The combined EtOAc extracts were washed with saturated $NaHCO_3$ solution (1×30 mL) and brine (1×20 mL), then dried ($MgSO_4$), filtered and concentrated in vacuo. The residue was purified by silica gel chromatography (hexane/EtOAc) to afford benzyl 2-oxo-5-phenyl-1-(pyridin-2-yl)-2,3-dihydro-1H-benzo[e][1,4]diazepin-3-ylcarbamate (0.88 g, 61%): $^1$H NMR (400 MHz, DMSO-$d_6$) δ 8.61 (1H, d, J=8.14 Hz), 8.47 (1H, dd, J=4.73, 1.21 Hz), 7.94-8.03 (1H, m), 7.64 (2H, d, J=7.92 Hz), 7.47-7.60 (4H, m), 7.27-7.44 (9H, m), 6.97 (1H, d, J=8.14 Hz), 5.39 (1H, d, J=8.36 Hz), 5.10 (2H, s); HPLC: RT=2.930 min (CHROMOLITH® ODS 4.6×50 mm (4 min grad) eluting with 10-90% aqueous MeOH over 4 minutes containing 0.0% TFA, 4 mL/min, monitoring at 220 nm); MS(ES): m/z=463.3 [M+H]$^+$.

Intermediate B-15

Benzyl 2-oxo-5-phenyl-1-(pyridin-2-yl)-2,3-dihydro-1H-benzo[e][1,4]diazepin-3-ylcarbamate (5.24 g, 11.33 mmol) and 33% HBr/HOAc (50 mL, 11.33 mmol) were combined and stirred at room temperature for 2 h. The reaction mixture was diluted with 300 mL of ether. The resulting precipitate was collected by filtration, rinsed with ether (2×50 mL), and then dried under vacuum. The solid was dissolved in 100 mL of water and made basic by the addition of solid $NaHCO_3$. The mixture was extracted with EtOAc (2×200 mL), and the combined organic extracts were washed with water (1×40 mL) and brine (1×50 mL), then dried ($MgSO_4$), filtered and concentrated in vacuo to give the crude racemic amine. Preparative SFC chromatography (Berger SFC MGII, AD-H 250×30 mm ID, 5 μm, 78/22 $CO_2$/MeOH with 0.1% DEA, 85 mL/min) gave Intermediate B-15 (1.576 g, 42.4%) as a colorless solid. $^1$H NMR (400 MHz, DMSO-$d_6$) δ 8.47 (1H, dd, J=4.73, 1.65 Hz), 7.98 (1H, td, J=7.70, 1.98 Hz), 7.62 (3H, dd, J=14.75, 7.48 Hz), 7.45-7.57 (5H, m), 7.26-7.43 (3H, m), 6.92 (1H, d, J=8.14 Hz), 4.57 (1H, br. s.), 2.67 (1H, br. s.); Chiral HPLC: RT=5.160 min (Berger SFC, AD-H 250×4.6 mm ID, 5 μm, 75/25 $CO_2$/MeOH with 0.1% DEA, 2.0 mL/min); HPLC: RT=1.290 min (CHROMOLITH® ODS 4.6×50 mm (4 min grad) eluting with 10-90% aqueous MeOH over 4 minutes containing 0.0% TFA, 4 mL/min, monitoring at 220 nm); MS(ES): m/z=329.0 [M+H]$^+$.

Intermediate B-16: (S)-3-Amino-5-phenyl-1-(5-chloropyridin-2-yl)-1H-benzo[e][1,4]diazepin-2(3H)-one

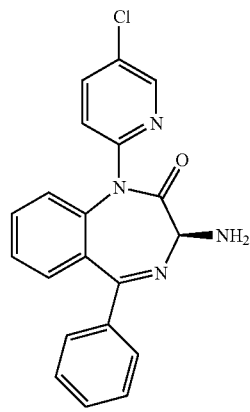

(B-16)

Intermediate B-16 was prepared from benzyl 2-oxo-5-phenyl-2,3-dihydro-1H-benzo[e][1,4]diazepin-3-ylcarbamate and 5-chloro-2-iodopyridine according to the procedure described for Intermediate B-15. RT=2.430 min ($H_2O$/$CH_3OH$ with TFA, CHROMOLITH® ODS S5 4.6×50 mm, gradient=3 min, wavelength=220 and 254 nm); MS(ES):m/z=363.12 [M+H]$^+$].

Intermediate B-17: (S)-3-Amino-1-(5-methoxypyridin-2-yl)-5-phenyl-1H-benzo[e][1,4]diazepin-2(3H)-one

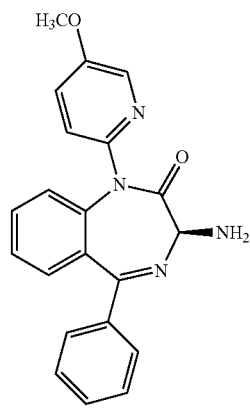

(B-17)

Intermediate B-17 was prepared according to the procedure shown for Intermediate B-15 after preparative SFC chromatography (Berger SFC MGII, CHIRALCEL® AS-H 25×3 cm ID, 5 µm, 83/17 CO$_2$/MeOH w/0.1% DEA) to give Intermediate B-17 (0.51 g, 43.6%) as a colorless solid: $^1$H NMR (400 MHz, DMSO-d$_6$) δ 8.17 (d, J=2.9 Hz, 1H), 7.65-7.60 (m, 2H), 7.58-7.45 (m, 6H), 7.37-7.25 (m, 2H), 6.92 (d, J=7.7 Hz, 1H), 4.54 (s, 1H), 3.86 (s, 3H), 2.62 (s, 2H); Chiral HPLC: RT=3.889 min (Berger SFC, AS-H 250×4.6 mm ID, 5 µm, 75/25 CO$_2$/MeOH with 0.1% DEA, 2.0 mL/min); HPLC: RT=2.16 min (CHROMOLITH® ODS 4.6×50 mm (4 min grad) eluting with 10-90% aqueous MeOH over 4 minutes containing 0.0% TFA, 4 mL/min, monitoring at 220 nm); MS(ES): m/z=359.2 [M+H]$^+$.

Intermediate B-18: (S)-3-Amino-1-(6-methoxypyridin-2-yl)-5-phenyl-1H-benzo[e][1,4]diazepin-2(3H)-one

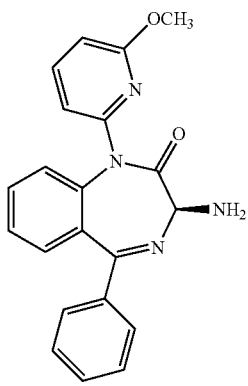
(B-18)

Intermediate B-18 was prepared according to the procedure shown for Intermediate B-15. After preparative SFC chromatography (Instrument: Berger SFC MGII, Column: CHIRALPAK® AS-H 25×3 cm, 5 µm; Mobile Phase: CO$_2$/MeOH-0.1DEA (83/17); Flow rate: 85 mL/min; Detection at 220 nm.), Intermediate B-18 was obtained as a colorless solid: Chiral HPLC: RT=3.44 min (Berger SFC, AS-H 250× 4.6 mm ID, 5 µm, 75/25 CO$_2$/MeOH with 0.1% DEA, 2.0 mL/min); HPLC: RT=2.07 min (CHROMOLITH® ODS 4.6×50 mm (4 min grad) eluting with 10-90% aqueous MeOH over 4 minutes containing 0.0% TFA, 4 mL/min, monitoring at 220 nm); MS(ES): m/z=359.2 [M+H]$^+$.

Intermediate B-19: 3-Amino-9-methoxy-2-oxo-5-phenyl-2,3-dihydro-1H-benzo[e][1,4]diazepine-7-carbonitrile

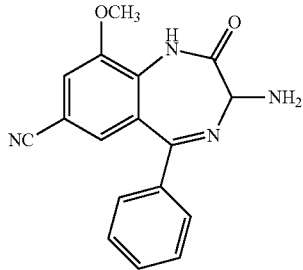
(B-19)

Intermediate B-19A: tert-Butyl (7-bromo-9-methoxy-2-oxo-5-phenyl-2,3-dihydro-1H-benzo[e][1,4]diazepin-3-yl)carbamate (B-19A)

To a suspension of 3-amino-7-bromo-9-methoxy-5-phenyl-1H-benzo[e][1,4]diazepin-2(3H)-one (200 mg, 0.555 mmol) in dioxane (5 mL) at room temperature was added di-t-butyldicarbonate (0.140 mL, 0.611 mmol), followed by triethylamine (0.085 mL, 0.611 mmol). The suspension was stirred at overnight, and then the reaction mixture was concentrated. The crude material was purified by silica gel chromatography (hexanes/EtOAc) to give tert-butyl (7-bromo-9-methoxy-2-oxo-5-phenyl-2,3-dihydro-1H-benzo[e][1,4]diazepin-3-yl)carbamate: (240 mg, 0.516 mmol, 93% yield): HPLC RT=4.301 min (H$_2$O/MeOH with H$_3$PO$_4$, SunFire C18, 5.0 µm, 4.6 mm×50 mm, 4 min gradient, monitored at 220 nm). [M+H$^+$]=461; $^1$H NMR (400 MHz, DMSO-d$_6$) δ 10.15 (1H, s), 7.76 (1H, d, J=8.58 Hz), 7.40-7.57 (7H, m), 6.97 (1H, d, J=1.76 Hz), 5.01 (1H, d, J=8.58 Hz), 3.95 (3H, s), 1.41 (10H, s).

Intermediate B-19B: tert-Butyl 7-cyano-9-methoxy-2-oxo-5-phenyl-2,3-dihydro-1H-benzo[e][1,4]diazepin-3-ylcarbamate

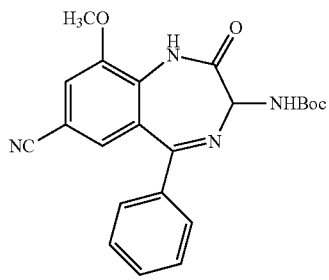
(B-19B)

tert-Butyl (7-bromo-9-methoxy-2-oxo-5-phenyl-2,3-dihydro-1H-benzo[e][1,4]diazepin-3-yl)carbamate (0.050 g, 0.109 mmol), zinc cyanide (0.013 g, 0.109 mmol), and Pd(Ph$_3$P)$_4$ (0.013 g, 10.86 µmol) were dissolved in DMA (0.543 ml) and heated to 90° C. After 1 h, the reaction was quenched with saturated NaHCO$_3$. The reaction mixture was extracted three times with EtOAc. The combined organic layers were dried with MgSO$_4$ and evaporated. The residue was purified by silica gel chromatography (hexanes/EtOAc) to give tert-butyl 7-cyano-9-methoxy-2-oxo-5-phenyl-2,3-dihydro-1H-benzo[e][1,4]diazepin-3-ylcarbamate (41 mg, 93%): HPLC RT=1.948 min (H$_2$O/MeOH with TFA, SunFire C18, 5.0 μm, 2.1 mm×30 mm, 4 min gradient, monitored at 220 nm). [M+H$^+$]=407.

Intermediate B-19 tert-Butyl 7-cyano-9-methoxy-2-oxo-5-phenyl-2,3-dihydro-1H-benzo[e][1,4]diazepin-3-ylcarbamate (0.441 g, 1.086 mmol) was dissolved in DCM (4 ml) and TFA (1 ml, 12.98 mmol) and stirred at room temperature for 1.5 h. TFA (1 ml, 12.98 mmol) was added, and the reaction mixture was stirred overnight. The reaction mixture was concentrated, then dissolved in EtOAc and washed with saturated NaHCO$_3$. The aqueous layer was extracted twice more, then the organic layers were dried with Na$_2$SO$_4$ and evaporated. The residue was purified silica gel chromatography (DCM/MeOH). The fractions containing product were evaporated, then the material was triturated with EtOAc to give 3-amino-9-methoxy-2-oxo-5-phenyl-2,3-dihydro-1H-benzo[e][1,4]diazepine-7-carbonitrile (Intermediate B-19). $^1$H NMR (400 MHz, chloroform-d) δ 7.54-7.45 (m, 3H), 7.42-7.37 (m, 2H), 7.26 (d, J=1.8 Hz, 1H), 7.22 (d, J=1.5 Hz, 1H), 4.46 (s, 1H), 4.01 (s, 3H), 2.45 (br. s., 2H).

Intermediate S-1: (R)-2-((R)-2-(tert-Butoxy)-2-oxo-1-phenylethyl)-5,5,5-trifluoropentanoic acid

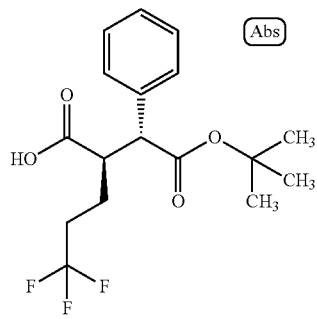

Intermediate S-1A: tert-Butyl 2-phenylacetate

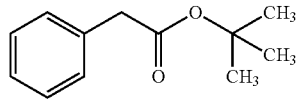

A solution of 2-phenylacetic acid (12 g, 88 mmol) in tBuOAc (250 mL) in a 1 L round-bottomed flask was treated with perchloric acid, 70% redistilled (0.212 mL, 3.53 mmol), and stirred at room temperature for 20 hours. The solution was transferred very slowly to stirred mixture of saturated aqueous NaHCO$_3$ and Et$_2$O, which resulted in bubbling. The resulting layers were separated and the organic layer washed with saturated aqueous NaHCO$_3$, dried over MgSO$_4$, filtered, and concentrated to give tert-butyl 2-phenylacetate (11.6 g, 68% yield). $^1$H NMR (500 MHz, chloroform-d) δ 7.34-7.29 (m, 2H), 7.28-7.22 (m, 3H), 3.52 (s, 2H), 1.44 (s, 9H).

Intermediate S-1B: (2R,3R)-1-Benzyl 4-tert-butyl 3-phenyl-2-(3,3,3-trifluoropropyl) succinate

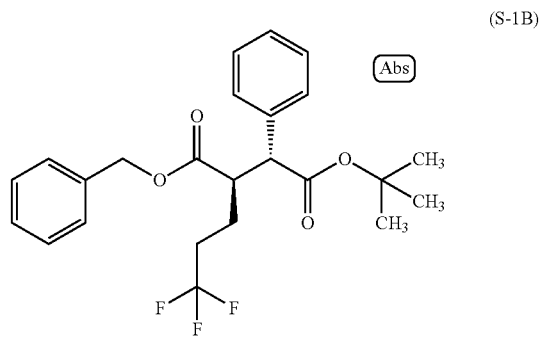 [SMILES: CC(C)(C)OC(=O)[C@@H](c1ccccc1)[C@@H](CCC(F)(F)F)C(=O)OCc1ccccc1]

A solution of tert-butyl 2-phenylacetate (8.5 g, 44.2 mmol) in THF (400 mL) in a 1 L round-bottomed flask was cooled in −78° C. bath and treated with a solution of KHMDS, 0.5M in toluene (97 mL, 48.6 mmol) via cannula over 10 minutes. After 10 minutes the mixture was removed from the bath and placed in a room temperature water bath and stirred for 15 minutes and then again cooled in −78° C. bath. After 15 minutes a solution of Preparation 4D (R)-benzyl 5,5,5-trifluoro-2-(((trifluoromethyl)sulfonyl)oxy)pentanoate (19.18 g, 48.6 mmol) in THF (50 mL) in a 100 ml, round bottom flask was added over 10 min via cannula with a 20 mL THF rinse. The reaction mixture turned cloudy. The reaction mixture was stirred at −78° C. for 1 hour and then quenched with saturated aqueous NH$_4$Cl. The mixture was removed from −78° C. bath, diluted with 10% LiCl aq and extracted with Et$_2$O. The organic layer was dried over MgSO$_4$, filtered and concentrated. The resulting light brown residue was dissolved in 100 mL CH$_2$Cl$_2$ and treated with charcoal and MgSO$_4$. The mixture was filtered to give an almost colorless solution. The CH$_2$Cl$_2$ solution was concentrated and diluted with hexane and cooled in −20° C. freezer. The resulting solids were filtered and rinsed with cold hexane (containing 5% MTBE) and dried on a fitted filter funnel under a stream of nitrogen to give 8.16 g. The solid was triturated with 40 mL hexane and 4 mL MTBE stirring the white suspension at room temperature for 1 hour and then cooling at −20° C. for 3 hours before filtering the white solid and washing with cold solvent (10:1 hexane:MTBE) to give (2R,3R)-1-benzyl 4-tert-butyl 3-phenyl-2-(3,3,3-trifluoropropyl)succinate (7.16 g, 37% yield) as a white solid. $^1$H NMR (500 MHz, chloroform-d) δ 7.32-7.23 (m, 8H), 7.05-6.97 (m, 2H), 4.89-4.76 (m, 2H), 3.69 (d, J=11.4 Hz, 1H), 3.23 (ddd, J=11.2, 9.9, 3.9 Hz, 1H), 2.19-2.04 (m, 2H), 2.03-1.88 (m, 2H), 1.40 (s, 9H).

Intermediate S-1

In a 250 mL round-bottomed flask a suspension of (2R,3R)-1-benzyl 4-tert-butyl 3-phenyl-2-(3,3,3-trifluoropropyl) succinate (7.16 g, 16.40 mmol) and Pd/C, 10% (1.746 g, 1.640 mmol) in ethyl acetate (35 mL) and MeOH (35 mL) was hydrogenated using a hydrogen filled balloon while stirring at room temperature. When the reaction was complete (followed by HPLC), the suspension was filtered through 0.45 μm membrane and rinsed with MeOH and EtOAc. The filtrate was concentrated and dried under vacuum to give Intermediate S-1 (5.65 g, 99% yield). MS (m−1)=345. $^1$H NMR (500 MHz, DMSO-$d_6$) δ 7.37-7.26 (m, 5H), 3.67 (d, J=10.5 Hz, 1H), 3.04 (td, J=10.3, 3.7 Hz, 1H), 2.38-2.20 (m, 2H), 1.88-1.70 (m, 2H), 1.37 (s, 9H).

Intermediate S-2: (R)-2-((R)-2-tert-Butoxy-1-(3-methylisoxazol-4-yl)-2-oxoethyl)-5,5,5-trifluoropentanoic acid

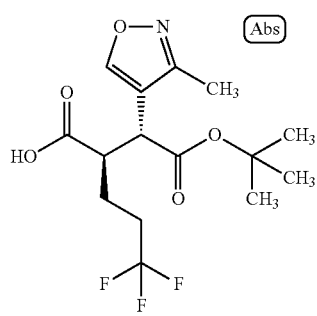

(S-2)

Intermediate S-2A: (2R,3R)-1-Benzyl 4-tert-butyl 3-(3-methylisoxazol-4-yl)-2-(3,3,3-trifluoropropyl)succinate

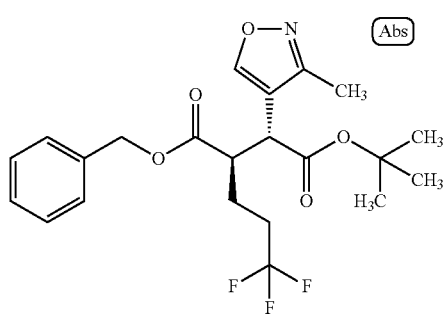

(S-2A)

In a 250 mL round-bottomed flask a solution of tert-butyl 2-(3-methylisoxazol-4-yl)acetate (1.75 g, 8.87 mmol) in THF (56 mL) and toluene (27 mL) was cooled in −78° C. bath and treated with a solution of 1M KHMDS (11.09 mL, 11.09 mmol) in THF dropwise over 2 minutes via syringe. After stirring for 15 minutes at −78° C., the reaction mixture was placed in a room temperature water bath for 15 minutes and then again in −78° C. bath for another 15 minutes before a solution of Preparation 4D (R)-benzyl 5,5,5-trifluoro-2-(trifluoromethylsulfonyloxy)pentanoate (4.55 g, 11.53 mmol) in 6 mL THF and 3 mL toluene was added to the reaction over 2 minutes. The reaction mixture was stirred in −78° C. bath for 2 hours before being quenched with saturated aqueous NH$_4$Cl and then warmed to room temperature. The mixture was diluted with brine and extracted with EtOAc. The organic layer was dried over MgSO$_4$ filtered and concentrated. The residue was purified on silica gel column (330 g ISCO) eluting with a gradient of 0-30% EtOAc/CH$_2$Cl$_2$, and collected tubes containing product were concentrated to give (2R,3R)-1-benzyl 4-tert-butyl 3-(3-methylisoxazol-4-yl)-2-(3,3,3-trifluoropropyl)succinate (2.394 g, 61% yield) containing about 30% of the (2R,3S) isomer.

Intermediate S-2

In a 200 mL round-bottomed flask a colorless solution of (2R,3R)-1-benzyl 4-tert-butyl 3-(3-methylisoxazol-4-yl)-2-(3,3,3-trifluoropropyl)succinate (2.4 g, 5.44 mmol) in MeOH (Volume: 50 mL) was treated with Pearlman's Catalyst (0.076 g, 0.544 mmol) and hydrogenated using a hydrogen-filled balloon at room temperature for 1 hour until reaction was complete (monitored by HPLC). The mixture was filtered reaction through 0.45 μm membrane with rinsed with MeOH. The filtrated was concentrated to give 2.03 g of crude solid. The solid was purified on Prep HPLC [C18 Luna 30×100 eluting with a gradient from 10% B to 100% B (15 min)] to give 99% pure Intermediate S-2 (896 mg, 46% yield) as a white solid. MS(ES):m/z=352 [M+H$^+$], m/z=350[M−H$^-$]. $^1$H NMR (500 MHz, chloroform-d) δ 8.40 (s, 1H), 3.62 (d, J=10.0 Hz, 1H), 3.08 (td, J=10.0, 3.6 Hz, 1H), 2.34 (s, 3H), 2.33-2.14 (m, 2H), 2.03-1.89 (m, 2H), 1.46 (s, 9H).

Intermediate S-3: (R)-2-((R)-2-tert-Butoxy-2-oxo-1-(pyridin-3-yl)ethyl)-5,5,5-trifluoropentanoic acid

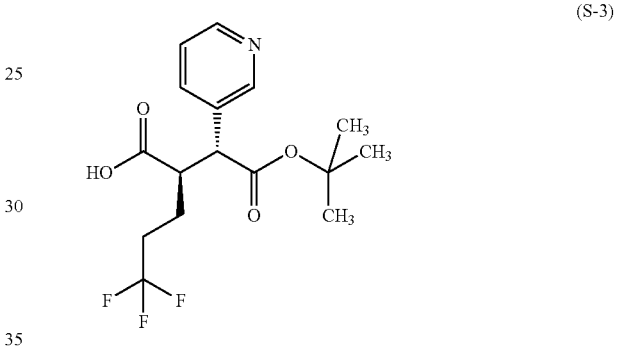

(S-3)

Intermediate S-3 was synthesized from tert-butyl 2-(pyridin-3-yl)acetate (100 mg, 0.517 mmol) and (R)-benzyl 5,5,5-trifluoro-2-(trifluoromethylsulfonyloxy)pentanoate (245 mg, 0.621 mmol) using the procedure described for Intermediate S-2 to give Intermediate S-3 (60 mg, 0.173 mmol) as a white solid containing about 30% of the (R, S) isomer. MS(ES):m/z=483.3 [M+H$^+$].

Intermediate S-4: (R)-2-((R)-2-(tert-Butoxy)-1-(4-chlorophenyl)-2-oxoethyl)-5,5,5-trifluoropentanoic acid

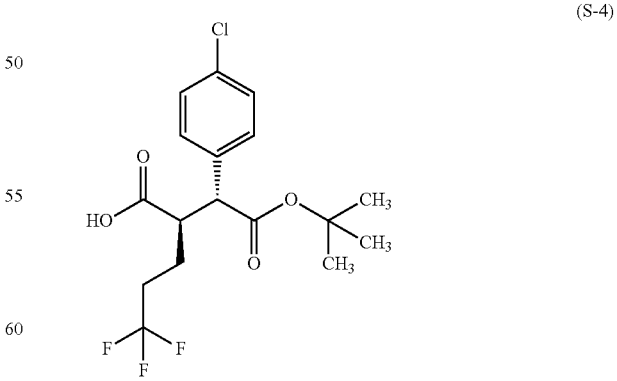

(S-4)

Intermediate S-4 was synthesized from tert-butyl 2-(4-chlorophenyl)acetate (20 mg, 0.088 mmol) and (2R,3R)-1-benzyl 4-tert-butyl 3-(4-chlorophenyl)-2-(3,3,3-trifluoropropyl)succinate (37 mg, 0.079 mmol, 89% yield) using the procedure described for the synthesis of Intermediate S-1 to afford Intermediate S-4 (30 mg, 88%) as a white solid containing about 30% of the (R, S) isomer. MS(ES):m/z=379.4 [M−H⁻].

Example 5

(2R,3R)—N1-((S)-5-(3-Fluorophenyl)-9-methyl-2-oxo-2,3-dihydro-1H-benzo[e][1,4]diazepin-3-yl)-3-phenyl-2-(3,3,3-trifluoropropyl)succinamide

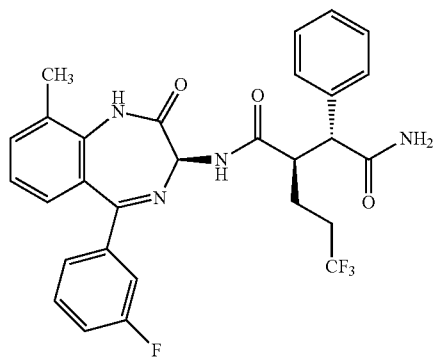

Intermediate 5A: (2R,3R)-tert-Butyl 6,6,6-trifluoro-3-((5-(3-fluorophenyl)-9-methyl-2-oxo-2,3-dihydro-1H-benzo[e][1,4]diazepin-3-yl)carbamoyl)-2-phenylhexanoate

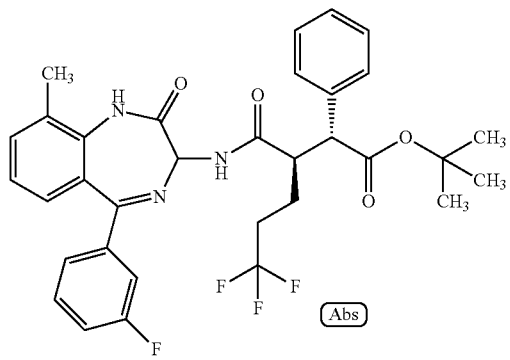

In a 20 ml scintillation vial was added Intermediate B-1 (100 mg, 0.275 mmol), Intermediate S-1 (95 mg, 0.275 mmol), and TBTU (176 mg, 0.549 mmol) in DMF (2 mL). The mixture was treated with TEA (0.115 mL, 0.824 mmol) and stirred at room temperature for 2 hours. The mixture was diluted with water and the solid suspension was extracted into ethyl acetate, washed with water, and concentrated to give (2R,3R)-tert-butyl 6,6,6-trifluoro-3-((5-(3-fluorophenyl)-9-methyl-2-oxo-2,3-dihydro-1H-benzo[e][1,4]diazepin-3-yl)carbamoyl)-2-phenylhexanoate as a light tan solid. MS(ES): m/z=612.1 [M+H⁺].

Intermediate 5B: (2R,3R)-6,6,6-Trifluoro-3-((5-(3-fluorophenyl)-9-methyl-2-oxo-2,3-dihydro-1H-benzo[e][1,4]diazepin-3-yl)carbamoyl)-2-phenylhexanoic acid

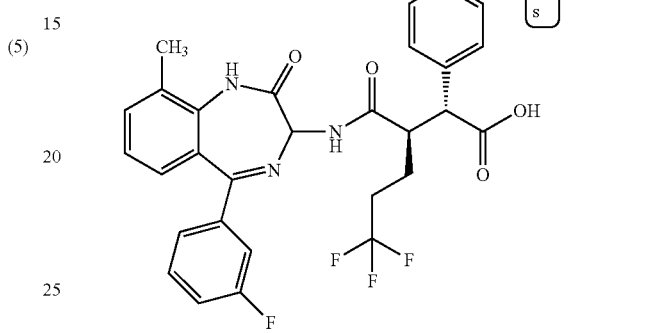

A solution of (2R,3R)-tert-butyl 6,6,6-trifluoro-3-((5-(3-fluorophenyl)-9-methyl-2-oxo-2,3-dihydro-1H-benzo[e][1,4]diazepin-3-yl)carbamoyl)-2-phenylhexanoate (168 mg, 0.275 mmol) in dichloromethane (2 mL) was treated with TFA (2 mL) and allowed to stand at room temperature for 3 hours. The mixture was diluted with DCM and evaporated to dryness. The residue was dissolved in DCM and washed with water and concentrated to give (2R,3R)-6,6,6-trifluoro-3-((5-(3-fluorophenyl)-9-methyl-2-oxo-2,3-dihydro-1H-benzo[e][1,4]diazepin-3-yl) carbamoyl)-2-phenylhexanoic acid as a light-yellow off-white solid. MS(ES):m/z=556.1 [M+H⁺].

Example 5

A solution of (2R,3R)-6,6,6-trifluoro-3-((5-(3-fluorophenyl)-9-methyl-2-oxo-2,3-dihydro-1H-benzo[e][1,4]diazepin-3-yl)carbamoyl)-2-phenylhexanoic acid (153 mg, 0.275 mmol) in tetrahydrofuran (2 mL) was treated with EDC (106 mg, 0.551 mmol) and HOBT (84 mg, 0.551 mmol) and stirred at room temperature. Then added ammonia, 2M in i-propanol (1.377 mL, 2.75 mmol) and the resulting suspension was stirred at room temperature overnight. Diluted with water and extracted into ethyl acetate, washed with water and concentrated. The crude product was chromatographed on an ISCO Companion using a 40 g silica gel column and eluted with EtOAc/hexane gradient (20-100%) to give 55 mg white solid. Separation of the diastereomers by preparative SFC chromatography (Instrument: Berger SFC MGII, Column: Chiral IC 25×3 cm, 5 μm; Mobile Phase: 85/15 CO₂/MeOH Flow rate: 85 mL/min; Detection at 220 nm.) gave Example 5 (14 mg, 9% yield) as a white solid. HPLC: RT=8.844 min (H₂O/CH₃CN with TFA, SunFire C18 3.5 μm, 3.0×150 mm, gradient=15 min, wavelength=220 and 254 nm); MS(ES):m/z=555.1 [M+H⁺]; ¹H NMR (400 MHz, chloroform-d) δ 7.99 (s, 1H), 7.50-7.43 (m, 2H), 7.42-7.34 (m, 5H), 7.32-7.26 (m, 1H), 7.17-7.01 (m, 5H), 5.59-5.45 (m, 2H), 5.27 (d, J=8.1 Hz, 1H), 3.66 (d, J=9.7 Hz, 1H), 3.35 (td, J=9.8, 4.2 Hz, 1H), 2.39 (s, 3H), 2.29-2.17 (m, 2H), 2.07-1.90 (m, 2H).

Example 6

(2R,3R)—N1-((S)-1-Methyl-2-oxo-5-phenyl-2,3-dihydro-1H-benzo[e][1,4]diazepin-3-yl)-3-(3-methylisoxazol-4-yl)-2-(3,3,3-trifluoropropyl)succinamide

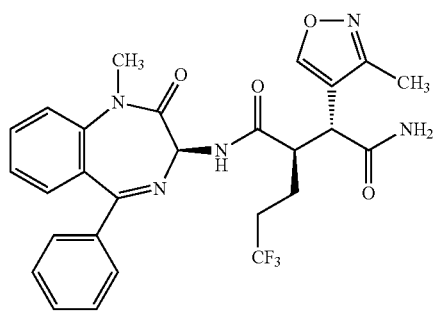

(6)

Example 6 was prepared from Intermediate 1F (100 mg, 0.2 mmol) and Intermediate S-2 (53 mg, 0.2 mmol) according to the general procedure shown for Example 5. After preparative chromatography (Column-CHIRALPAK® IC (250×4.6) mm 5 micron, Mobile Phase A: 0.2% Diethylamine-Hexane (60%), Mobile Phase B: Ethanol (40%), @ 220 and 250 nm Flow-1 ml/Min, Run-25 min) Example 6 (100 mg, 66%) was obtained. HPLC: RT=9.32 min (H$_2$O/CH$_3$CN with TFA, SunFire C18 3.5 μm, 4.6×150 mm, gradient=15 min, wavelength=220 and 254 nm); MS(ES):m/z=542 [M+H$^+$]; $^1$H NMR (400 MHz, CDCl$_3$) δ 8.72 (s, 1H), 7.57-7.61 (t, 1H)), 7.51-7.56 (t, 3H), 7.48-7.50 (d, 1H), 7.34-7.50 (m, 4H), 7.21-7.25 (d, 1H), 5.73 (bs, 1H), 5.53 (bs, 1H), 5.33-5.35 (d, 1H), 3.55-3.57 (d, 1H), 3.44 (s, 3H), 3.13-3.17 (m, 1H), 2.32 (s, 3H), 2.13-2.31 (m, 2H), 1.70-2.05 (m, 1H), 1.10-1.60 (m, 1H).

Example 7

(2R,3R)—N1-((S)-1-(Cyclopropylmethyl)-2-oxo-5-phenyl-2,3-dihydro-1H-benzo[e][1,4]diazepin-3-yl)-3-phenyl-2-(3,3,3-trifluoropropyl)succinamide

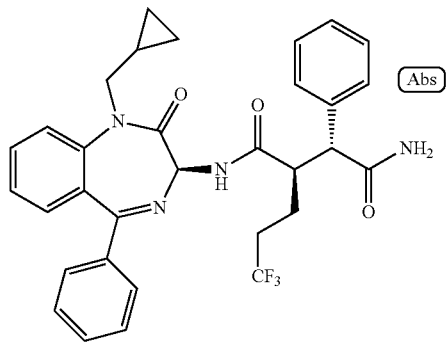

(7)

In a 5 mL screw top vial was added Example 4 (2R,3R)—N1-((S,Z)-2-oxo-5-phenyl-2,3-dihydro-1H-benzo[e][1,4]diazepin-3-yl)-3-phenyl-2-(3,3,3-trifluoropropyl)succinamide (20 mg, 0.038 mmol) and potassium fluoride 40% on aluminum oxide (60 mg, 0.413 mmol) in DMF (1 mL) to give a suspension. (Bromomethyl)cyclopropane (4.08 μL, 0.042 mmol) was added and the mixture was stirred at room temperature under nitrogen for 72 hours. The reaction mixture is dissolved in 1 ml of 1:1 DMF/AcOH and purified by preparative HPLC (Luna ODS 5 μm 21.2×100 mm which was eluted with a 10 min gradient from 100% ACN/water 0.1% TFA to 100%) to give Example 7 (14 mg, 61%). HPLC: RT=10.33 min (H$_2$O/CH$_3$CN with TFA, SunFire C18 3.5 μm, 4.6×150 mm, gradient=15 min, wavelength=220 and 254 nm); MS(ES):m/z=577 [M+H$^+$]; $^1$H NMR (400 MHz, chloroform-d) δ 7.58-7.51 (m, 1H), 7.50-7.33 (m, 13H), 7.26-7.16 (m, 1H), 5.49 (br. s., 1H), 5.34 (br. s., 1H), 5.29 (d, J=7.9 Hz, 1H), 4.24 (dd, J=14.3, 7.3 Hz, 1H), 3.67 (d, J=9.5 Hz, 1H), 3.51 (dd, J=14.2, 6.9 Hz, 1H), 3.27 (td, J=9.4, 4.3 Hz, 1H), 2.35-2.11 (m, 2H), 2.04-1.83 (m, 2H), 0.86 (t, J=7.7 Hz, 1H), 0.36-0.29 (m, 1H), 0.28-0.19 (m, 1H), 0.10-0.02 (m, 2H).

Example 8

(2R,3R)—N1-((S)-1-(Cyclopropylmethyl)-2-oxo-5-phenyl-2,3-dihydro-1H-benzo[e][1,4]diazepin-3-yl)-3-(4-fluorophenyl)-2-(3,3,3-trifluoropropyl)succinamide

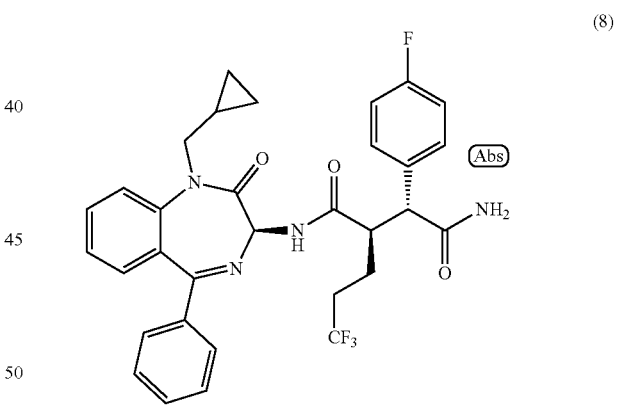

(8)

Example 8 was prepared from (2R,3R)-3-(4-fluorophenyl)-N1-((S,Z)-2-oxo-5-phenyl-2,3-dihydro-1H-benzo[e][1,4]diazepin-3-yl)-2-(3,3,3-trifluoropropyl)succinamide (10 mg, 0.019 mmol) and (bromomethyl)cyclopropane (10 mg, 0.074 mmol) using the procedure shown for Example 7 to give Example 8 (7.2 mg, 65%). HPLC: RT=10.529 min (H$_2$O/CH$_3$CN with TFA, SunFire C18 3.5 μm, 4.6×150 mm, gradient=15 min, wavelength=220 and 254 nm); MS(ES):m/z=595 [M+H$^+$]; $^1$H NMR (400 MHz, chloroform-d) δ 7.60-7.50 (m, 1H), 7.50-7.34 (m, 10H), 7.32-7.28 (m, 1H), 7.24-7.18 (m, 1H), 7.14-7.04 (m, 2H), 5.56 (d, J=12.5 Hz, 2H), 5.28 (d, J=8.1 Hz, 1H), 4.23 (dd, J=14.2, 7.4 Hz, 1H), 3.65 (d, J=9.9 Hz, 1H), 3.49 (dd, J=14.2, 6.9 Hz, 1H), 3.26-3.14 (m, 1H), 2.29-2.15 (m, 2H), 2.00-1.89 (m, 1H), 0.89-0.77 (m, 1H), 0.36-0.27 (m, 1H), 0.26-0.19 (m, 1H), 0.04 (d, J=4.0 Hz, 2H).

Example 9

(2R,3R)-3-(3-Methylisoxazol-4-yl)-N1-(S)-2-oxo-5-phenyl-2,3-dihydro-1H-benzo[e][1,4]diazepin-3-yl)-2-(3,3,3-trifluoropropyl)succinamide

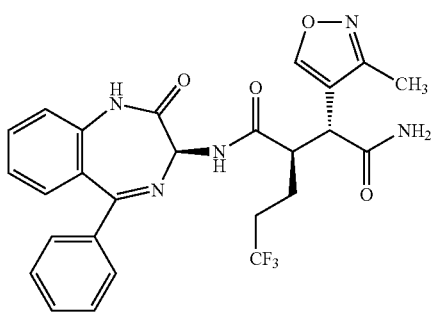

(9)

Example 9 was prepared from Intermediate 4A (75 mg, 0.3 mmol) and Intermediate S-2 (120 mg, 0.3 mmol) according to the general procedure shown for Example 5. After separation of the diastereomers by preparative chromatography (Column-SYMMETRY® C18 (250×4.6) 5 μm) Mobile Phase A: 0.5% TFA in water Mobile Phase B: ACN wavelength=220 nm and 254 nm); gradient=35 min.) Example 9 (130 mg, 6%) was obtained. HPLC: RT=8.52 min (H$_2$O/CH$_3$CN with TFA, SunFire C18 3.5 μm, 4.6×150 mm, gradient=15 min, wavelength=220 and 254 nm); MS(ES):m/z=528 [M+H$^+$]; $^1$H NMR (400 MHz, CDCl$_3$) δ 10.9 (s, 1H), 9.39-9.41 (d, 1H), 8.68 (s, 1H), 7.83 (s, 1H), 7.61-7.65 (m, 1H), 7.41-7.54 (m, 5H), 7.18-7.30 (m, 4H), 5.02-5.04 (d, 1H), 3.54-3.57 (d, 1H), 3.19-3.25 (m, 1H), 2.64-2.67 (m, 1H), 2.30-2.33 (m, 1H), 2.17 (s, 3H), 1.69-1.77 (m, 2H).

Example 10

(2R,3R)—N1-((S)-2-Oxo-5-phenyl-2,3-dihydro-1H-benzo[e][1,4]diazepin-3-yl)-3-(pyridin-3-yl)-2-(3,3,3-trifluoropropyl)succinamide

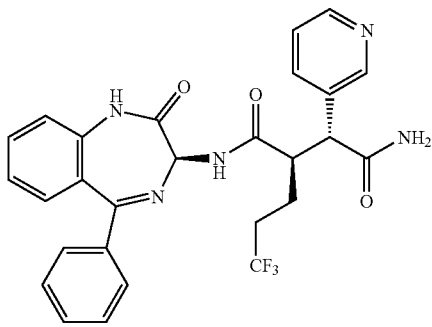

(10)

Example 10 was prepared from Intermediate 4A (47.7 mg, 0.190 mmol) and Intermediate S-3 (60.0 mg, 0.173 mmol) according to the general procedure shown for Example 5. Example 10 (12.5 mg, 16%) was obtained. HPLC: RT=5.708 min (H$_2$O/CH$_3$CN with TFA, SunFire C18 3.5 μm, 4.6×150 mm, gradient=15 min, wavelength=220 and 254 nm); MS(ES):m/z=524.2 [M+H$^+$]; $^1$H NMR (400 MHz, methanol-d$_4$) δ 8.56 (d, J=1.8 Hz, 1H), 8.51-8.42 (m, 1H), 8.06-7.95 (m, 1H), 7.66-7.54 (m, 1H), 7.52-7.46 (m, 1H), 7.46-7.32 (m, 5H), 7.30-7.15 (m, 3H), 4.99 (s, 1H), 3.78 (d, J=11.2 Hz, 1H), 3.47-3.41 (m, 1H), 2.67-2.46 (m, 1H), 2.44-2.27 (m, 1H), 2.01-1.84 (m, 2H).

Example 11

(2R,3R)-3-(3-Methyl-4-isoxazolyl)-N-((3S)-2-oxo-5-phenyl-1-(2-pyridinyl)-2,3-dihydro-1H-1,4-benzodiazepin-3-yl)-2-(3,3,3-trifluoropropyl)succinamide

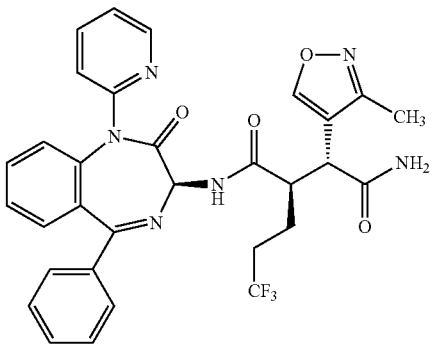

(11)

Example 11 was prepared from Intermediate B-15 (134 mg, 0.40 mmol) and Intermediate S-2 (130.0 mg, 0.37 mmol) according to the general procedure shown for Example 5. After separation of the diastereomers by preparative chiral chromatography (CHIRALPAK® IC 250×4.6 mm ID, 5 μm, 65/35 H$_2$O/CH$_3$CN with TFA), Example 11 (130 mg, 53%) was obtained. HPLC: RT=8.66 min (H$_2$O/CH$_3$CN with TFA, SunFire C18 3.5 μm, 4.6×150 mm, gradient=15 min, wavelength=220 and 254 nm); MS(ES):m/z=605 [M+H$^+$]; $^1$H NMR (400 MHz, DMSO-d$_6$) δ 9.51 (d, J=7.5 Hz, 1H), 8.71 (s, 1H), 8.50-8.44 (m, 1H), 7.99 (td, J=7.8, 2.0 Hz, 1H), 7.84 (br. s., 1H), 7.62-7.48 (m, 7H), 7.43-7.38 (m, 1H), 7.37-7.30 (m, 2H), 7.17 (br. s., 1H), 6.97 (d, J=8.1 Hz, 1H), 5.37 (d, J=7.7 Hz, 1H), 3.57 (d, J=11.2 Hz, 1H), 2.62-2.56 (m, 1H), 2.38-2.24 (m, 1H), 2.18 (s, 3H), 2.10 (d, J=2.9 Hz, 1H), 1.82-1.68 (m, 2H).

Example 12

(2R,3R)—N-((3S)-2-Oxo-5-phenyl-1-(2-pyridinyl)-2,3-dihydro-1H-1,4-benzodiazepin-3-yl)-3-phenyl-2-(3,3,3-trifluoropropyl)succinamide

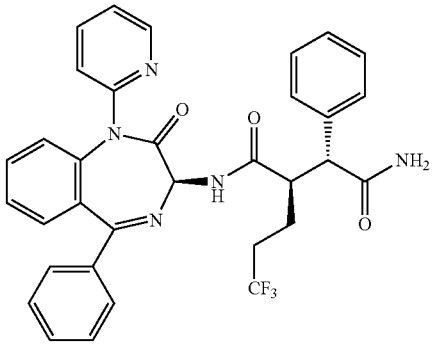

(12)

Example 12 was prepared from Intermediate B-15 (37.9 mg, 0.115 mmol) and Intermediate S-1 (40.0 mg, 0.115 mmol) according to the general procedure shown for Example 5. After separation of the diastereomers (Preparative SFC chromatography, Berger SFC MGII, CHIRALPAK® IB 250×21 mm ID, 5 µm, 80/20 CO$_2$/MeOH, 50 mL/min), Example 12 (39.2 mg, 58.1%) was obtained. HPLC: RT=9.28 min (H$_2$O/CH$_3$CN with TFA, SunFire C18 3.5 µm, 4.6×150 mm, gradient=15 min, wavelength=220 and 254 nm); MS(ES):m/z=600 [M+H$^+$]; $^1$H NMR (400 MHz, DMSO-d$_6$) δ 9.37 (d, J=7.5 Hz, 1H), 8.46 (dd, J=4.8, 1.1 Hz, 1H), 7.98 (td, J=7.8, 1.9 Hz, 1H), 7.75-7.65 (m, 3H), 7.58-7.47 (m, 6H), 7.44-7.36 (m, 3H), 7.32-7.20 (m, 4H), 6.95 (d, J=8.4 Hz, 2H), 5.21 (d, J=7.3 Hz, 1H), 3.71 (d, J=11.2 Hz, 1H), 3.49 (td, J=10.7, 3.7 Hz, 1H), 2.63-2.54 (m, 1H), 2.40-2.23 (m, 1H), 1.85-1.60 (m, 2H).

Example 13

(2R,3R)-3-(3-Methyl-4-isoxazolyl)-N-((7S)-6-oxo-9-phenyl-6,7-dihydro-5H-[1,3]dioxolo[4,5-h][1,4]benzodiazepin-7-yl)-2-(3,3,3-trifluoropropyl)succinamide (13)

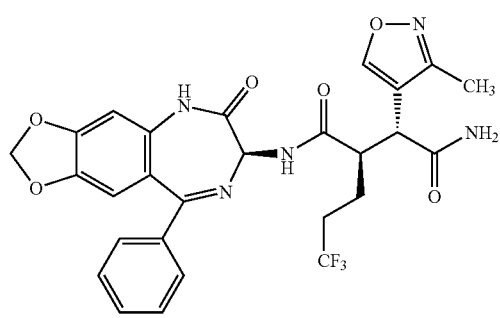

Example 13 was prepared from Intermediate B-14 (20.0 mg, 0.068 mmol) and Intermediate S-2 (23.8 mg, 0.068 mmol) according to the general procedure shown for Example 5. Example 13 (9.12 mg, 24.1%) was obtained. HPLC: RT=7.64 min (H$_2$O/CH$_3$CN with TFA, SunFire C18 3.5 µm, 4.6×150 mm, gradient=15 min, wavelength=220 and 254 nm); MS(ES):m/z=572 [M+H$^+$]; $^1$H NMR (400 MHz, DMSO-d$_6$) δ 10.61 (s, 1H), 9.33 (d, J=7.5 Hz, 1H), 8.67 (s, 1H), 7.82 (br. s., 1H), 7.54-7.48 (m, 1H), 7.46-7.40 (m, 7H), 7.16 (br. s., 1H), 6.78 (s, 1H), 6.67 (s, 1H), 6.15 (s, 1H), 6.11 (s, 1H), 5.03 (d, J=7.5 Hz, 1H), 3.56 (d, J=11.2 Hz, 1H), 3.26-3.16 (m, 1H), 2.70-2.62 (m, 1H), 2.36-2.25 (m, 1H), 2.18 (s, 3H), 1.75 (d, J=12.8 Hz, 2H).

Example 14

(2R,3R)—N-((3S)-1-(5-Methoxy-2-pyridinyl)-2-oxo-5-phenyl-2,3-dihydro-1H-1,4-benzodiazepin-3-yl)-3-(3-methyl-4-isoxazolyl)-2-(3,3,3-trifluoropropyl)succinamide (14)

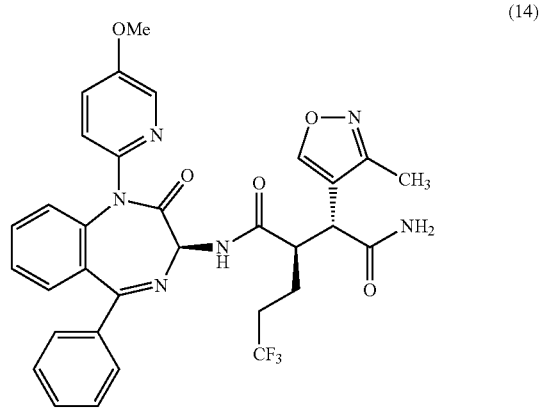 [SMILES: COc1ccc(N2C(=O)[C@@H](NC(=O)[C@H](CCC(F)(F)F)[C@@H](C(N)=O)c3conc3C)N=C(c3ccccc3)c3ccccc32)nc1]

Example 14 was prepared from Intermediate B-17 (55.0 mg, 0.153 mmol) and Intermediate S-2 (59.3 mg, 0.169 mmol) according to the general procedure shown for Example 5. Example 14 (26.0 mg, 51.4%) was obtained. HPLC: RT=9.09 min (H$_2$O/CH$_3$CN with TFA, SunFire C18 3.5 µm, 4.6×150 mm, gradient=15 min, wavelength=220 and 254 nm); MS(ES):m/z=635 [M+H$^+$]; $^1$H NMR (400 MHz, DMSO-d$_6$) δ ppm 9.48 (1H, d, J=7.48 Hz), 8.71 (1H, s), 8.17 (1H, d, J=2.86 Hz), 7.84 (1H, br. s.), 7.43-7.65 (9H, m), 7.28-7.38 (2H, m), 7.17 (1H, br. s.), 6.97 (1H, d, J=7.92 Hz), 5.34 (1H, d, J=7.48 Hz), 3.86 (3H, s), 3.56 (1H, d, J=11.22 Hz), 2.56 (1H, br. s.), 2.26-2.40 (1H, m), 2.18 (3H, s), 1.68-1.82 (2H, m).

Example 15

(2R,3R)—N-((3S)-1-(5-Methoxy-2-pyridinyl)-2-oxo-5-phenyl-2,3-dihydro-1H-1,4-benzodiazepin-3-yl)-3-phenyl-2-(3,3,3-trifluoropropyl)succinamide (15)

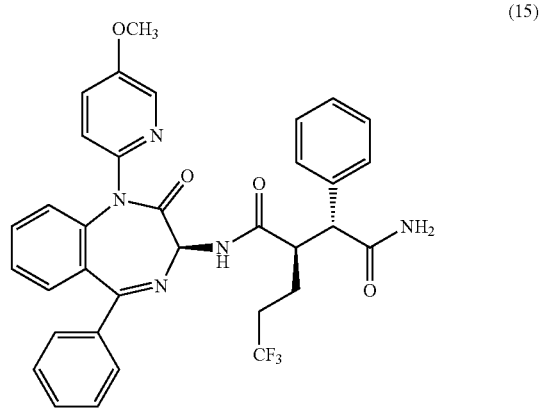 [SMILES: COc1ccc(N2C(=O)[C@@H](NC(=O)[C@H](CCC(F)(F)F)[C@@H](C(N)=O)c3ccccc3)N=C(c3ccccc3)c3ccccc32)nc1]

Example 15 was prepared from Intermediate B-17 (30.0 mg, 0.084 mmol) and Intermediate S-1 (30.5 mg, 0.088 mmol) according to the general procedure shown for Example 5. After separation of the diastereomers (Preparative SFC chromatography, Berger SFC MGII, Chiral IC 250×30 mm ID, 5 μm, 80/20 CO$_2$/MeOH, 85 mL/min), Example 15 (18.5 mg, 34.0%) was obtained. HPLC: RT=9.65 min (H$_2$O/CH$_3$CN with TFA, SunFire C18 3.5 μm, 4.6×150 mm, gradient=15 min, wavelength=220 and 254 nm); MS(ES):m/z=630 [M+H$^+$]; $^1$H NMR (400 MHz, chloroform-d) δ 8.13 (s, 1H), 7.57-7.34 (m, 13H), 7.31 (d, J=5.1 Hz, 4H), 7.23-7.15 (m, 1H), 6.94 (d, J=8.1 Hz, 1H), 5.41 (s, 1H), 3.87 (s, 3H), 3.69 (d, J=10.6 Hz, 1H), 3.36-3.25 (m, 1H), 2.41-2.22 (m, 2H), 2.03-1.86 (m, 2H).

Example 16

(2R,3R)—N-((3S)-1-(6-Methoxy-2-pyridinyl)-2-oxo-5-phenyl-2,3-dihydro-1H-1,4-benzodiazepin-3-yl)-3-phenyl-2-(3,3,3-trifluoropropyl)succinamide

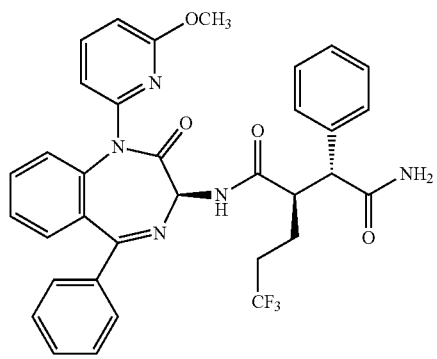

(16)

Example 16 was prepared from Intermediate B-18 (48.0 mg, 0.134 mmol) and Intermediate S-1 (44.1 mg, 0.127 mmol) according to the general procedure shown for Example 5. After separation of the diastereomers (Preparative SFC chromatography, Berger SFC MGII, Chiral IC 250×30 mm ID, 5 μm, 83/17 CO$_2$/MeOH, 85 mL/min), Example 16 (11.5 mg, 17.5%) was obtained. HPLC: RT=10.46 min (H$_2$O/CH$_3$CN with TFA, SunFire C18 3.5 μm, 4.6×150 mm, gradient=15 min, wavelength=220 and 254 nm); MS(ES):m/z=630 [M+H$^+$]; $^1$H NMR (400 MHz, MeOD) δ 7.77 (t, J=7.8 Hz, 1H), 7.58-7.49 (m, 4H), 7.47-7.38 (m, 4H), 7.33-7.24 (m, 5H), 7.16 (d, J=7.5 Hz, 1H), 7.08 (d, J=8.1 Hz, 1H), 6.73 (d, J=8.1 Hz, 1H), 5.21 (s, 1H), 3.73 (d, J=11.2 Hz, 1H), 3.63 (s, 3H), 3.49-3.39 (m, 1H), 2.64-2.50 (m, 1H), 2.43-2.29 (m, 1H), 2.00-1.84 (m, 2H).

Example 17

(2R,3R)—N1-((S)-9-Chloro-2-oxo-5-phenyl-2,3-dihydro-1H-benzo[e][1,4]diazepin-3-yl)-3-(3-methylisoxazol-4-yl)-2-(3,3,3-trifluoropropyl)succinamide

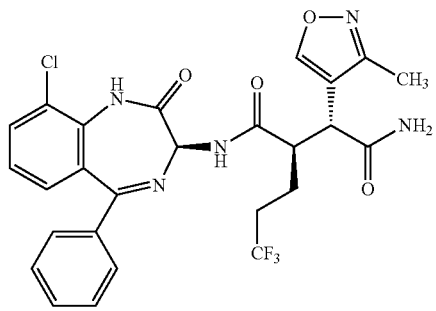

(17)

Example 17 was prepared from Intermediate B-12 (200 mg, 0.7 mmol) and Intermediate S-2 (246 mg, 0.7 mmol) according to the general procedure shown for Example 5. Example 17 (17 mg, 13.9%) was obtained. LC/MS, m/z 562.2 (M+1). HPLC RT=0.86 min. LC/MS (BEH C18 2.1×50 mm, 1.7 μm, 0 to 100% B in 1 min with 0.5 min hold time, Flow rate=1 ml/min, detection at 254 nm, Solvent A: 100% water/0.1% TFA; Solvent B: 100% ACN/0.1% TFA). $^1$H NMR (400 MHz, MeOD) δ ppm 8.64-8.72 (1H, m), 7.69-7.82 (1H, m), 7.49-7.58 (3H, m), 7.40-7.49 (2H, m), 7.17-7.35 (2H, m), 5.12-5.22 (1H, m), 3.59-3.68 (1H, m), 3.17-3.32 (1H, m), 2.49-2.70 (1H, m), 2.31-2.42 (1H, m), 2.28 (3H, s), 1.79-1.99 (2H, m).

Example 18

(2R,3R)—N1-((S)-9-Fluoro-2-oxo-5-phenyl-2,3-dihydro-1H-benzo[e][1,4]diazepin-3-yl)-3-(3-methylisoxazol-4-yl)-2-(3,3,3-trifluoropropyl)succinamide

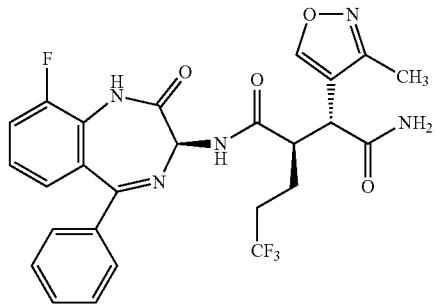

(18)

Example 18 was prepared from Intermediate B-11 (30 mg, 0.111 mmol) and Intermediate S-2 (39.1 mg, 0.111 mmol) according to the general procedure shown for Example 5. After separation of the diastereomers by preparative HPLC (YMC ODS C18 5 μm 20×100 mm, eluting with 0%-100% aqueous methanol over 20 minutes containing 0.1% TFA, 20 mL/min, monitor 254 nm), Example 18 (8.9 mg, 14%) was obtained. HPLC: RT=7.206 min (H$_2$O/CH$_3$CN with TFA, SunFire C18 3.5 μm, 4.6×150 mm, gradient=15 min, wavelength=220 and 254 nm); MS(ES):m/z=546 [M+H$^+$]; $^1$H NMR (400 MHz, methanol-d$_4$) δ 8.68 (s, 1H), 7.59-7.38 (m, 6H), 7.31-7.20 (m, 1H), 7.15 (s, 1H), 5.24 (s, 1H), 3.66 (s, 1H), 3.29-3.18 (m, 1H), 2.69-2.49 (m, 1H), 2.44-2.21 (m, 4H), 2.01-1.81 (m, 2H).

Example 19

(2R,3R)—N1-((S)-9-Fluoro-2-oxo-5-phenyl-2,3-dihydro-1H-benzo[e][1,4]diazepin-3-yl)-3-phenyl-2-(3,3,3-trifluoropropyl)succinamide (19)

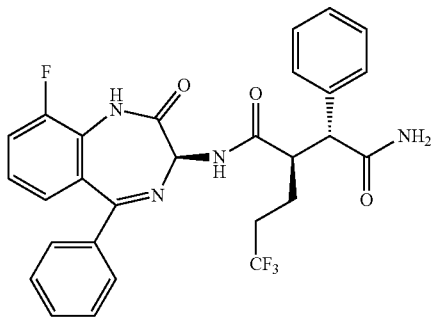

Example 19 was prepared from Intermediate B-11 (30 mg, 0.111 mmol) and Intermediate S-1 (38.6 mg, 0.111 mmol) according to the general procedure shown for Example 5. After separation of the diastereomers by preparative SFC chromatography (Instrument: Berger SFC MGII, Column: Chiral IC 25×3 cm, 5 μm; Mobile Phase: 82/18 CO$_2$/MeOH Flow rate: 85 mL/min; Detection at 220 nm.), Example 19 (8.5 mg, 14%) was obtained. HPLC: RT=7.793 min (H$_2$O/CH$_3$CN with TFA, SunFire C18 3.5 μm, 4.6×150 mm, gradient=15 min, wavelength=220 and 254 nm); MS(ES):m/z=541 [M+H$^+$]; $^1$H NMR (400 MHz, methanol-d$_4$) δ 7.54-7.40 (m, 8H), 7.34-7.18 (m, 4H), 7.08 (d, J=7.9 Hz, 1H), 5.03 (s, 1H), 3.73 (d, J=11.4 Hz, 1H), 3.43 (td, J=10.5, 4.4 Hz, 1H), 3.37 (s, 1H), 2.68-2.47 (m, 1H), 2.46-2.22 (m, 1H), 2.03-1.79 (m, 2H).

Example 20

(2R,3R)—N1-((S)-9-Methoxy-2-oxo-5-phenyl-2,3-dihydro-1H-benzo[e][1,4]diazepin-3-yl)-3-(3-methylisoxazol-4-yl)-2-(3,3,3-trifluoropropyl)succinamide (20)

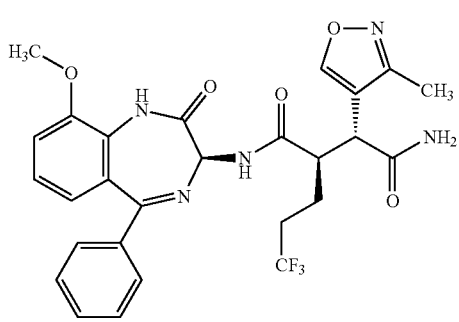

Example 20 was prepared from Intermediate B-10 (50 mg, 0.178 mmol) and Intermediate S-2 (68.7 mg, 0.196 mmol) according to the general procedure shown for Example 5. Example 20 (29 mg, 29%) was obtained. HPLC: RT=8.128 min (H$_2$O/CH$_3$CN with TFA, SunFire C18 3.5 μm, 4.6×150 mm, gradient=15 min, wavelength=220 and 254 nm); MS(ES):m/z=558.5 [M+H$^+$]; $^1$H NMR (400 MHz, methanol-d$_4$) δ 8.67 (s, 1H), 7.53-7.45 (m, 3H), 7.44-7.36 (m, 2H), 7.29-7.23 (m, 1H), 7.22-7.15 (m, 1H), 6.86 (dd, J=7.7, 1.3 Hz, 1H), 5.17 (s, 1H), 3.99 (s, 3H), 3.62 (d, J=11.2 Hz, 1H), 3.22 (dt, J=10.9, 7.2 Hz, 1H), 2.64-2.48 (m, 1H), 2.41-2.27 (m, 1H), 2.26 (s, 3H), 1.97-1.83 (m, 2H).

Example 21

(2R,3R)—N1-((S)-9-Methoxy-2-oxo-5-phenyl-2,3-dihydro-1H-benzo[e][1,4]diazepin-3-yl)-3-phenyl-2-(3,3,3-trifluoropropyl)succinamide (21)

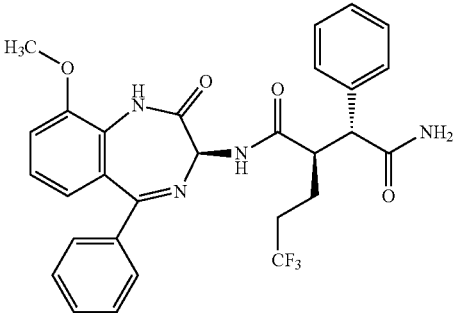

Example 21 was prepared from Intermediate B-10 (270 mg, 0.96 mmol) and Intermediate S-1 (332 mg, 0.96 mmol) according to the general procedure shown for Example 5. Example 21 (340 mg, 62%) was obtained. HPLC: RT=10.251 min (H$_2$O/CH$_3$CN with TFA, SunFire C18 3.5 μm, 4.6×150 mm, gradient=15 min, wavelength=220 and 254 nm); MS(ES):m/z=553.3 [M+H$^+$]; $^1$H NMR (400 MHz, DMSO-d$_6$) δ 9.99 (s, 1H), 9.24 (d, J=7.5 Hz, 1H), 7.69 (br. s., 1H), 7.56-7.31 (m, 7H), 7.30-7.12 (m, 5H), 6.91 (br. s., 1H), 6.75 (d, J=7.9 Hz, 1H), 4.86 (dd, J=7.5, 1.8 Hz, 1H), 3.89 (s, 3H), 3.70 (d, J=11.4 Hz, 1H), 3.43 (t, J=10.3 Hz, 1H), 2.80-2.63 (m, 1H), 2.43-2.25 (m, 1H), 1.88-1.60 (m, 2H).

Example 22

(2R,3R)—N-((3S)-1-(5-Chloro-2-pyridinyl)-2-oxo-5-phenyl-2,3-dihydro-1H-1,4-benzodiazepin-3-yl)-3-phenyl-2-(3,3,3-trifluoropropyl)succinamide (22)

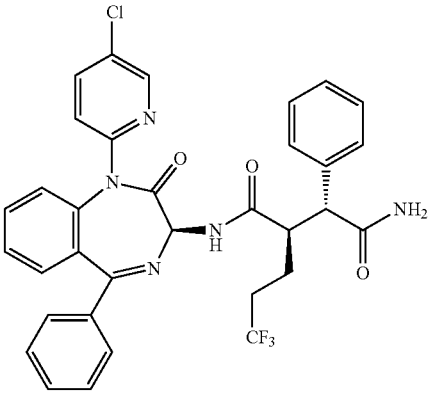

Example 22 was prepared from Intermediate B-16 (50.0 mg, 0.138 mmol) and Intermediate S-1 (57.3 mg, 0.165 mmol) according to the general procedure shown for Example 5. Example 22 (44.0 mg, 47.8%) was obtained. HPLC: RT=10.43 min (H$_2$O/CH$_3$CN with TFA, SunFire C18 3.5 μm, 4.6×150 mm, gradient=15 min, wavelength=220 and 254 nm); MS(ES):m/z=634 [M+H$^+$]; $^1$H NMR (500 MHz, DMSO-d$_6$) δ 9.36 (d, J=7.5 Hz, 1H), 8.51 (dd, J=2.8, 0.6 Hz, 1H), 8.12 (dd, J=8.6, 2.8 Hz, 1H), 7.69 (br. s., 1H), 7.66-7.63 (m, 1H), 7.59-7.52 (m, 2H), 7.51-7.45 (m, 4H), 7.42-7.38 (m, 2H), 7.35-7.19 (m, 5H), 6.99 (d, J=7.8 Hz, 1H), 6.91 (s, 1H), 5.22 (d, J=7.5 Hz, 1H), 3.71 (d, J=11.4 Hz, 1H), 3.49 (td, J=10.6, 3.7 Hz, 1H), 2.60-2.54 (m, 1H), 2.40-2.29 (m, 1H), 1.84-1.64 (m, 2H).

Example 23

(2R,3R)—N-((3S)-1-(5-Chloro-2-pyridinyl)-2-oxo-5-phenyl-2,3-dihydro-1H-1,4-benzodiazepin-3-yl)-3-(3-methyl-4-isoxazolyl)-2-(3,3,3-trifluoropropyl)succinamide (23)

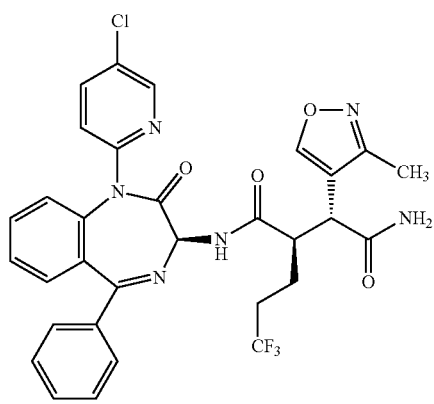

Example 23 was prepared from Intermediate B-16 (50.0 mg, 0.138 mmol) and Intermediate S-2 (58.1 mg, 0.165 mmol) according to the general procedure shown for Example 5. Example 23 (38.0 mg, 42.3%) was obtained. HPLC: RT=9.85 min (H$_2$O/CH$_3$CN with TFA, SunFire C18 3.5 μm, 4.6×150 mm, gradient=15 min, wavelength=220 and 254 nm); MS(ES):m/z=639 [M+H$^+$]; $^1$H NMR (400 MHz, DMSO-d$_6$) δ 9.52 (d, J=7.5 Hz, 1H), 8.71 (s, 1H), 8.54-8.50 (m, 1H), 8.14 (dd, J=8.6, 2.6 Hz, 1H), 7.84 (s, 1H), 7.68 (dd, J=8.6, 0.4 Hz, 1H), 7.61-7.48 (m, 6H), 7.39-7.33 (m, 2H), 7.18 (s, 1H), 7.01 (d, J=8.1 Hz, 1H), 5.38 (d, J=7.5 Hz, 1H), 3.56 (d, J=11.2 Hz, 1H), 3.28-3.23 (m, 1H), 2.38-2.27 (m, 2H), 2.18 (s, 3H), 1.81-1.69 (m, 2H).

Example 24

(2R,3R)—N1-((S)-9-Chloro-2-oxo-5-phenyl-2,3-dihydro-1H-benzo[e][1,4]diazepin-3-yl)-3-phenyl-2-(3,3,3-trifluoropropyl)succinamide (24)

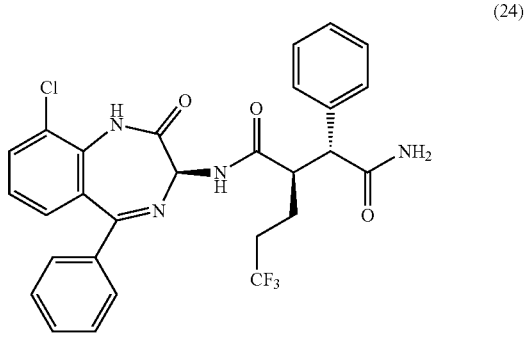 [SMILES: NC(=O)[C@@H](c1ccccc1)[C@@H](CCC(F)(F)F)C(=O)N[C@H]1N=C(c2ccccc2)c2cccc(Cl)c2NC1=O]

Example 24 was prepared from Intermediate B-12 (44 mg, 0.12 mmol) and Intermediate S-1 (41.6 mg, 0.12 mmol) according to the general procedure shown for Example 5. Example 24 (8.7 mg, 12.52%) was obtained. HPLC: RT=9.023 min (H$_2$O/CH$_3$CN with TFA, SunFire C18 3.5 μm, 4.6×150 mm, gradient=15 min, wavelength=220 and 254 nm); MS(ES):m/z=557.1 [M+H$^+$]; $^1$H NMR (500 MHz, DMSO-d$_6$) δ 10.40 (s, 1H), 9.27 (d, J=7.5 Hz, 1H), 7.80 (dd, J=7.8, 1.4 Hz, 1H), 7.69 (br. s., 1H), 7.56-7.50 (m, 1H), 7.46 (t, J=7.5 Hz, 2H), 7.38 (d, J=8.9 Hz, 4H), 7.29-7.23 (m, 3H), 7.22-7.16 (m, 2H), 6.91 (br. s., 1H), 4.89 (d, J=7.2 Hz, 1H), 3.70 (d, J=11.7 Hz, 1H), 3.50-3.41 (m, 1H), 2.70 (d, J=12.2 Hz, 1H), 1.85-1.75 (m, 1H), 1.74-1.63 (m, 1H).

Example 25

(2R,3R)—N1-((S)-7-Cyano-9-methoxy-2-oxo-5-phenyl-2,3-dihydro-1H-benzo[e][1,4]diazepin-3-yl)-3-phenyl-2-(3,3,3-trifluoropropyl)succinamide (25)

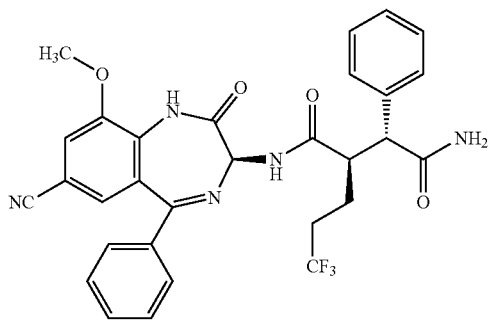

Example 25 was prepared from Intermediate B-19 (60 mg, 0.196 mmol) and Intermediate S-1 (79 mg, 0.229 mmol) according to the general procedure shown for Example 5. The material was purified by preparative SFC chromatography (Berger SFC MGII, Chiral IB 250×21 mm ID, 5 μm, 83/17

CO$_2$/MeOH, 50 mL/min). Example 25 (13 mg, 11%) was obtained. HPLC: RT=8.548 min (H$_2$O/CH$_3$CN with TFA, SunFire C18 3.5 μm, 4.6×150 mm, gradient=15 min, wavelength=220 and 254 nm); MS(ES):m/z=578.3 [M+H$^+$]; $^1$H NMR (400 MHz, methanol-d$_4$) δ 7.56-7.48 (m, 2H), 7.46-7.35 (m, 6H), 7.27-7.13 (m, 4H), 5.01 (s, 1H), 4.00 (s, 3H), 3.75 (d, J=11.2 Hz, 1H), 3.54-3.43 (m, 1H), 2.44 (qd, J=10.7, 7.0 Hz, 2H), 2.05-1.89 (m, 2H).

Example 26

(2R,3R)—N1-((S)-9-Cyclopropoxy-2-oxo-5-phenyl-2,3-dihydro-1H-benzo[e][1,4]diazepin-3-yl)-3-phenyl-2-(3,3,3-trifluoropropyl)succinamide (26)

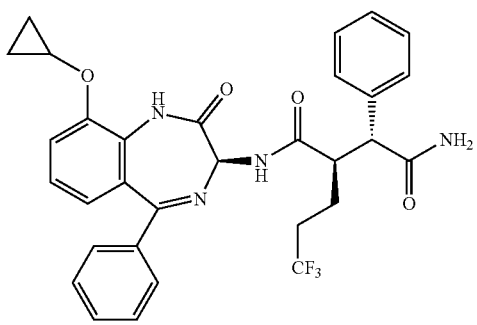

Example 26 was prepared from Intermediate B-8 (1.35 g, 2.88 mmol) and Intermediate S-1 (0.6 g, 1.73 mmol) according to the general procedure shown for Example 5. After separation of the diastereomers by preparative SFC chromatography (Berger SFC MGII, CHIRALPAK® IC 250×20 mm ID, 5 μm, 82/18 CO$_2$/MeOH, 85 mL/min), Example 26 (193 mg, 19%) was obtained. HPLC: RT=9.28 min (H$_2$O/CH$_3$CN with TFA, SunFire C18 3.5 μm, 4.6×150 mm, gradient=15 min, wavelength=220 and 254 nm); MS(ES):m/z=579 [M+H$^+$]; $^1$H NMR (400 MHz, methanol-d$_4$) δ 7.56 (dd, J=8.1, 1.1 Hz, 1H), 7.52-7.35 (m, 7H), 7.35-7.13 (m, 4H), 6.82 (dd, J=7.9, 1.1 Hz, 1H), 4.97 (s, 1H), 3.95 (d, J=2.6 Hz, 1H), 3.73 (d, J=11.2 Hz, 1H), 2.68-2.24 (m, 2H), 2.03-1.80 (m, 1H), 1.52-1.23 (m, 1H), 0.97 (s, 1H), 0.91-0.82 (m, 1H).

Example 27

(2R,3R)—N1-((S)-5-(4-Fluorophenyl)-9-methyl-2-oxo-2,3-dihydro-1H-benzo[e][1,4]diazepin-3-yl)-3-phenyl-2-(3,3,3-trifluoropropyl)succinamide (27)

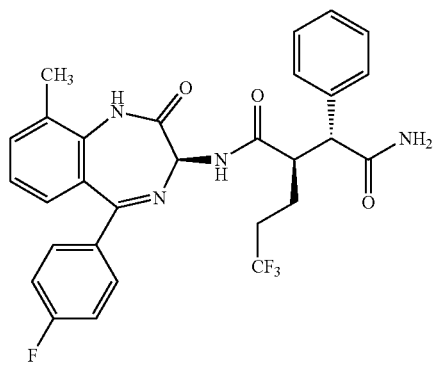

Example 27 was prepared from Intermediate B-3 (160 mg, 0.439 mmol) and Intermediate S-1 (152 mg, 0.439 mmol) according to the general procedure shown for Example 5. After separation of the diastereomers by preparative SFC chromatography (Instrument: Berger SFC MGII, Column: PHENOMENEX® Lux Cellulose 2 25×3 cm, 5 μm; Mobile Phase: 80/20 CO$_2$/MeOH Flow rate: 85 mL/min; Detection at 220 nm.), Example 27 (mg, %) was obtained. HPLC: RT=8.864 min (H$_2$O/CH$_3$CN with TFA, SunFire C18 3.5 μm, 4.6×150 mm, gradient=15 min, wavelength=220 and 254 nm); MS(ES):m/z=555.1 [M+H$^+$]; $^1$H NMR (400 MHz, methanol-d$_4$) δ 7.52-7.40 (m, 5H), 7.34-7.22 (m, 3H), 7.19-7.02 (m, 4H), 4.93 (s, 1H), 3.70 (d, J=11.2 Hz, 1H), 3.43-3.31 (m., 1H), 2.65-2.49 (m, 1H), 2.42 (s, 3H), 2.38-2.25 (m, 1H), 1.98-1.82 (m, 2H).

Example 28

(2R,3R)—N1-((S)-9-Methyl-2-oxo-5-(3-(trifluoromethyl)phenyl)-2,3-dihydro-1H-benzo[e][1,4]diazepin-3-yl)-3-(3-methylisoxazol-4-yl)-2-(3,3,3-trifluoropropyl)succinamide (28)

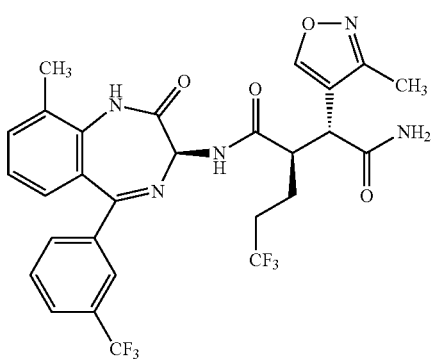

Example 28 was prepared from Intermediate B-4 (100 mg, 0.241 mmol) and Intermediate S-2 (85 mg, 0.241 mmol) according to the general procedure shown for Example 5. Example 28 (38 mg, 58%) was obtained. HPLC: RT=8.911 min (H$_2$O/CH$_3$CN with TFA, SunFire C18 3.5 μm, 4.6×150 mm, gradient=15 min, wavelength=220 and 254 nm); MS(ES):m/z=610.1 [M+H$^+$]; $^1$H NMR (400 MHz, methanol-d$_4$) δ 8.66 (s, 1H), 7.85 (s, 1H), 7.80 (d, J=7.9 Hz, 1H), 7.74 (s, 1H), 7.67-7.59 (m, 1H), 7.56-7.49 (m, 1H), 7.22-7.15 (m, 1H), 7.15-7.10 (m, 1H), 5.16 (s, 1H), 3.63 (d, J=11.2 Hz, 1H), 3.23 (dt, J=11.2, 7.0 Hz, 1H), 2.67-2.53 (m, 1H), 2.46 (s, 3H), 2.38-2.28 (m, 1H), 2.24 (s, 3H), 1.96-1.84 (m, 2H).

Example 29

(2R,3R)—N1-((S)-9-Methyl-2-oxo-5-(3-(trifluoromethyl)phenyl)-2,3-dihydro-1H-benzo[e][1,4]diazepin-3-yl)-3-phenyl-2-(3,3,3-trifluoropropyl)succinamide (29)

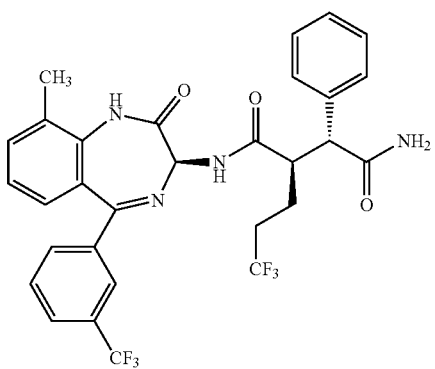

Example 29 was prepared from Intermediate B-4 (100 mg, 0.241 mmol) and Intermediate S-1 (84 mg, 0.241 mmol) according to the general procedure shown for Example 5. After separation of the diastereomers by preparative SFC chromatography (Instrument: Berger SFC MGII, Column: Regis Welk-O R,R 25×3 cm, 5 μm; Mobile Phase: 88/12 $CO_2$/MeOH Flow rate: 85 mL/min; Detection at 220 nm.), Example 29 (30 mg, 31%) was obtained. HPLC: RT=9.419 min ($H_2O$/$CH_3CN$ with TFA, SunFire C18 3.5 μm, 4.6×150 mm, gradient=15 min, wavelength=220 and 254 nm); MS(ES):m/z=605.1 [M+H$^+$]; $^1$H NMR (400 MHz, methanol-d$_4$) δ 7.84 (s, 1H), 7.81 (dd, J=5.0, 3.4 Hz, 1H), 7.62-7.59 (m, 2H), 7.52 (d, J=6.8 Hz, 1H), 7.48-7.43 (m, 2H), 7.32-7.24 (m, 3H), 7.21-7.14 (m, 1H), 7.09 (dd, J=7.9, 0.9 Hz, 1H), 4.97 (s, 1H), 3.72 (d, J=11.2 Hz, 1H), 3.46-3.40 (m, 1H), 2.64-2.50 (m, 1H), 2.46 (s, 3H), 2.40-2.28 (m, 1H), 1.98-1.87 (m, 2H).

Example 30

(2R,3R)—N1-((S)-9-Methyl-2-oxo-5-phenyl-2,3-dihydro-1H-benzo[e][1,4]diazepin-3-yl)-3-phenyl-2-(3,3,3-trifluoropropyl)succinamide (30)

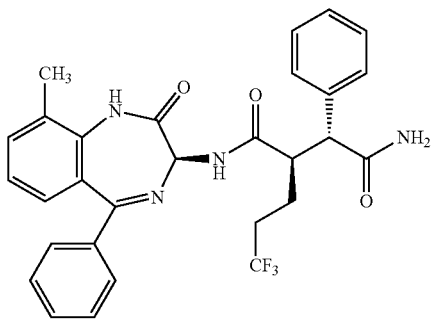

Example 30 was prepared from Intermediate B-9 (62 mg, 0.144 mmol) and Intermediate S-1 (50 mg, 0.144 mmol) according to the general procedure shown for Example 5. Example 30 (36 mg, 25%) was obtained. HPLC: RT=10.173 min ($H_2O$/$CH_3CN$ with TFA, SunFire C18 3.5 μm, 4.6×150 mm, gradient=15 min, wavelength=220 and 254 nm); MS(ES):m/z=537.3 [M+H$^+$]; $^1$H NMR (400 MHz, DMSO-d$_6$) δ 10.09 (s, 1H), 9.19 (d, J=7.7 Hz, 1H), 7.69 (s, 1H), 7.55-7.41 (m, 4H), 7.39-7.32 (m, 4H), 7.29-7.18 (m, 3H), 7.16-7.09 (m, 1H), 7.03 (d, J=7.3 Hz, 1H), 6.91 (s, 1H), 4.89-4.84 (m, 1H), 3.69 (d, J=11.4 Hz, 1H), 3.45 (t, J=10.2 Hz, 1H), 2.75-2.62 (m, 1H), 2.38 (s, 3H), 2.01-1.61 (m, 3H).

Example 31

(2R,3R)—N1-((S)-5-(3-Chlorophenyl)-9-methyl-2-oxo-2,3-dihydro-1H-benzo[e][1,4]diazepin-3-yl)-3-phenyl-2-(3,3,3-trifluoropropyl)succinamide (31)

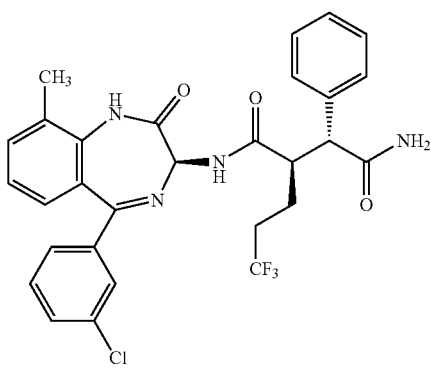

Example 31 was prepared from Intermediate B-5 (560 mg, 1.471 mmol) and Intermediate S-1 (510 mg, 1.471 mmol) according to the general procedure shown for Example 5. After separation of the diastereomers by preparative SFC chromatography (Instrument: Berger SFC MGIII, Column: Chiral IC 25×3 cm, 5 μm; Mobile Phase: 90/10 $CO_2$/MeOH Flow rate: 180 mL/min; Detection at 220 nm.), Example 31 (190 mg, 34%) was obtained. HPLC: RT=9.151 min ($H_2O$/$CH_3CN$ with TFA, SunFire C18 3.5 μm, 4.6×150 mm, gradient=15 min, wavelength=220 and 254 nm); MS(ES): m/z=571.1 [M+H$^+$]; $^1$H NMR (400 MHz, methanol-d$_4$) δ 7.55-7.51 (m, 2H), 7.50 (dd, J=2.1, 1.0 Hz, 1H), 7.48-7.44 (m, 2H), 7.39 (t, J=7.8 Hz, 1H), 7.36-7.29 (m, 3H), 7.29-7.24 (m, 1H), 7.20-7.14 (m, 1H), 7.12-7.06 (m, 1H), 4.96 (s, 1H), 3.72 (d, J=11.2 Hz, 1H), 3.47-3.39 (m, 1H), 2.62-2.48 (m, 1H), 2.44 (s, 3H), 2.42-2.27 (m, 1H), 1.98-1.85 (m, 2H).

Example 32

(2R,3R)—N1-((S)-5-(3-Chlorophenyl)-9-methyl-2-oxo-2,3-dihydro-1H-benzo[e][1,4]diazepin-3-yl)-3-(3-methylisoxazol-4-yl)-2-(3,3,3-trifluoropropyl)succinamide (32)

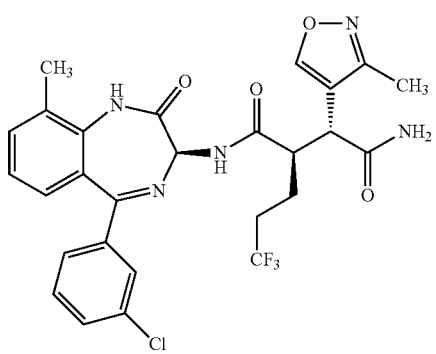

Example 32 was prepared from Intermediate B-5 (100 mg, 0.263 mmol) and Intermediate S-2 (92 mg, 0.263 mmol) according to the general procedure shown for Example 5. Example 32 (36 mg, 52%) was obtained. HPLC: RT=8.633 min ($H_2O$/$CH_3CN$ with TFA, SunFire C18 3.5 μm, 4.6×150 mm, gradient=15 min, wavelength=220 and 254 nm); MS(ES):m/z=576.2 [M+H$^+$]; $^1$H NMR (400 MHz, methanol-d$_4$) δ 8.68 (s, 1H), 7.59-7.56 (m, 1H), 7.55-7.49 (m, 2H), 7.45-7.38 (m, 2H), 7.23-7.13 (m, 2H), 5.14 (s, 1H), 3.64 (d, J=11.2 Hz, 1H), 3.24 (dt, J=11.1, 7.1 Hz, 1H), 2.66-2.53 (m, 1H), 2.47 (s, 3H), 2.43-2.28 (m, 1H), 2.26 (s, 3H), 1.97-1.86 (m, 2H).

Example 33

(2R,3R)—N1-((S)-5-(4-Fluorophenyl)-9-methyl-2-oxo-2,3-dihydro-1H-benzo[e][1,4]diazepin-3-yl)-3-(3-methylisoxazol-4-yl)-2-(3,3,3-trifluoropropyl)succinamide

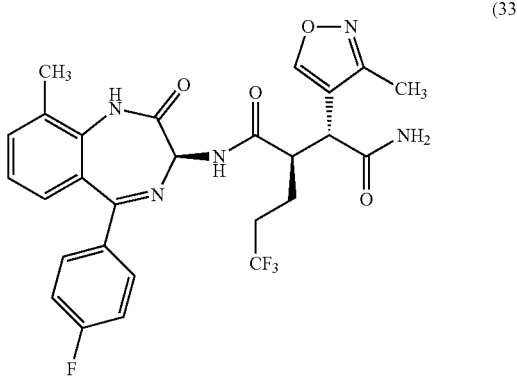

(33)

Example 33 was prepared from Intermediate B-3 (100 mg, 0.275 mmol) and Intermediate S-2 (96 mg, 0.2775 mmol) according to the general procedure shown for Example 5. Example 33 (17 mg, 11%) was obtained. HPLC: RT=8.204 min ($H_2O/CH_3CN$ with TFA, SunFire C18 3.5 µm, 4.6×150 mm, gradient=15 min, wavelength=220 and 254 nm); MS(ES):m/z=560.3 [M+H$^+$]; $^1$H NMR (400 MHz, methanol-$d_4$) δ 8.67 (s, 1H), 7.60-7.48 (m, 3H), 7.23-7.12 (m, 4H), 5.14 (s, 1H), 3.64 (d, J=11.2 Hz, 1H), 3.24 (dt, J=11.4, 7.1 Hz, 1H), 2.64-2.50 (m, 1H), 2.46 (s, 3H), 2.41-2.28 (m, 1H), 2.26 (s, 3H), 1.97-1.85 (m, 2H).

Example 34

(2R,3R)—N1-((S)-5-(3-(Difluoromethyl)phenyl)-9-methyl-2-oxo-2,3-dihydro-1H-benzo[e][1,4]diazepin-3-yl)-3-phenyl-2-(3,3,3-trifluoropropyl)succinamide (34)

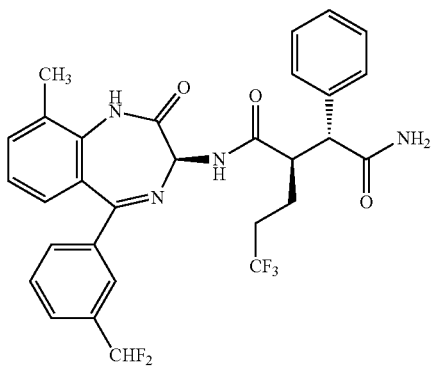

Example 34 was prepared from Intermediate B-6 (100 mg, 0.252 mmol) and Intermediate S-1 (87 mg, 0.252 mmol) according to the general procedure shown for Example 5. After separation of the diastereomers by preparative SFC chromatography (Instrument: Berger SFC MGII, Column: Chiral IC 25×3 cm, 5 µm; Mobile Phase: 88/12 $CO_2$/MeOH Flow rate: 85 mL/min; Detection at 220 nm.), Example 34 (30 mg, 20%) was obtained. HPLC: RT=8.869 min ($H_2O/CH_3CN$ with TFA, SunFire C18 3.5 µm, 4.6×150 mm, gradient=15 min, wavelength=220 and 254 nm); MS(ES):m/z=587.3 [M+H$^+$]; $^1$H NMR (400 MHz, methanol-$d_4$) δ 7.72-7.65 (m, 2H), 7.64-7.58 (m, 1H), 7.52 (dd, J=14.7, 7.0 Hz, 2H), 7.42 (dd, J=7.8, 1.4 Hz, 2H), 7.29-7.11 (m, 5H), 6.69 (t, J=56.6 Hz, 1H), 4.98 (s, 1H), 3.74 (d, J=11.0 Hz, 1H), 3.53-3.45 (m, 1H), 2.54-2.43 (m, 2H), 2.41 (s, 3H), 2.04-1.95 (m, 2H).

Example 35

(2R,3R)—N1-((S)-9-Cyclopropoxy-5-(3-fluorophenyl)-2-oxo-2,3-dihydro-1H-benzo[e][1,4]diazepin-3-yl)-3-phenyl-2-(3,3,3-trifluoropropyl)succinamide

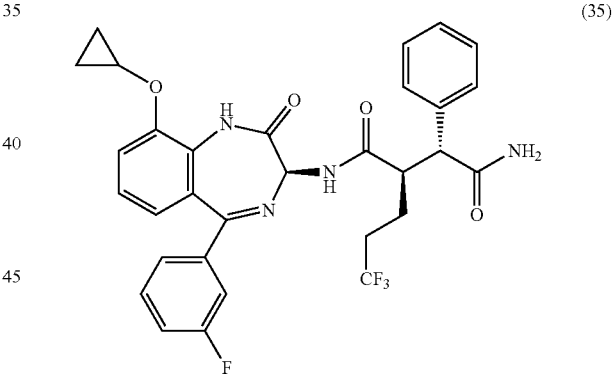

(35)

Example 35 was prepared from Intermediate B-7 (106 mg, 0.326 mmol) and Intermediate S-1 (101 mg, 0.358 mmol) according to the general procedure shown for Example 5. After separation of the diastereomers by preparative SFC chromatography (Berger SFC MGII, Cel4, 250×20 mm ID, 5 µm, 83/17 $CO_2$/MeOH, 85 mL/min), Example 35 (15 mg, 7%) was obtained. HPLC: RT=10.684 min ($H_2O/CH_3CN$ with TFA, SunFire C18 3.5 µm, 4.6×150 mm, gradient=15 min, wavelength=220 and 254 nm); MS(ES):m/z=597 [M+H$^+$]; $^1$H NMR (400 MHz, methanol-$d_4$) δ 7.62-7.35 (m, 4H), 7.35-7.08 (m, 7H), 6.85 (dd, J=8.0, 1.2 Hz, 1H), 5.00 (s, 1H), 3.96 (s, 1H), 3.72 (d, J=11.2 Hz, 1H), 3.37 (s, 1H), 2.68-2.23 (m, 2H), 1.92 (d, J=4.4 Hz, 2H), 1.01-0.79 (m, 4H).

Example 36

(2R,3R)-3-(4-Chlorophenyl)-N1-((S)-9-methoxy-2-oxo-5-phenyl-2,3-dihydro-1H-benzo[e][1,4]diazepin-3-yl)-2-(3,3,3-trifluoropropyl)succinamide (36)

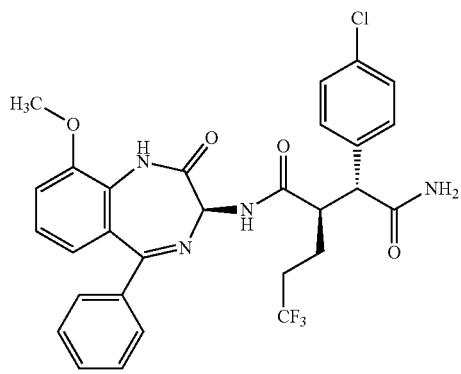

Example 36 was prepared from Intermediate B-10 (35 mg, 0.079 mmol) and Intermediate S-4 (30 mg, 0.079 mmol) according to the general procedure shown for Example 5. Example 36 (3 mg, 8%) was obtained. HPLC: RT=9.079 min ($H_2O/CH_3CN$ with TFA, SunFire C18 3.5 μm, 4.6×150 mm, gradient=15 min, wavelength=220 and 254 nm); MS(ES):m/z=587 [M+H$^+$]; $^1$H NMR (400 MHz, methanol-$d_4$) δ 7.51-7.27 (m, 10H), 7.25-7.21 (m, 1H), 7.20-7.13 (m, 1H), 6.81 (dd, J=7.7, 1.3 Hz, 1H), 5.02 (s, 1H), 3.97 (s, 3H), 3.69 (d, J=11.4 Hz, 1H), 2.53-2.39 (m, 1H), 2.38-2.25 (m, 1H), 1.95-1.81 (m, 2H).

Comparative Compounds 37 to 40

Comparative Compounds 37 to 40 can be prepared according to the procedures described in U.S. Pat. No. 7,053,084 for Examples 8, 12a, 38, and 45a, respectively.

TABLE 1

| Comparative Compound | U.S. Pat. No. 7,053,084 | Structure |
|---|---|---|
| 37 | Ex. 8 | 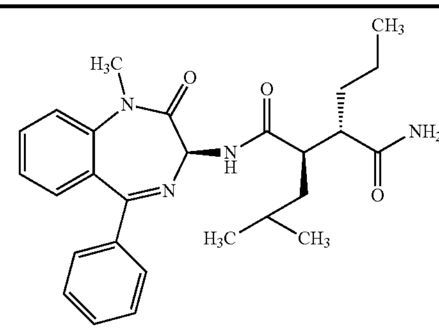 |
| 38 | Ex. 12a | 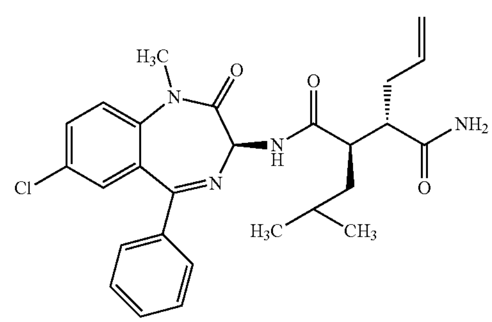 [SMILES: C=CC[C@H](C(N)=O)[C@@H](CC(C)C)C(=O)N[C@H]1N=C(c2ccccc2)c2cc(Cl)ccc2N(C)C1=O] |
| 39 | Ex. 38 | 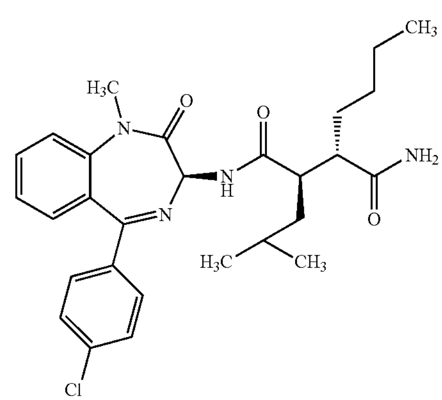 [SMILES: CCCC[C@H](C(N)=O)[C@@H](CC(C)C)C(=O)N[C@H]1N=C(c2ccc(Cl)cc2)c2ccccc2N(C)C1=O] |

TABLE 1-continued

| Comparative Compound | U.S. Pat. No. 7,053,084 | Structure |
|---|---|---|
| 40 | Ex. 45a | 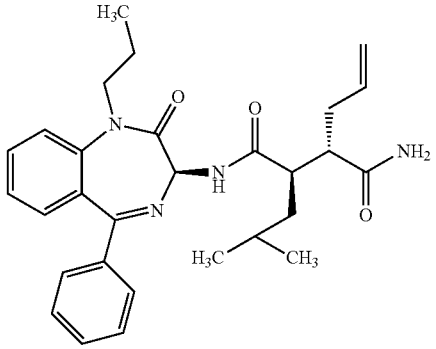 [SMILES: C=CC[C@H](C(N)=O)[C@@H](CC(C)C)C(=O)N[C@H]1N=C(c2ccccc2)c2ccccc2N(CCC)C1=O] |

Biological Assays

The pharmacological properties of the compounds of this invention may be confirmed by a number of biological assays. The exemplified biological assays, which follow, have been carried out with compounds of the invention.

Notch-CBF1 Transactivation Assay

The Notch-CBF1 (C-promoter binding factor I) cell based transactivation assay is based on the ability of the released Notch intracellular domain fragments (NICDs) to function as transcription factors in conjunction with CBF1 and other nuclear factors. Luciferase assays were used to measure the antagonism of Notch-CBF1 transcriptional activity. HeLa cervical cancer cells are transiently co-transfected with pCDNA3.1/Hygro plasmids containing truncated Notch 1, Notch 2, Notch 3, or Notch 4 receptors and a PGL3 luciferase reporter vector containing 4 copies of CBF1 binding site. The cells were then tested for Notch-CBF1 activity in the absence or presence of test compounds. HeLa cells, maintained in DMEM (high glucose with HEPES), 1× glutamine/penicillin/streptomycin and 10% Fetal Bovine serum, were transiently transfected in a T175 Flask (4.5×10⁶ cells/flask) using the Monster Transfection Kit (Minis #MIR2906) according to manufacturers specifications. Table 2 denotes respective DNA quantity for the transfections.

TABLE 2

| | DNA (μg) | CBF1 (μg) | Vector (μg) | Total DNA (μg) |
|---|---|---|---|---|
| human Notch 1 | 6 | 14.4 | 15.6 | 36.0 |
| human Notch 2 | 2 | 14.4 | 19.6 | 36.0 |
| human Notch 3 | 0.3 | 14.4 | 21.3 | 36.0 |
| human Notch 4 | 4 | 14.4 | 17.6 | 36.0 |

Six hours post-transfection, cells were trypsinized and plated into a 384-well black Poly-D-lysine coated tissue culture plate at a density of 5×10³ cells/well in 95 μL assay media (DMEM (high glucose with HEPES), 1× glutamine/penicillin/streptomycin, 0.0125% BSA, 1× non-essential amino acids). Assay media (5 μL) containing test compounds in final concentrations ranging from 5 μM to 8.4×10⁻⁵ μM (3 fold serial dilutions) were added to the cells and the cell plates were then incubated for 18 hours at 37° C. and 5% $CO_2$. Control wells contained DMSO vehicle (total counts) or 0.5 μM of an in-house small molecule inhibitor (background counts). Duplicates were used for each sample. Luciferase activity was measured after a 20-minute incubation with 50 μl STEADY-GLO® luciferase reagents according to manufacturer's specifications (Promega, Cat. #E2550) and analyzed by Envision plate reader (PerkinElmer, Boston, Mass.).

The antagonist effect of compounds was expressed as 100× [1−(average sample−average background)/(average total−average background)] where sample is the luciferase activity in the presence of test compound, background is equal to the luciferase activity in the presence of the small molecule inhibitor control and the total is signal induced in DMSO wells. Data was plotted using a four parameter logistic fit equation and the $IC_{50}$ value was defined as the concentration of compound that inhibited 50% of the luciferase activity.

Table 3 below lists the Notch 1 and Notch 3 $IC_{50}$ values for Examples 1-36 of this invention and Comparative Compounds 37-40 measured in the Notch-CBF1 Transactivation Assay hereinabove. In some instances, the value is an average of multiple experiments where N is the number of experiments conducted. The compounds of the present invention, as exemplified by the Examples 1-36 showed Notch 1 values of 24.2 nM or less and Notch 3 $IC_{50}$ values of 22.9 nM or less.

TABLE 3

| Example | Notch 1 ($IC_{50}$, nM) | N | Notch 3 ($IC_{50}$, nM) | N |
|---|---|---|---|---|
| 1 | 3.8 | 9 | 3.5 | 9 |
| 2 | 2.3 | 9 | 2.4 | 9 |
| 3 | 2.7 | 3 | 1.6 | 3 |
| 4 | 4.2 | 9 | 4.6 | 7 |
| 5 | 4.3 | 3 | 14.2 | 3 |
| 6 | 3.2 | 1 | 3.2 | 2 |
| 7 | 1.8 | 5 | 1.6 | 5 |
| 8 | 2.9 | 1 | 3.6 | 1 |
| 9 | 5.3 | 6 | 4.0 | 6 |
| 10 | 19.3 | 1 | 22.9 | 1 |
| 11 | 12.9 | 2 | 10.3 | 2 |
| 12 | 13.6 | 2 | 7.5 | 2 |
| 13 | 8.3 | 2 | 9.4 | 2 |
| 14 | 10.3 | 1 | 9.4 | 1 |
| 15 | 17.8 | 1 | 11.1 | 1 |
| 16 | 16.4 | 1 | 8.6 | 1 |
| 17 | 3.6 | 5 | 2.9 | 5 |
| 18 | 3.7 | 3 | 5.1 | 3 |
| 19 | 3.8 | 1 | 2.8 | 1 |
| 20 | 4.6 | 4 | 4.3 | 4 |
| 21 | 8.6 | 7 | 5.3 | 7 |
| 22 | 16.0 | 3 | 11.6 | 3 |
| 23 | 15.4 | 2 | 13.7 | 2 |
| 24 | 7.5 | 4 | 3.9 | 4 |

TABLE 3-continued

| Example | Notch 1 (IC$_{50}$, nM) | N | Notch 3 (IC$_{50}$, nM) | N |
|---|---|---|---|---|
| 25 | 24.2 | 1 | 19.1 | 1 |
| 26 | 4.7 | 3 | 6.0 | 2 |
| 27 | 15.3 | 4 | 7.0 | 5 |
| 28 | 4.1 | 2 | 4.7 | 2 |
| 29 | 3.0 | 2 | 3.2 | 2 |
| 30 | 10.9 | 5 | 6.8 | 5 |
| 31 | 7.6 | 3 | 5.4 | 3 |
| 32 | 6.1 | 2 | 4.7 | 2 |
| 33 | 19.0 | 2 | 11.5 | 2 |
| 34 | 10.5 | 2 | 7.7 | 2 |
| 35 | 6.4 | 2 | 4.1 | 2 |
| 36 | 1.5 | 1 | 0.9 | 1 |
| Comparative Compound 37 | 64.1 | 1 | 48.3 | 1 |
| Comparative Compound 38 | 42.4 | 2 | 74.5 | 2 |
| Comparative Compound 39 | 5.1 | 3 | 13.5 | 4 |
| Comparative Compound 40 | 12.3 | 1 | 12.5 | 1 |

High Throughput (HT) Metabolic Stability Panel

Compounds administered parenterally enter the blood stream and undergo one or more passes through the liver. Compounds that are not readily metabolized by the liver can be administered at therapeutically effective plasma levels for therapeutically effective periods of time.

Orally administered compounds typically are absorbed through the intestinal walls into the blood stream and undergo a first pass through the liver. Compounds that are not readily metabolized in this first pass through the liver can be distributed to other areas of the body in therapeutically effective amounts.

The metabolic stability assay evaluated CYP-mediated metabolic stability in vitro using human, rat, mouse, dog, and/or monkey microsomes after a ten-minute incubation. Each compound was tested in duplicate.

The results of these assays were expressed as the fraction of parent compound remaining in the reaction mixture after a ten-minute incubation (Percent Remaining) In general, these results were used to evaluate only the extent of CYP-mediated, or NADPH-dependent, metabolism of the test compound. When the compound was significantly metabolized (<40-50% remaining), this indicated high clearance of the compound in vivo due to CYP-mediated metabolism. However, if the compound demonstrated moderate (50-80%) or low (>85%) metabolism in these in vitro assays, high clearance was still possible in vivo via other metabolism and elimination pathways.

The percent remaining results of these assays was predictive of compound clearance in vivo, assuming that CYP-mediated metabolism was a predominant elimination pathway. In different microsomal species, the ranges of results were approximately as shown in Table 4.

TABLE 4

Metabolic Stability - Result Interpretation Guidelines

| CYP-Mediated Clearance | Percent Remaining after 10 minutes | | | | |
|---|---|---|---|---|---|
| | Human | Rat | Mouse | Dog | Monkey |
| Low | >90 | >85 | >85 | >90 | >85 |
| Medium | 60-90 | 40-85 | 50-85 | 55-90 | 40-85 |
| High | <60 | <40 | <50 | <55 | <40 |

Methods and Materials
Incubation with Liver Microsomes

Test compound was received as a 3.5 mM stock solution in 100 percent DMSO. The test compound was diluted to create a 50 μM acetonitrile (ACN) solution containing 1.4% DMSO, which was then used as a 100× stock for incubation with microsomes. Each compound was tested in duplicate separately in each of three species in the Metabolic Stability-Human, Rat, and Mouse assay suite or as individual species in the Metabolic Stability-Dog or Metabolic Stability-Monkey suites. Compound, NADPH, and liver microsome solutions were combined for incubation in three steps:

1. 152 μl of liver microsome suspension, protein concentration of 1.1 mg/ml in 100 mM NaP$_i$, pH 7.4, 5 mM MgCl$_2$ buffer, was pre-warmed at 37° C.

2. 1.7 μl of 50 μM compound (98.6% ACN, 1.4% DMSO) was added to the same tube and pre-incubated at 37° C. for 5 minutes.

3. The reaction was initiated by the addition of 17 μl of pre-warmed 10 mM NADPH solution in 100 mM NaP$_i$, pH 7.4.

The reaction components were mixed well, and 75 μl of the reaction mixture was immediately transferred into 150 μl quench/stop solution (zero-time point, T$_0$). Reactions were incubated at 37° C. for 10 minutes and then an additional 75 μl aliquot was transferred into 150 μl quench solution. Acetonitrile containing 100 μM DMN (a UV standard for injection quality control), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 μl of supernatant extract, containing the mixture of parent compound and its metabolites, was then transferred to a separate 96-well plate for UV-LC/MS-MS analysis to determine the percent of parent compound that remained in the mixture.

TABLE 5

Metabolic Stability Assay - Reaction Components

| Reaction Components | Final Concentration in the Metabolic Stability Assay |
|---|---|
| Compound (Substrate) | 0.5 μM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| MgCl$_2$ | 5.0 mM |
| 37° C. Incubation time | 0 minutes and 10 minutes |
| Quench/Stop Solution (ACN + 100 μM DMN) | 150 μl |
| Sample of Reaction | 75 μl |
| Sedimentation of Denatured Microsomes | 15 minutes |
| UV-LC/MS analysis of supernatant | 0.17 μM |

Sample Analysis—Instrumentation

HPLC: Pump—Thermo Surveyor; Autosampler—CTC/LEAP HTS; UV detector—Thermo Surveyor PDA plus; Column—VARIAN® C18, 3 μm, 2×20 mm with a 0.5 μm in-line filter; Mobile Phase for structural integrity pre-analysis: (A) 98% water, 2% acetonitrile with 10 mM ammonium acetate; (B) 10% water, 90% acetonitrile with 10 mM ammonium acetate; Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile.

Mass Spectrometer: Thermo TSQ QUANTUM® Ultra triple-quadrupole mass spectrometer.

Sample Analysis—Structural Integrity Pre-Analysis

The Metabolic Stability structural integrity pre-analysis was used to assess the purity of compounds being assayed. Compounds were received in 96-well plates as 57 µl of a 3.5 mM DMSO solution. The 3.5 mM compound DMSO stock solutions were diluted 18-fold with a solution containing equal volumes of acetonitrile, isopropanol, and MilliQ-$H_2O$. The resulting solutions (200 µM) were analyzed for structural integrity by LC-UV/MS on a Thermo LCQ Deca XP Plus ion trap mass spectrometer, using a Waters XBridge C18, 5 µm, 2×50 mm column with a Waters Sentry 2.1 mm guard column, and the LC conditions described in the table below, with a 5 µl injection and a flow rate of 1 ml/min. The acquired data reflected purity by UV absorbance at 220 nm. Only results for those compounds with purity greater than 50% were reported.

TABLE 6

Metabolic Stability - Structural Integrity Gradient

| Gradient Time (min) | A% | B% |
|---|---|---|
| 0.00 | 100 | 0 |
| 4.00 | 0 | 100 |
| 5.00 | 0 | 100 |
| 5.10 | 100 | 0 |
| 6.00 | 100 | 0 |

Sample Analysis—Incubated Samples

MS/MS condition optimization was conducted on a Thermo TSQ QUANTUM® triple-quadrupole mass spectrometer equipped with a heated-electrospray (H-ESI) source by automated infusion to obtain the SRM transitions and their corresponding collision energy values. Compound solutions at a concentration of 20 µM in 1:1 methanol:water were infused at a flow rate of 90 µL/min, then combined with the mobile phase at a flow rate of 50 µL/min before being introduced into the source. All compounds were optimized first using mobile phase A and B (50% A and 50% B), and if necessary, using mobile phase C and D (also with a 50:50 composition). The optimized parameters, including polarity, SRM transition and collision energy, were stored in a MICROSOFT ACCESS® database.

The mass spectrometric conditions obtained from automated infusion were used to analyze incubation samples from the Metabolic Stability assay. The injection volume was 5 µl and the flow rate was 0.8 ml/min. The gradient used was shown in the table below. All samples were injected with the gradient using mobile phase A and B first. If necessary (for instance, for chromatographic reasons), samples were re-injected with the same gradient, but using mobile phase C and D. All LC-MS/MS analysis parameters were captured electronically in the raw data files.

TABLE 7

Metabolic Stability - Sample Analysis Gradient

| Gradient Time (min) | A% (or C%) | B% (or D%) |
|---|---|---|
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

Data Analysis

Peak integration was performed with the XCALIBUR® software. The percent remaining calculation was performed by comparing the LC-MS/MS peak areas from the $T_{10 minute}$ samples to those from the $T_{0 minute}$ samples for each compound.

Quality Control

A set of three compounds was tested along with the test compound in each assay plate. Data was accepted and uploaded only if the results for these control compounds fall into the expected ranges shown below.

Metabolic Stability Assay - Control Compound Values by Microsome Species

| Compound | Average Percent Remaining ± SD | | | | |
|---|---|---|---|---|---|
| | Human | Rat | Mouse | Dog | Monkey |
| Nefazodone | 0.4 ± 0.4 | 0.7 ± 0.6 | 0.4 ± 0.3 | 0.4 ± 0.4 | 0.6 ± 0.5 |
| Verapamil | 13.3 ± 3.5 | 4.4 ± 2.1 | 13.0 ± 4.2 | 5.6 ± 1.8 | 0.5 ± 0.5 |
| Carbamezepine | 96 ± 6 | 84 ± 9 | 90 ± 10 | 81 ± 7 | 89 ± 13 |

SD = Standard Deviation

Metabolic Stability Half-Life Panel

The rate of metabolism and half-life determined in vitro in human or animal liver microsomes was used to determine intrinsic clearance ($CL_{int}$) and hepatic clearance (CLh,b) of a compound. These parameters were useful for predicting in vivo human clearance, which defines the level of drug exposure in vivo (Obach et al, 1997, 1999).

The metabolic stability half-life assay panel evaluates the time-course and the rate of CYP-mediated (NADPH-dependent) metabolism in vitro in human, rat, mouse, dog and monkey microsomes. The time course spans a 45-minute incubation, and includes 0, 5, 10, 15, 30, and 45 minute time-points, at each of which the amount of test compound remaining in the mixture was measured.

Result Interpretation Guideline

The results of the metabolic stability half-life assay are expressed as a half-life ($T_{1/2}$, min). In general, these results should be used to evaluate only the extent of CYP-mediated, or NADPH-dependent, metabolism of the test compound. When the compound was significantly metabolized ($T_{1/2}$<14 minutes), this indicated high clearance in vivo due to CYP-mediated metabolism. However, if the compound demonstrated moderate (14-70 minutes) or low (>70 minutes) metabolism in these in vitro assays, high clearance was still possible in vivo via other metabolism and elimination pathways.

The results of these assays were predictive of compound clearance in vivo, assuming that CYP-mediated metabolism was a predominant elimination pathway. In human microsomes, the ranges of results were approximately as shown in the following table:

TABLE 9

Metabolic Stability Half-Life-Result Interpretation Guidelines

| CYP-Mediated Clearance | $T_{1/2}$, minutes Human |
|---|---|
| Low | >70 |
| Medium | 14-70 |
| High | <14 |

Methods and Materials

Liver microsomes were purchased from BD-Biosciences (Woburn, Mass.) and NADPH from AppliChem Inc; all other reagents were obtained from Sigma.

Incubation with Liver Microsomes

Test compound was received as a 3.5 mM stock solution in 100 percent DMSO. The test compound was diluted to create a 50 μM acetonitrile (ACN) solution containing 1.4% DMSO, which was then used as a 100-fold stock for incubation with microsomes. Each compound was tested in human, rat, mouse, dog and monkey liver microsomes. Compound, NADPH and liver microsome solutions were combined for incubation in three steps:

1. 450 μl of liver microsome suspension, protein concentration of 1.1 mg/ml in 100 mM $NaP_i$, pH 7.4, 5 mM $MgCl_2$ buffer, was pre-warmed at 37° C.

2. 5 μl of 50 μM compound (98.6% ACN, 1.4% DMSO) was added to the same tube and pre-incubated at 37° C. for 5 minutes.

3. The reaction was initiated by the addition of 50 μl of pre-warmed 10 mM NADPH solution in 100 mM $NaP_i$, pH 7.4.

Reaction components were mixed well, and 65 μl were immediately transferred into 130 μl quench/stop solution (zero-time point, $T_0$). Reactions were incubated at 37° C. for 5, 10, 15, 30 and 45 minutes and at each time-point a 65 μl aliquot was transferred into 130 μl of quench solution. Acetonitrile containing Internal Standard (100 ng/ml), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 μl of supernatant extract, containing the mixture of parent compound and its metabolites, was then transferred to a separate 96-well plate for LC/MS-MS analysis to determine the percent of parent compound that was remaining in the mixture.

TABLE 10

Metabolic Stability Half-Life Assays - Reaction Components

| Reaction Components | Final Concentration in the Metabolic Stability Assay |
| --- | --- |
| Compound (Substrate) | 0.5 μM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0, 5, 10, 15, 30, and 45 minutes |
| Quench/Stop Solution (ACN + 100 μM DMN) | 130 μl |
| Sample of Reaction | 65 μl |
| Sedimentation of Denatured Microsomes | 15 minutes |

Sample Analysis—Instrumentation

HPLC: Pump—Shimadzu LC-20 AD series binary pumps; Autosampler—CTC/LEAP HTS.

Table 11 below lists the CYP-mediated metabolic half life value for Examples 1-36 of this invention and Comparative Compounds 37-40 measured in the human metabolic stability half-life assay. In some instances, the value is an average of multiple experiments where N is the number of experiments conducted. The compounds of the present invention, as exemplified by Examples 1-36 had metabolic stability half life values of 30 minutes or longer. In contrast, Comparative Compounds 37-40 had metabolic stability half life values of 8 minutes or less.

TABLE 11

| Example | HLM ($t_{1/2}$, min) | N |
| --- | --- | --- |
| 1 | 64 | 3 |
| 2 | >109 | 2 |
| 3 | 73 | 1 |
| 4 | >120 | 2 |
| 5 | 44 | 4 |
| 6 | 41 | 2 |
| 7 | 71 | 1 |
| 8 | 86 | 1 |
| 9 | 30 | 3 |
| 10 | 67 | 1 |
| 11 | 41 | 3 |
| 12 | 93 | 1 |
| 13 | 31 | 1 |
| 14 | 45 | 1 |
| 15 | >120 | 1 |
| 16 | 85 | 1 |
| 17 | 58 | 2 |
| 18 | 78 | 2 |
| 19 | >120 | 1 |
| 20 | 58 | 2 |
| 21 | 52 | 5 |
| 22 | >120 | 1 |
| 23 | 39 | 1 |
| 24 | >120 | 1 |
| 25 | 78 | 2 |
| 26 | 46 | 3 |
| 27 | 54 | 2 |
| 28 | 37 | 1 |
| 29 | 47 | 2 |
| 30 | 45 | 3 |
| 31 | 54 | 2 |
| 32 | 32 | 1 |
| 33 | 49 | 1 |
| 34 | 48 | 1 |
| 35 | 47 | 2 |
| 36 | 31 | 1 |
| Comparative Compound 37 | 8 | 1 |
| Comparative Compound 38 | 6 | 1 |
| Comparative Compound 39 | 6 | 1 |
| Comparative Compound 40 | 3 | 1 |

The exemplified compounds of the invention showed the surprising advantage of low clearance due to CYP-mediated metabolism in the human metabolic stability half life assay. The compounds of the present invention, as exemplified by Examples 1-36, had metabolic half lives values in the range of 30 minutes or longer in the human metabolic stability half life assay. In contrast, Comparative Compounds 37-40 had metabolic half life values of 8 minutes or less in the human metabolic stability assay. Comparative Compounds 37-40 showed high clearance in the human metabolic stability assay, indicating that the compounds were removed by liver microsomes.

The compounds of the present invention (Examples 1-36) have been compared to the Comparative Compounds 37-40 disclosed in U.S. Pat. No. 7,456,172, and have been found to be especially advantageous. The compounds of the present invention had the surprising advantage of the combination of activity as inhibitors of Notch 1 and Notch 3 and superior metabolic stability to liver microsomes. As shown in Tables 3 and 11, in the reported tests, Examples 1-36 of this invention had Notch 1 $IC_{50}$ values of 24.2 nM or less and Notch 3 $IC_{50}$ values of 22.9 nM or less; and human metabolic stability half lives of 30 minutes or longer in the human metabolic stability half life assay. In contrast, in similar tests, Comparative Compounds 37-40 had Notch 1 $IC_{50}$ values of in the range of from 5.1 nM to 64.1 nM and Notch 3 $IC_{50}$ values in the range of 12.5 nM to 74.5 nM; and human metabolic stability half lives of 8 minutes or less.

Human Tumor Xenograft Models in Mice

All rodents were obtained from Harlan Sprague Dawley Co. (Indianapolis, Ind.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in immunocompromized balb/c nu/nu nude or NOD-SCID mice (Harlan Sprague Dawley). Tumors were propagated as subcutaneous transplants in the appropriate mouse strain (Table 12) using tumor fragments obtained from donor mice.

TABLE 12

Histological Types and Host Mouse Strain/Gender Requirement for the Propagation of Various Human Tumor Xenografts in Mice

| Tumor Type | Histology | Mouse Strain | Sex |
|---|---|---|---|
| TALL-1 | ALL | NOD-SCID | female |
| MDA-MB-157 | breast | NOD-SCID | female |
| MDA-MB-468 | breast | NOD-SCID | female |

Preclinical Chemotherapy Trials

The required numbers of animals needed to detect a meaningful response were pooled at the start of the experiment and each was given a subcutaneous implant of a tumor fragment (~20 mg) with a 13-gauge trocar. Tumors were allowed to grow to the pre-determined size window (tumors outside the range were excluded) and animals were evenly distributed to various treatment and control groups. There were typically 8 mice per treatment and control groups, with the exception of experiments conducted in the SAL-IGF (this is not included in Table 12) tumor model, in which there were typically 5 mice per treatment and control group. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

$$\text{Tumor weight} = (\text{length} \times \text{width}^2) \div 2$$

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,
$C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e., TGI≥50%) or log cell kill of 0.5 or greater (LCK≥0.5) for a period equivalent to at least 1 tumor volume doubling time and drug treatment must be for a period equivalent to at least 2 tumor volume doubling time.

Tumor response was also expressed in terms of tumor growth delay (TGD value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e., more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

Drug Administration

In in vitro studies, all agents were dissolved in 100% DMSO and serially diluted in media/10% fetal bovine serum. The following excipients were used for administration of the Notch inhibitors to rodents: ETOH/TPGS/PEG300 (10:10:80). Notch inhibitors were typically administered orally on a schedule of QDx15, 10 day-on-2 day-off-5 day-on, although other schedules had also been evaluated and shown to be efficacious. For example, dosing regimen consisting of QDx12, 4 day-on-3 day-off was shown to be equally efficacious as QDx15, 10 day-on-2 day-off-5 day-on. In the BID studies, the second dose was given 6 to 12 hours after the first dose.

In Vivo Antitumor Activity

The antitumor activity of Example 1 administered orally (PO) was evaluated in human tumor xenografts implanted in mice.

Table 13 below lists the antitumor activity of examples of this invention measured in the Human Tumor Xenograft Models in mice. The compounds of the present invention, as exemplified by Examples 1, 21, 26, 30 and 31, showed antitumor activity with oral administration (PO).

TABLE 13

| Schedule: QD × 10-14, or BID × 10 Oral Administration | | | |
|---|---|---|---|
| | | Antitumor Activity in TALL-1 (LCK) | |
| Example | Dose | BID dosing | QD dosing |
| 1 | 24 | ND | 3.5 |
| 21 | 40 | ND | 2.7 |
| 26 | 10 | 1.4 | ND |
| 30 | 20 | 1.2 | ND |

TALL1: QD × 10.
QD—once daily;
BID—twice daily
LCK—Log Cell Kill

What is claimed is:

1. A compound of Formula (I):

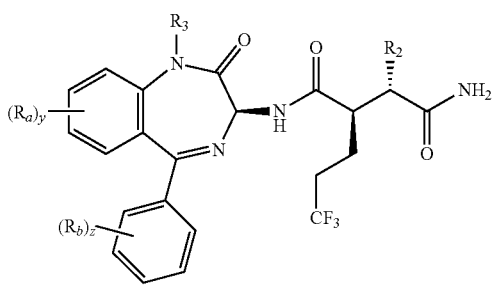

wherein:
$R_2$ is phenyl, fluorophenyl, chlorophenyl, trifluorophenyl, methylisoxazolyl, or pyridinyl;
$R_3$ is H, —CH$_3$, —CH$_2$(cyclopropyl), pyridinyl, chloropyridinyl, or methoxypyridinyl;
each $R_a$ is independently F, Cl, —CH$_3$, —OCH$_3$, —CN, and/or —O(cyclopropyl);
or two adjacent $R_a$ along with the carbon atoms to which they are attached form a dioxole ring;
each $R_b$ is independently F, Cl, —CHF$_2$, and/or —CF$_3$;
y is zero, 1, or 2; and
z is zero, 1, or 2.

2. The compound according to claim 1 wherein:
$R_2$ is phenyl, fluorophenyl, chlorophenyl, or trifluorophenyl.

3. The compound according to claim 1 wherein:
$R_2$ is methylisoxazolyl.

4. The compound according to claim 1 wherein:
$R_2$ is pyridinyl.

5. The compound according to claim 1 wherein:
$R_3$ is H or —CH$_3$.

6. The compound according to claim 1 wherein:
$R_3$ is —CH$_2$(cyclopropyl), pyridinyl, chloropyridinyl, or methoxypyridinyl.

7. A compound according to claim 1 selected from: (2R,3R)—N-((3S)-1-methyl-2-oxo-5-phenyl-2,3-dihydro-1H-1,4-benzodiazepin-3-yl)-3-phenyl-2-(3,3,3-trifluoropropyl)succinamide (1); (2R,3R)-3-(4-fluorophenyl)-N-((3 S)-1-methyl-2-oxo-5-phenyl-2,3-dihydro-1H-1,4-benzodiazepin-3-yl)-2-(3,3,3-trifluoropropyl)succinamide (2); (2R,3R)—N-((3S)-1-methyl-2-oxo-5-phenyl-2,3-dihydro-1H-1,4-benzodiazepin-3-yl)-3-(2,3,4-trifluorophenyl)-2-(3,3,3-trifluoropropyl)succinamide (3); (2R,3R)—N-((3S)-2-oxo-5-phenyl-2,3-dihydro-1H-1,4-benzodiazepin-3-yl)-3-phenyl-2-(3,3,3-trifluoropropyl)succinamide (4); (2R,3R)—N1-((S)-5-(3-fluorophenyl)-9-methyl-2-oxo-2,3-dihydro-1H-benzo[e][1,4]diazepin-3-yl)-3-phenyl-2-(3,3,3-trifluoropropyl)succinamide (5); (2R,3R)—N1-((S)-1-methyl-2-oxo-5-phenyl-2,3-dihydro-1H-benzo[e][1,4]diazepin-3-yl)-3-(3-methylisoxazol-4-yl)-2-(3,3,3-trifluoropropyl)succinamide (6); (2R,3R)—N1-((S)-1-(cyclopropylmethyl)-2-oxo-5-phenyl-2,3-dihydro-1H-benzo[e][1,4]diazepin-3-yl)-3-phenyl-2-(3,3,3-trifluoropropyl)succinamide (7); (2R,3R)—N1-((S)-1-(cyclopropylmethyl)-2-oxo-5-phenyl-2,3-dihydro-1H-benzo[e][1,4]diazepin-3-yl)-3-(4-fluorophenyl)-2-(3,3,3-trifluoropropyl)succinamide (8); (2R,3R)-3-(3-methylisoxazol-4-yl)-N1-((S)-2-oxo-5-phenyl-2,3-dihydro-1H-benzo[e][1,4]diazepin-3-yl)-2-(3,3,3-trifluoropropyl) succinamide (9); (2R,3R)—N1-((S)-2-oxo-5-phenyl-2,3-dihydro-1H-benzo[e][1,4]diazepin-3-yl)-3-(pyridin-3-yl)-2-(3,3,3-trifluoropropyl)succinamide (10); (2R,3R)-3-(3-methyl-4-isoxazolyl)-N-((3S)-2-oxo-5-phenyl-1-(2-pyridinyl)-2,3-dihydro-1H-1,4-benzodiazepin-3-yl)-2-(3,3,3-trifluoropropyl)succinamide (11); (2R,3R)—N-((3S)-2-oxo-5-phenyl-1-(2-pyridinyl)-2,3-dihydro-1H-1,4-benzodiazepin-3-yl)-3-phenyl-2-(3,3,3-trifluoropropyl) succinamide (12); (2R,3R)-3-(3-methyl-4-isoxazolyl)-N-((7S)-6-oxo-9-phenyl-6,7-dihydro-5H-[1,3]dioxolo[4,5-h][1,4]benzodiazepin-7-yl)-2-(3,3,3-trifluoropropyl) succinamide (13); (2R,3R)—N-((3S)-1-(5-methoxy-2-pyridinyl)-2-oxo-5-phenyl-2,3-dihydro-1H-1,4-benzodiazepin-3-yl)-3-(3-methyl-4-isoxazolyl)-2-(3,3,3-trifluoropropyl) succinamide (14); (2R,3R)—N-((3S)-1-(5-methoxy-2-pyridinyl)-2-oxo-5-phenyl-2,3-dihydro-1H-1,4-benzodiazepin-3-yl)-3-phenyl-2-(3,3,3-trifluoropropyl) succinamide (15); (2R,3R)—N-((3S)-1-(6-methoxy-2-pyridinyl)-2-oxo-5-phenyl-2,3-dihydro-1H-1,4-benzodiazepin-3-yl)-3-phenyl-2-(3,3,3-trifluoropropyl) succinamide (16); (2R,3R)—N1-((S)-9-chloro-2-oxo-5-phenyl-2,3-dihydro-1H-benzo[e][1,4]diazepin-3-yl)-3-(3-methylisoxazol-4-yl)-2-(3,3,3-trifluoropropyl)succinamide (17); (2R,3R)—N1-((S)-9-fluoro-2-oxo-5-phenyl-2,3-dihydro-1H-benzo[e][1,4]diazepin-3-yl)-3-(3-methylisoxazol-4-yl)-2-(3,3,3-trifluoropropyl)succinamide (18); (2R,3R)—N1-((S)-9-fluoro-2-oxo-5-phenyl-2,3-dihydro-1H-benzo[e][1,4]diazepin-3-yl)-3-phenyl-2-(3,3,3-trifluoropropyl) succinamide (19); (2R,3R)—N1-((S)-9-methoxy-2-oxo-5-phenyl-2,3-dihydro-1H-benzo[e][1,4]diazepin-3-yl)-3-(3-methylisoxazol-4-yl)-2-(3,3,3-trifluoropropyl)succinamide (20); (2R,3R)—N1-((S)-9-methoxy-2-oxo-5-phenyl-2,3-dihydro-1H-benzo[e][1,4]diazepin-3-yl)-3-phenyl-2-(3,3,3-trifluoropropyl) succinamide (21); (2R,3R)—N-((3S)-1-(5-chloro-2-pyridinyl)-2-oxo-5-phenyl-2,3-dihydro-1H-1,4-benzodiazepin-3-yl)-3-phenyl-2-(3,3,3-trifluoropropyl) succinamide (22); (2R,3R)—N-((3S)-1-(5-chloro-2-pyridinyl)-2-oxo-5-phenyl-2,3-dihydro-1H-1,4-benzodiazepin-3-yl)-3-(3-methyl-4-isoxazolyl)-2-(3,3,3-trifluoropropyl)succinamide (23); (2R,3R)—N1-((S)-9-chloro-2-oxo-5-phenyl-2,3-dihydro-1H-benzo[e][1,4]diazepin-3-yl)-3-phenyl-2-(3,3,3-trifluoropropyl) succinamide (24); (2R,3R)—N1-((S)-7-cyano-9-methoxy-2-oxo-5-phenyl-2,3-dihydro-1H-benzo[e][1,4]diazepin-3-yl)-3-phenyl-2-(3,3,3-trifluoropropyl)succinamide (25); (2R,3R)—N1-((S)-9-cyclopropoxy-2-oxo-5-phenyl-2,3-dihydro-1H-benzo[e][1,4]diazepin-3-yl)-3-phenyl-2-(3,3,3-trifluoropropyl)succinamide (26); (2R,3R)—N1-((S)-5-(4- fluorophenyl)-9-methyl-2-oxo-2,3-dihydro-1H-benzo[e][1,4]diazepin-3-yl)-3-phenyl-2-(3,3,3-trifluoropropyl)succinamide (27); (2R,3R)—N1-((S)-9-methyl-2-oxo-5-(3-(trifluoromethyl)phenyl)-2,3-dihydro-1H-benzo[e][1,4]diazepin-3-yl)-3-(3-methylisoxazol-4-yl)-2-(3,3,3-trifluoropropyl)succinamide (28); (2R,3R)—N1-((S)-9-methyl-2-oxo-5-(3-(trifluoromethyl)phenyl)-2,3-dihydro-1H-benzo[e][1,4]diazepin-3-yl)-3-phenyl-2-(3,3,3-trifluoropropyl)succinamide (29); (2R,3R)—N1-((S)-9-methyl-2-oxo-5-phenyl-2,3-dihydro-1H-benzo[e][1,4]diazepin-3-yl)-3-phenyl-2-(3,3,3-trifluoropropyl) succinamide (30); (2R,3R)—N1-((S)-5-(3-chlorophenyl)-9-methyl-2-oxo-2,3-dihydro-1H-benzo[e][1,4]diazepin-3-yl)-3-phenyl-2-(3,3,3-trifluoropropyl)succinamide (31); (2R,3R)—N1-((S)-5-(3-chlorophenyl)-9-methyl-2-oxo-2,3-dihydro-1H-benzo[e][1,4]diazepin-3-yl)-3-(3-methylisoxazol-4-yl)-2-(3,3,3-trifluoropropyl)succinamide (32); (2R,3R)—N1-((S)-5-(4-fluorophenyl)-9-methyl-2-oxo-2,3-dihydro-1H-benzo[e][1,4]diazepin-3-yl)-3-(3-methylisoxazol-4-yl)-2-(3,3,3-trifluoropropyl)succinamide (33); (2R,3R)—N1-((S)-5-(3-(difluoromethyl)phenyl)-9-methyl-2-oxo-2,3-dihydro-1H-benzo[e][1,4]diazepin-3-yl)-3-phenyl-2-(3,3,3-trifluoropropyl) succinamide (34); (2R,3R)—N1-((S)-9-cyclopropoxy-5-(3-fluorophenyl)-2-oxo-2,3-dihydro-1H-benzo[e][1,4]diazepin-3-yl)-3-phenyl-2-(3,3,3-trifluoropropyl)succinamide (35); and (2R,3R)-3-(4-chlorophenyl)-N1-((S)-9-methoxy-2-oxo-5-phenyl-2,3-dihydro-1H-benzo[e][1,4]diazepin-3-yl)-2-(3,3,3-trifluoropropyl)succinamide (36).

8. A pharmaceutical composition comprising at least one compound according claim 1; and a pharmaceutically acceptable carrier.

9. A method of treating a disease or disorder wherein the disease or disorder is breast cancer, the method comprising administering to a mammalian patient at least one compound according claim 1 and/or at least one salt thereof.

10. The method according to claim 9, further comprising administering sequentially or concurrently one or more addition agents selected from dasatinib, paclitaxel, tamoxifen, dexamethasone, and carboplatin.

* * * * *

UNITED STATES PATENT AND TRADEMARK OFFICE
CERTIFICATE OF CORRECTION

PATENT NO. : 9,133,139 B2  
APPLICATION NO. : 14/429941  
DATED : September 15, 2015  
INVENTOR(S) : Ashvinikumar Gavai et al.

It is certified that error appears in the above-identified patent and that said Letters Patent is hereby corrected as shown below:

Title Page:

Col. 1, item (72) (Inventors), line 4, delete "Lambertsville" and insert -- Lambertville --, therefor.

Col. 2, item (56) (Other Publications), line 1, delete "14/627,537," and insert -- 14/627,573, --, therefor.

Col. 2, item (57) (Abstract), line 11, after "cancer."

insert --
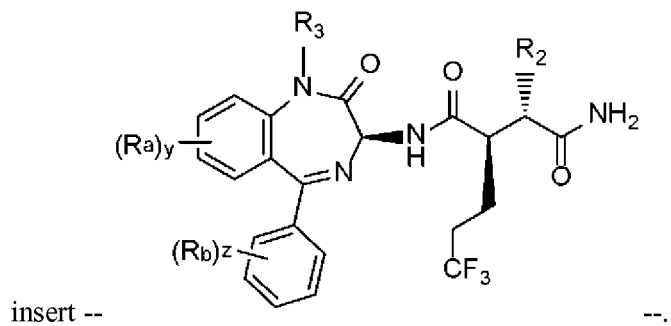
--.

In the Claims:

Claim 8, col. 98, line 11, delete "according claim" and insert -- according to claim --, therefor.

Claim 12, col. 98, line 16, delete "according claim" and insert -- according to claim --, therefor.

Signed and Sealed this  
Tenth Day of May, 2016

Michelle K. Lee  
*Director of the United States Patent and Trademark Office*